(12) United States Patent
Bierlmaier et al.

(10) Patent No.: US 8,633,314 B2
(45) Date of Patent: Jan. 21, 2014

(54) FORMS OF A MULTICYCLIC COMPOUND

(75) Inventors: Stephen Bierlmaier, Thorndale, PA (US); Michael Christie, Phoenixville, PA (US); Laurent Courvoisier, Thorndale, PA (US); Veronique Courvoisier, legal representative, Thorndale, PA (US); R. Scott Field, West Chester, PA (US); R. Curtis Haltiwanger, West Chester, PA (US); Linli He, West Chester, PA (US); Martin J. Jacobs, West Chester, PA (US); Michael Kress, Lansdale, PA (US); Robert E. McKean, Chester Springs, PA (US); Dale R. Mowrey, Phoenixville, PA (US); Joseph Petraitis, Glenmoore, PA (US); Mehran Yazdanian, Philadelphia, PA (US)

(73) Assignee: Cephalon, Inc., Frazer, PA (US)

( * ) Notice: Subject to any disclaimer, the term of this patent is extended or adjusted under 35 U.S.C. 154(b) by 37 days.

(21) Appl. No.: 13/404,137

(22) Filed: Feb. 24, 2012

(65) Prior Publication Data

US 2012/0214998 A1 Aug. 23, 2012

Related U.S. Application Data

(63) Continuation of application No. PCT/US2010/046671, filed on Aug. 25, 2010.

(60) Provisional application No. 61/237,180, filed on Aug. 26, 2009.

(51) Int. Cl.
*C07D 295/12* (2006.01)

(52) U.S. Cl.
USPC ........................................... 544/372

(58) Field of Classification Search
USPC ........................................... 544/372
See application file for complete search history.

(56) References Cited

U.S. PATENT DOCUMENTS

| 7,122,679 B2 | 10/2006 | Ator et al. |
| 2008/0146556 A1 | 6/2008 | Diebold et al. |
| 2011/0059959 A1 | 3/2011 | Chatterjee et al. |

FOREIGN PATENT DOCUMENTS

WO    WO2008/063644    5/2008

OTHER PUBLICATIONS

Byrn et al., Solid-State Chemistry of Drugs, 1999, SSCI, Inc., Second Edition, pp. 62-63.*
Newman et al., Solid-state analysis of the active pharmaceutical ingredient in drug products, DDT, vol. 8, No. 19, Oct. 2003, pp. 898-905.*
Chawla et al., Challenges in Polymorphism of Pharmaceuticals, CRIPS, vol. 5, No. 1, Jan.-Mar. 2004, pp. 9-12.*
Brittain et al., Polymorphism in Pharmaceutical Solids, 1995, vol. 95, p. 228-229.*

* cited by examiner

*Primary Examiner* — Kristin Vajda

(57) ABSTRACT

The present invention provides alternative forms of Compound I,

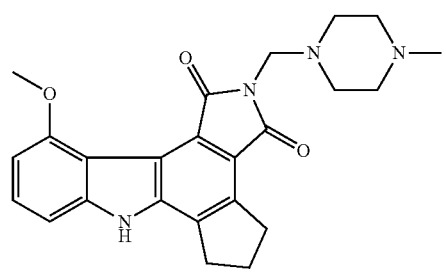

processes to reproducibly make them and methods of treating patients using them.

22 Claims, 51 Drawing Sheets

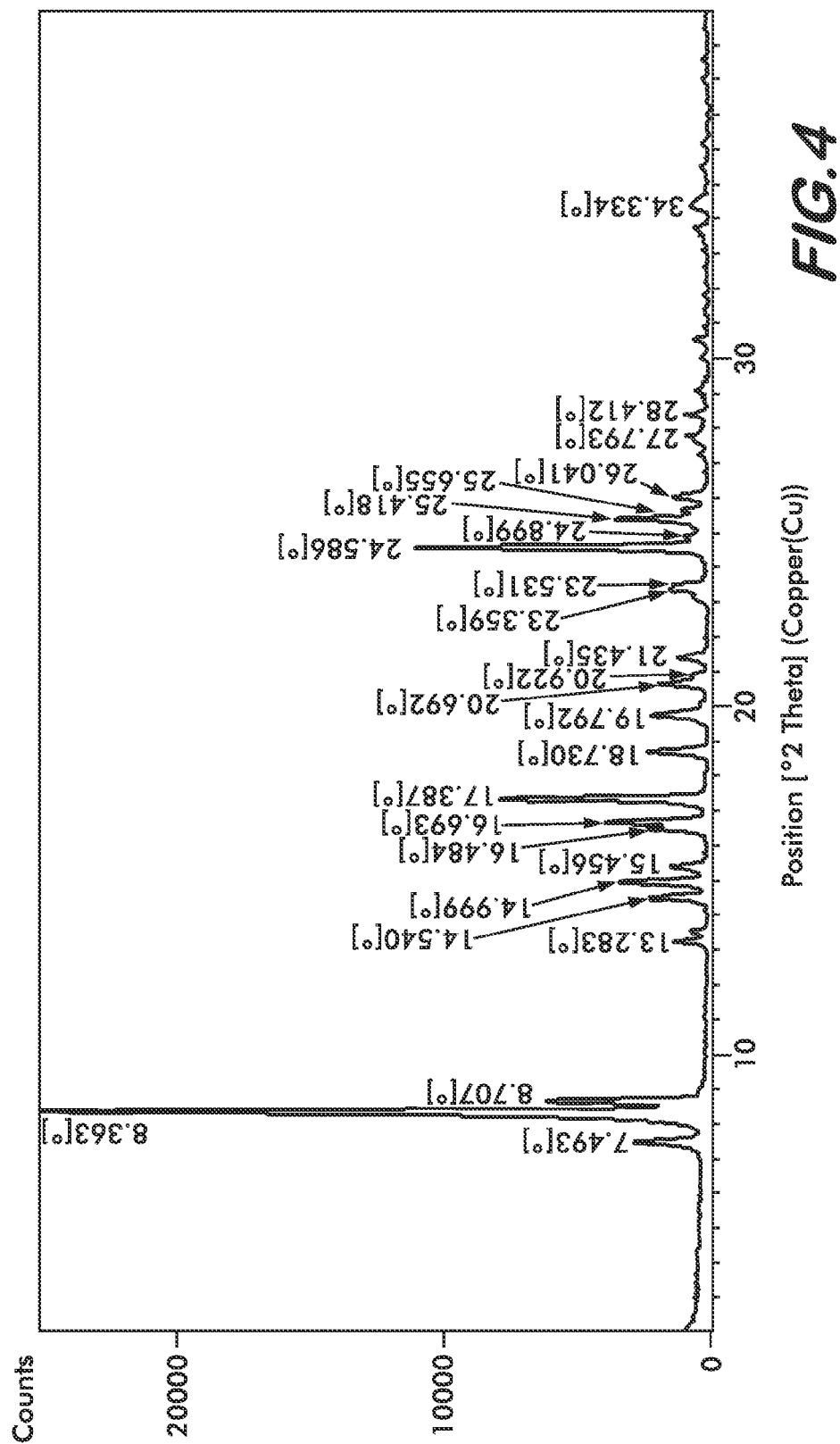

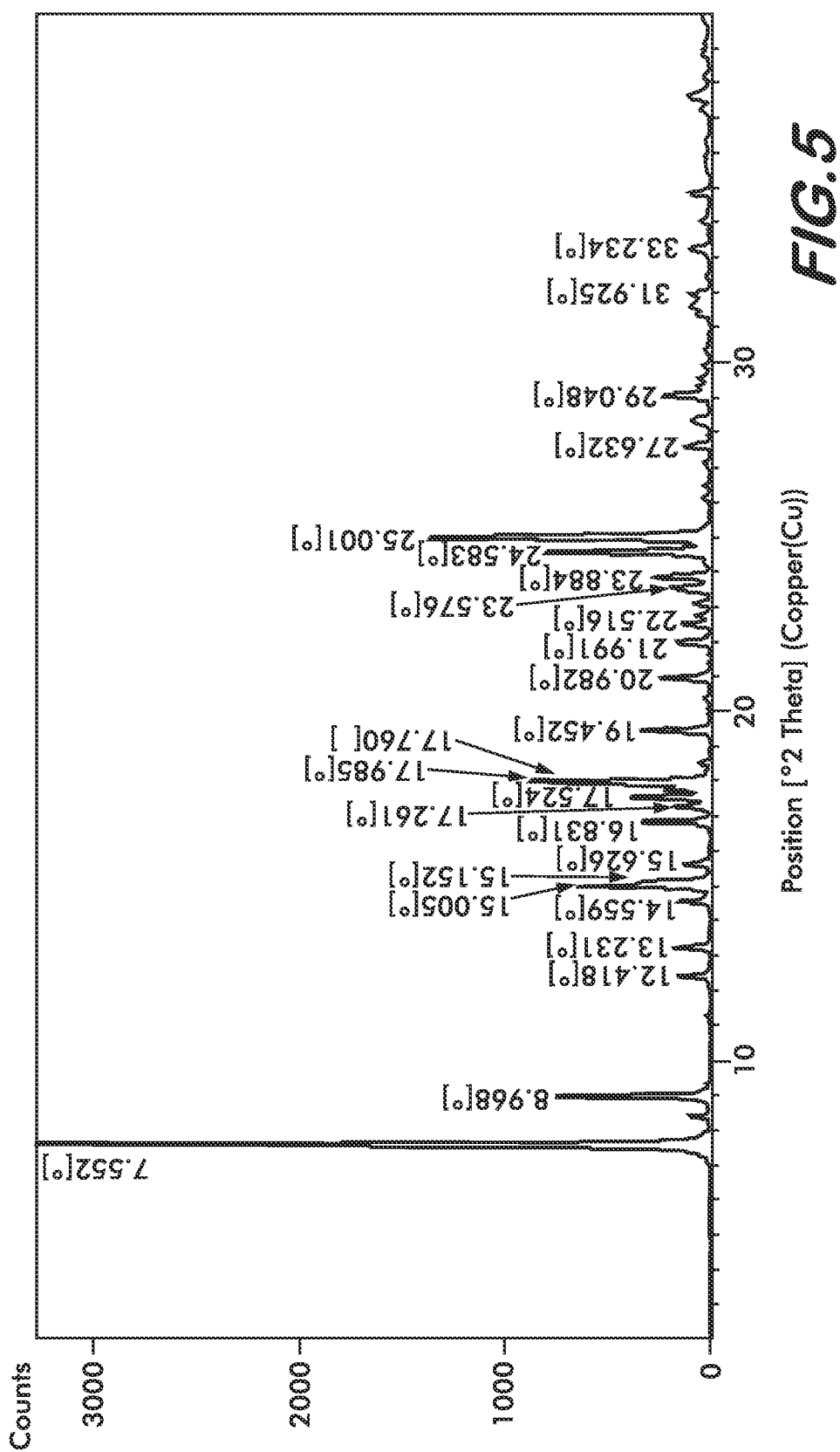

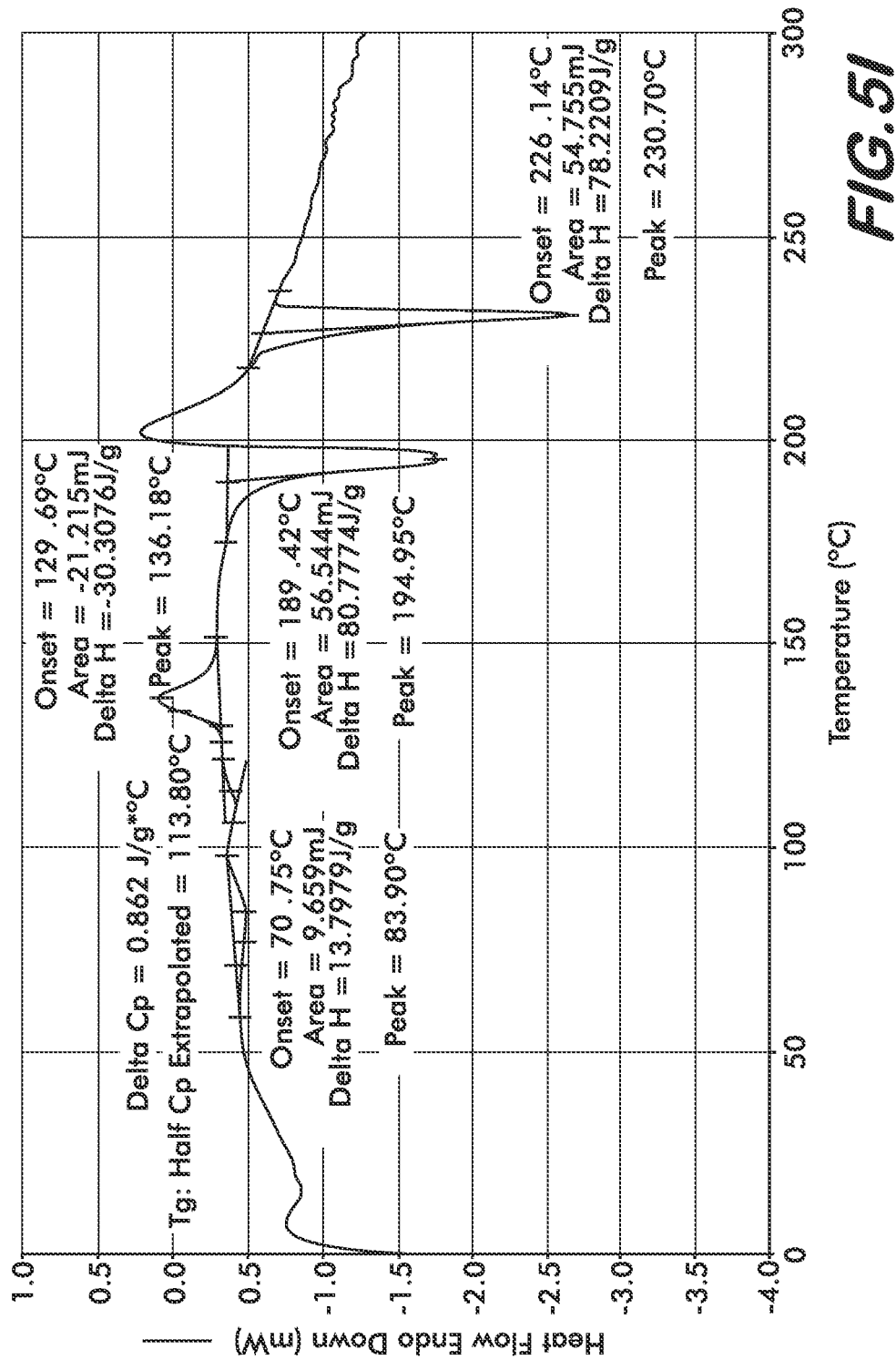

FORMS OF A MULTICYCLIC COMPOUND

FIELD OF THE INVENTION

The present invention relates to compositions which contain novel forms of a multicyclic compound (hereinafter referred to as Compound I), processes to reproducibly make them and pharmaceutical compositions comprising Compound I.

BACKGROUND OF THE INVENTION

Active pharmaceutical ingredients (APIs) can be prepared in a variety of different forms, for example, chemical derivatives, solvates, hydrates, co-crystals, or salts. APIs may also be amorphous, may have different crystalline polymorphs, or may exist in different solvation or hydration states. By varying the form of an API, it is possible to vary the physical properties thereof. For instance, crystalline polymorphs typically have different solubilities such that a more thermodynamically stable polymorph is less soluble than a less thermodynamically stable polymorph. Polymorphs can also differ in properties such as stability, bioavailability, morphology, vapor pressure, density, color, and compressibility. Accordingly, variation of the crystalline state of an API is one of many ways in which to modulate the physical and pharmacological properties thereof.

Poly(ADP-ribose) polymerase (PARP, also called poly (ADP-ribose) synthetase, or PARS) is a nuclear enzyme which catalyzes the synthesis of poly(ADP-ribose) chains from $NAD^+$ in response to single-stranded DNA breaks as part of the DNA repair process (de Murcia, G; de Murcia, J. M. Poly(ADP-ribose) polymerase: a molecular nick-sensor. Trends Biochem. Sci. 1994, 19,172-176; Alvarez-Gonzalez, R.; Pacheco-Rodriguez, G.; Mendoza-Alvarez, H. Enzymology of ADP-ribose polymer synthesis. Mol. Cell. Biochem. 1994, 138, 33). It has been hypothesized that small molecule inhibitors of PARP may play a potential role in the therapeutic treatment of neurodegenerative disorders, cancers, and other PARP and kinase-related diseases.

A specific PARP inhibitor compound, having the chemical designation 4,5,6,7-tetrahydro-11-methoxy-2-[(4-methyl-1-piperazinyl)methyl]-1H-cyclopenta[a]pyrrolo[3,4-c]carbazole-1,3(2H)-dione may have utility in the treatment of breast and ovarian tumors and in conjunction with chemotherapy or radiotherapy for the treatment of other drug-resistant cancers. This compound is represented by the following formula (I):

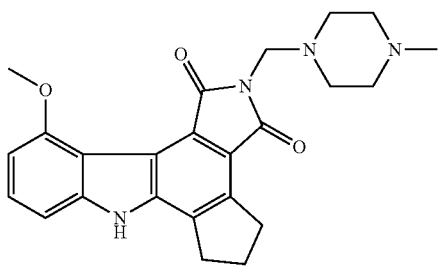

(I)

and is referred to hereinafter as "Compound I". U.S. Pat. No. 7,122,679 and U.S. 2006/0276497 describe Compound I and utility thereof.

Different forms of Compound I can have different melting points, solubilities or rates of dissolution; these physical properties, either alone or in combination, can affect, for example, bioavailability. In light of the potential benefits of alternative forms of APIs, a need exists to identify and prepare alternative forms of Compound I.

SUMMARY OF THE INVENTION

Various forms of Compound I are described, as well as methods for their preparation. Specifically, two polymorphs of anhydrous crystalline forms (Forms $A_0$ and $B_0$), three polymorphs of crystalline monohydrate forms ($HA_0$, $HC_0$ and $HD_0$) and nine solvates ($S2_0$, $S3_0$, $S4_0$, $S5_0$, $S6_0$, $S7_0$, $S9_0$, $S10_0$ and $S12_0$) are described herein. Pharmaceutical compositions comprising one or more of these forms are also described, as well as pharmaceutical compositions further comprising an amorphous form of Compound I ($A_s$). Pharmaceutical compositions comprising one or more of these forms are also described, as are methods of treatment utilizing such compositions.

The pharmaceutical compositions of the present invention may be used in a variety of ways, including but not limited to the enhancement of the anti-tumor activity of radiation or DNA-damaging chemotherapeutic agents (Griffin, R. J.; Curtin, N. J.; Newell, D. R.; Golding, B. T.; Durkacz. B. W.; Calvert, A. H. The role of inhibitors of poly(ADP-ribose) polymerase as resistance-modifying agents in cancer therapy. Biochemie 1995, 77, 408).

BRIEF DESCRIPTION OF THE DRAWINGS

FIG. 5 is an X-ray Powder Diffractogram (XRPD) of Form $HD_0$.

FIG. 41 is a Differential Scanning calorimetry (DSC) Thermogram and Thermo-Gravimetric Analysis (TGA) Thermogram overlay of Form $S3_0$.

FIG. 51 is a Differential Scanning calorimetry (DSC) Thermogram of Form $HC_0$ and $HD_0$ after grinding for 15 minutes.

DETAILED DESCRIPTION OF THE INVENTION

The existence has now been found of a number of forms of Compound I. The preparation and description of these forms is described herein. Spectral data relating to these forms are shown in FIGS. 1-51.

More specifically, the existence has been found of a number of different physical forms of Compound I. Two polymorphs of anhydrous crystalline forms of Compound I (Forms $A_0$ and $B_0$), and three polymorphs of crystalline monohydrate forms ($HA_0$, $HC_0$ and $HD_0$) have been discovered. The letters A and B were assigned for these anhydrous forms and hydrates, with the leading H specifically denoting the hydrate forms. The subscript '0' was further assigned to identify the free base forms. In addition, nine solvates of Compound I ($S2_0$, $S3_0$, $S4_0$, $S5_0$, $S6_0$, $S7_0$, $S9_0$, $S10_0$ and $S12_0$) are described herein. Pharmaceutical compositions comprising one or more of these forms are also described, as well as pharmaceutical compositions further comprising an amorphous form of Compound I ($A_S$).

Figure 1:
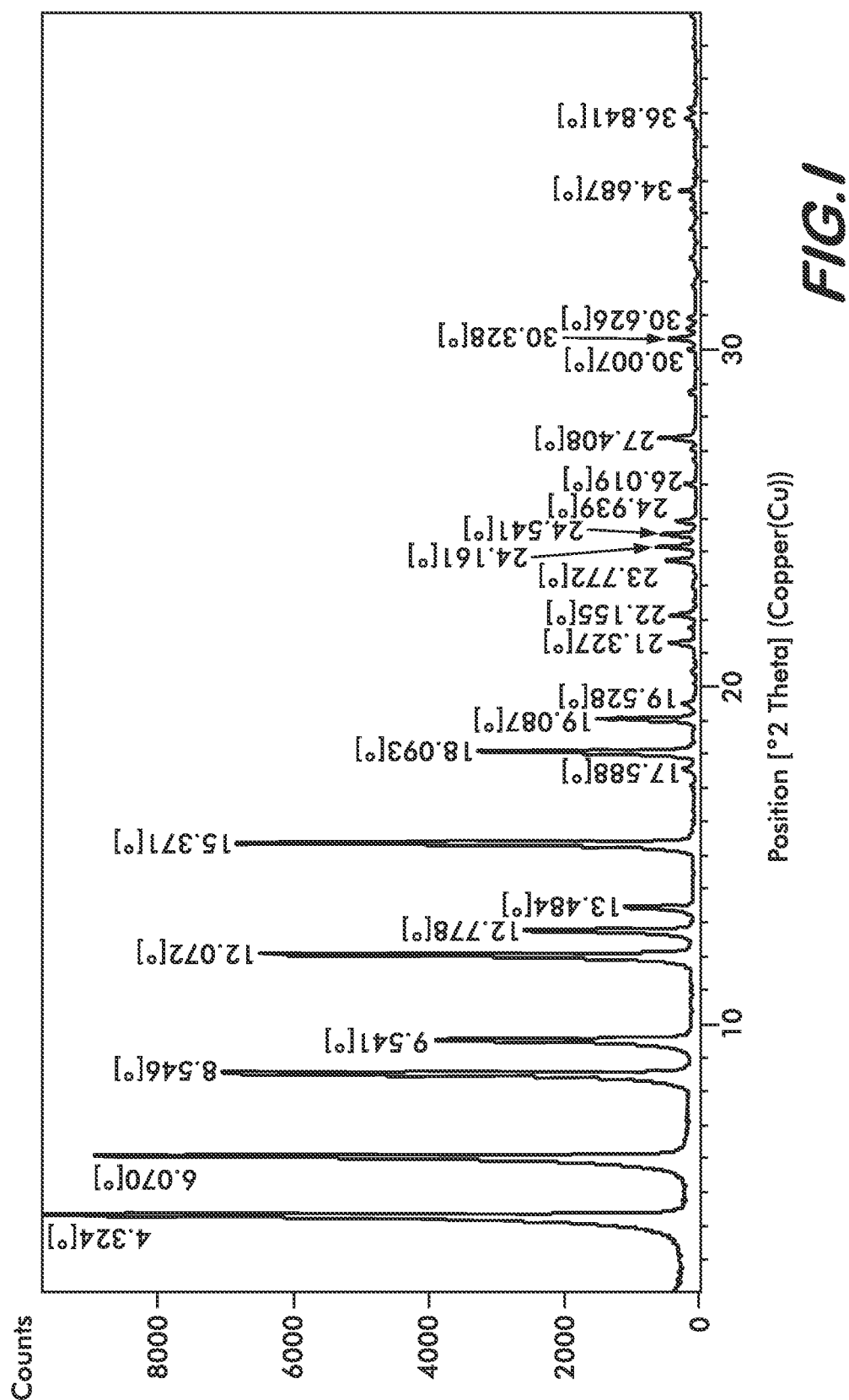
FIG. 1 is an X-ray Powder Diffractogram (XRPD) of Form $A_0$.

Representative XRPD peaks for Form $A_0$ are listed in the following Table 1. The X-Ray diffraction pattern characteristic of Form $A_0$ is shown in FIG. 1.

TABLE 1

| | Form $A_0$ XRPD peaks | | |
|---|---|---|---|
| Peak No. | Angle [°2 Theta] | d-spacing [Angstrom] | Intensity [%] |
| 1 | 4.32 | 20.42 | 100 |
| 2 | 6.07 | 14.55 | 99 |
| 3 | 8.55 | 10.34 | 79 |
| 4 | 9.54 | 9.26 | 44 |
| 5 | 12.07 | 7.33 | 69 |
| 6 | 12.78 | 6.92 | 31 |
| 7 | 13.48 | 6.56 | 11 |
| 8 | 15.37 | 5.76 | 80 |
| 9 | 18.09 | 4.90 | 40 |
| 10 | 19.09 | 4.65 | 17 |
| 11 | 23.77 | 3.74 | 5 |
| 12 | 24.16 | 3.68 | 7 |
| 13 | 24.54 | 3.62 | 6 |
| 14 | 27.41 | 3.25 | 7 |

Figure 2:
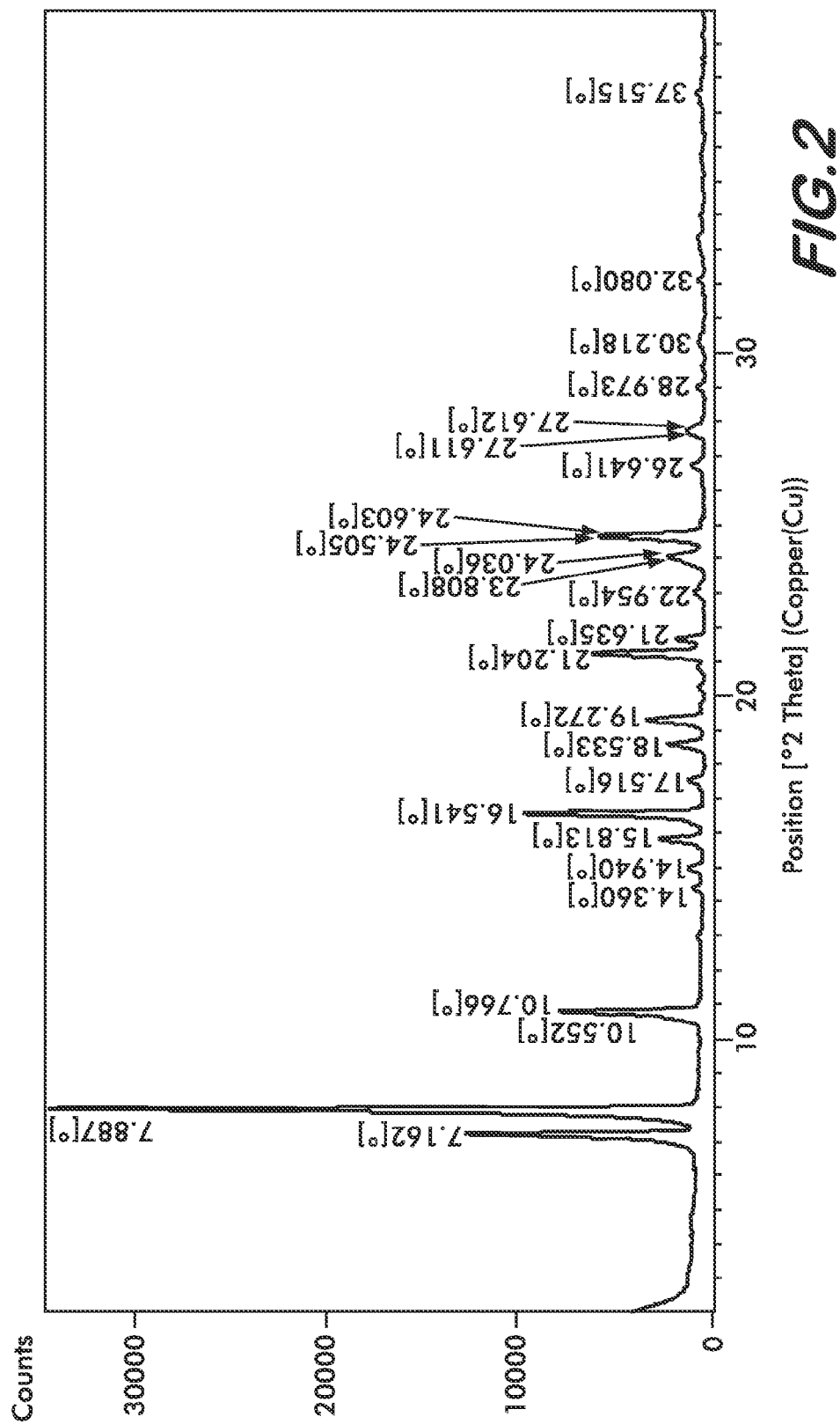
FIG. 2 is an X-ray Powder Diffractogram (XRPD) of Form $B_0$.

Representative XRPD peaks for Form $B_0$ are listed in the following Table 2. The X-Ray diffraction pattern characteristic of Form $B_0$ is shown in FIG. 2.

TABLE 2

Form B₀ XRPD peaks

| Peak No. | Angle [°2 Theta] | d-spacing [Angstrom] | Intensity [%] |
|---|---|---|---|
| 1 | 7.16 | 12.33 | 36 |
| 2 | 7.89 | 11.20 | 100 |
| 3 | 10.55 | 8.38 | 6 |
| 4 | 10.77 | 8.21 | 22 |
| 5 | 15.81 | 5.60 | 7 |
| 6 | 16.54 | 5.35 | 28 |
| 7 | 18.53 | 4.78 | 6 |
| 8 | 19.27 | 4.60 | 9 |
| 9 | 21.20 | 4.19 | 18 |
| 10 | 24.04 | 3.70 | 6 |
| 11 | 24.61 | 3.62 | 17 |
| 12 | 24.65 | 3.61 | 16 |

Figure 3:
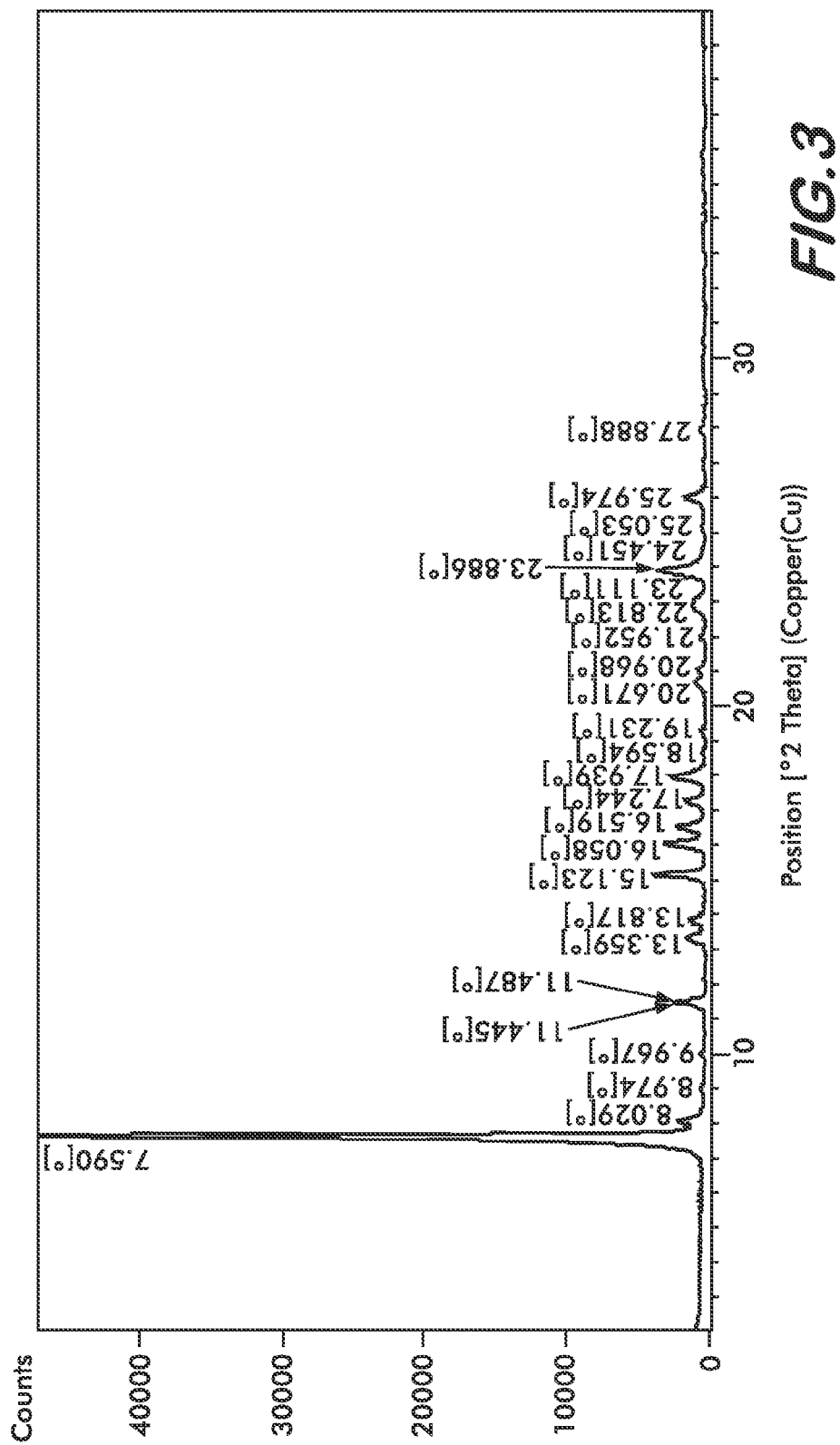
FIG. 3 is an X-ray Powder Diffractogram (XRPD) of Form $HA_0$.

Representative XRPD peaks for Form $HA_0$ are listed in the following Table 3. The X-Ray diffraction pattern characteristic of Form $HA_0$ is shown in FIG. 3.

TABLE 3

Form $HA_0$ XRPD peaks

| Peak No. | Angle [°2 Theta] | d-spacing [Angstrom] | Intensity [%] |
|---|---|---|---|
| 1 | 7.59 | 11.64 | 100 |
| 2 | 15.12 | 5.85 | 7.88 |
| 3 | 16.06 | 5.52 | 6.36 |
| 4 | 17.94 | 4.94 | .5.41 |
| 5 | 23.89 | 3.72 | 7.95 |

Figure 4I:
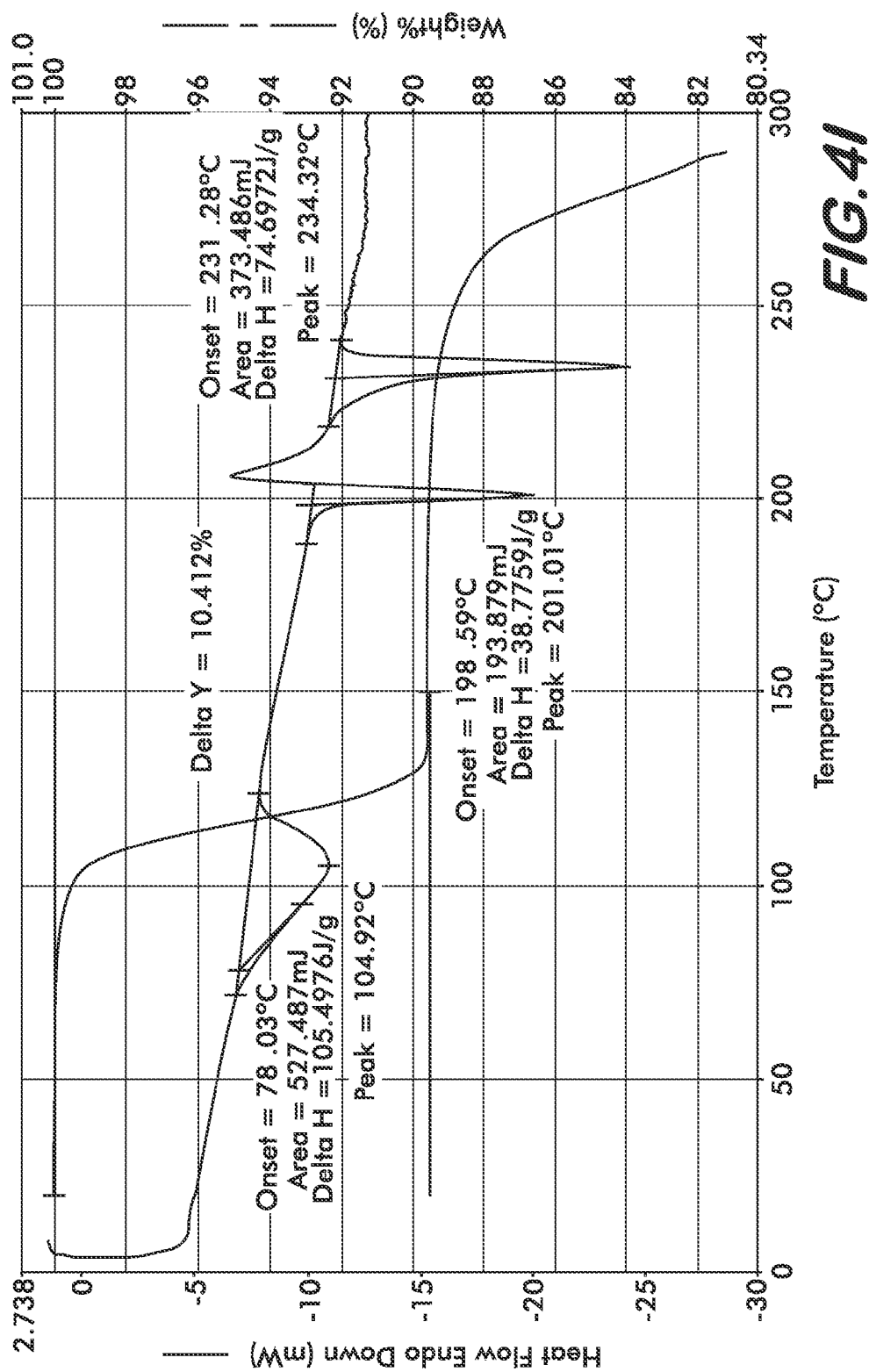
FIG. 4 is an X-ray Powder Diffractogram (XRPD) of Form $HC_0$.
Figure 42:
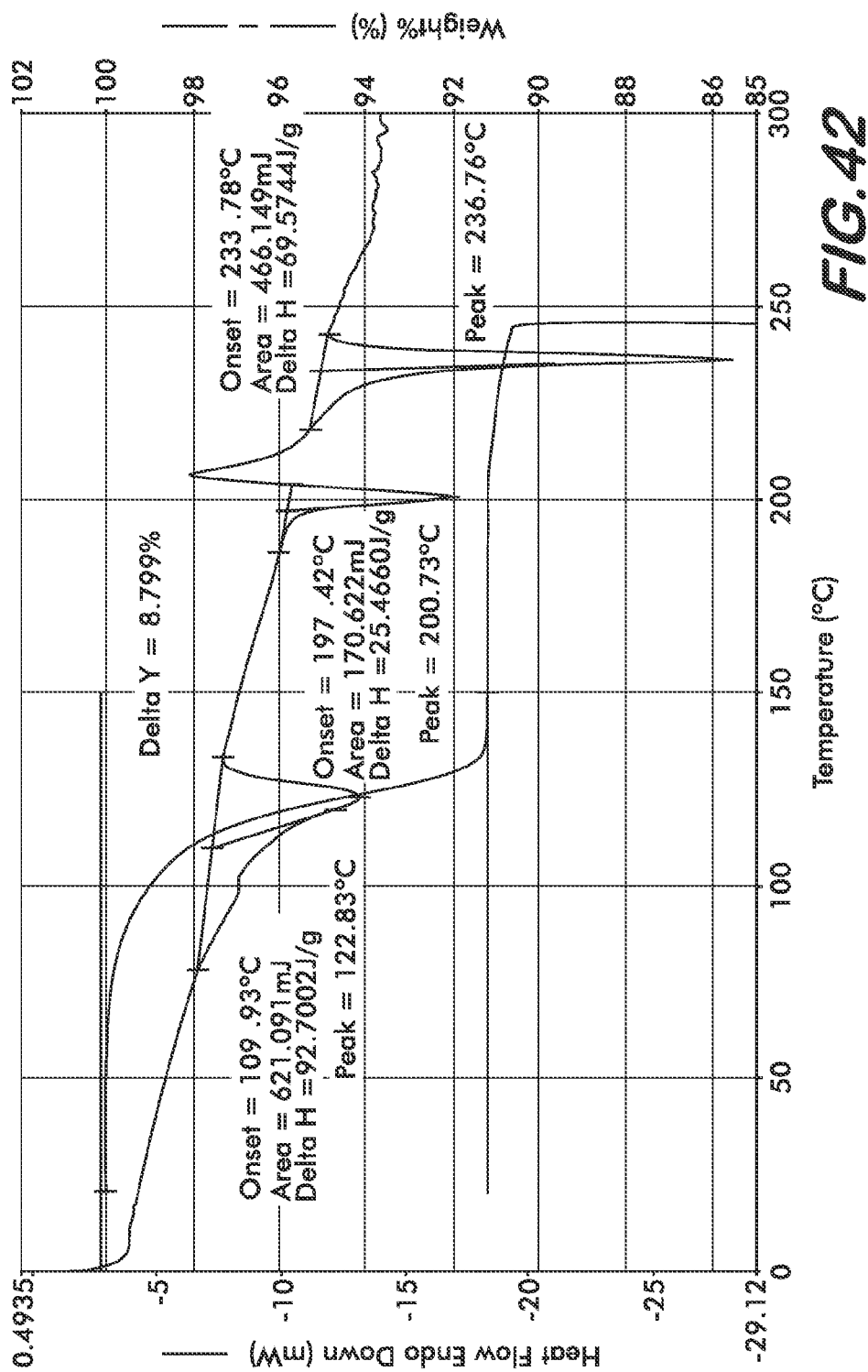
FIG. 42 is a Differential Scanning calorimetry (DSC) Thermogram and Thermo-Gravimetric Analysis (TGA) Thermogram overlay of Form $S4_0$.
Figure 43:
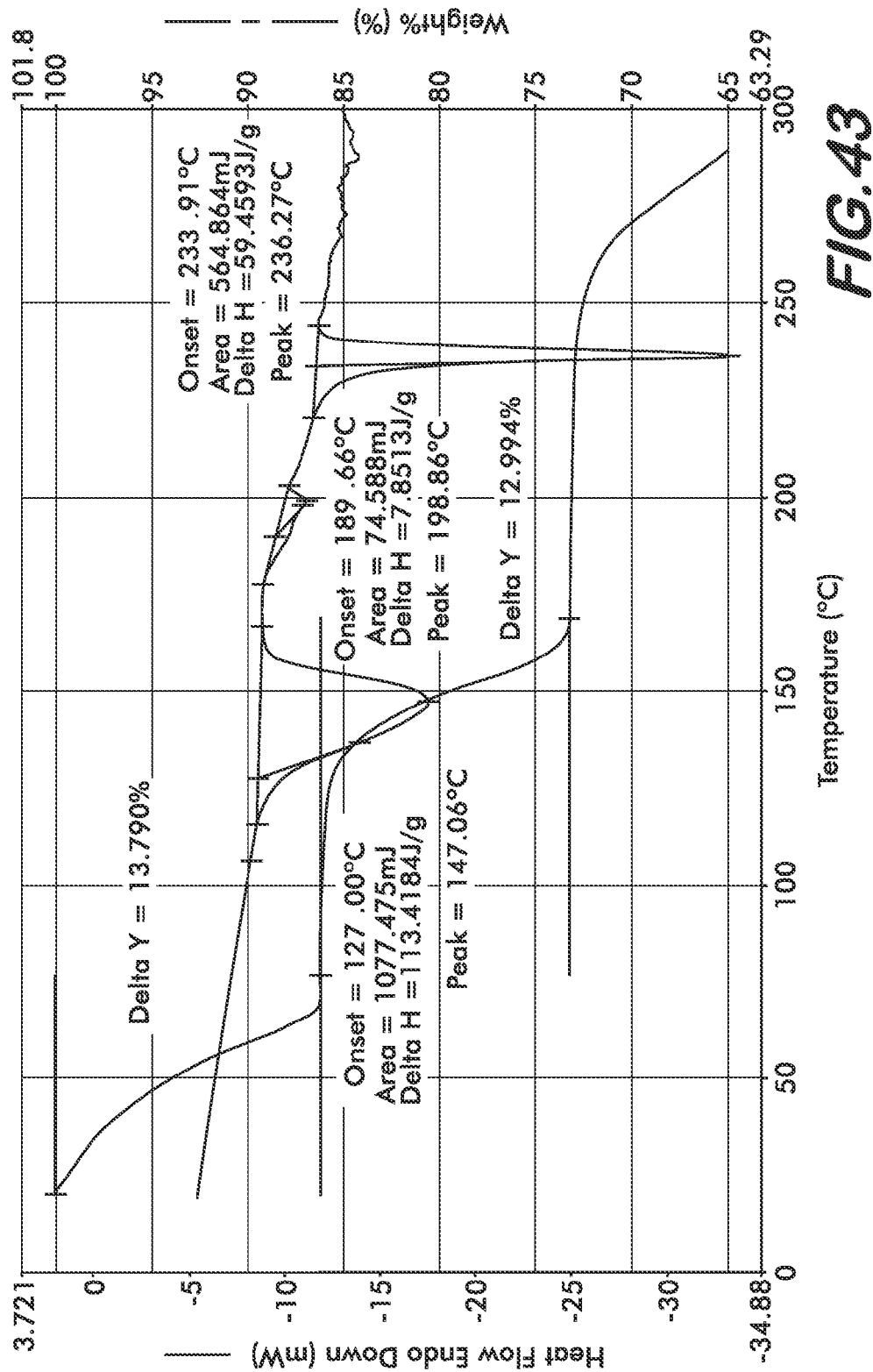
FIG. 43 is a Differential Scanning calorimetry (DSC) Thermogram and Thermo-Gravimetric Analysis (TGA) Thermogram overlay of Form $S5_0$.
Figure 44:
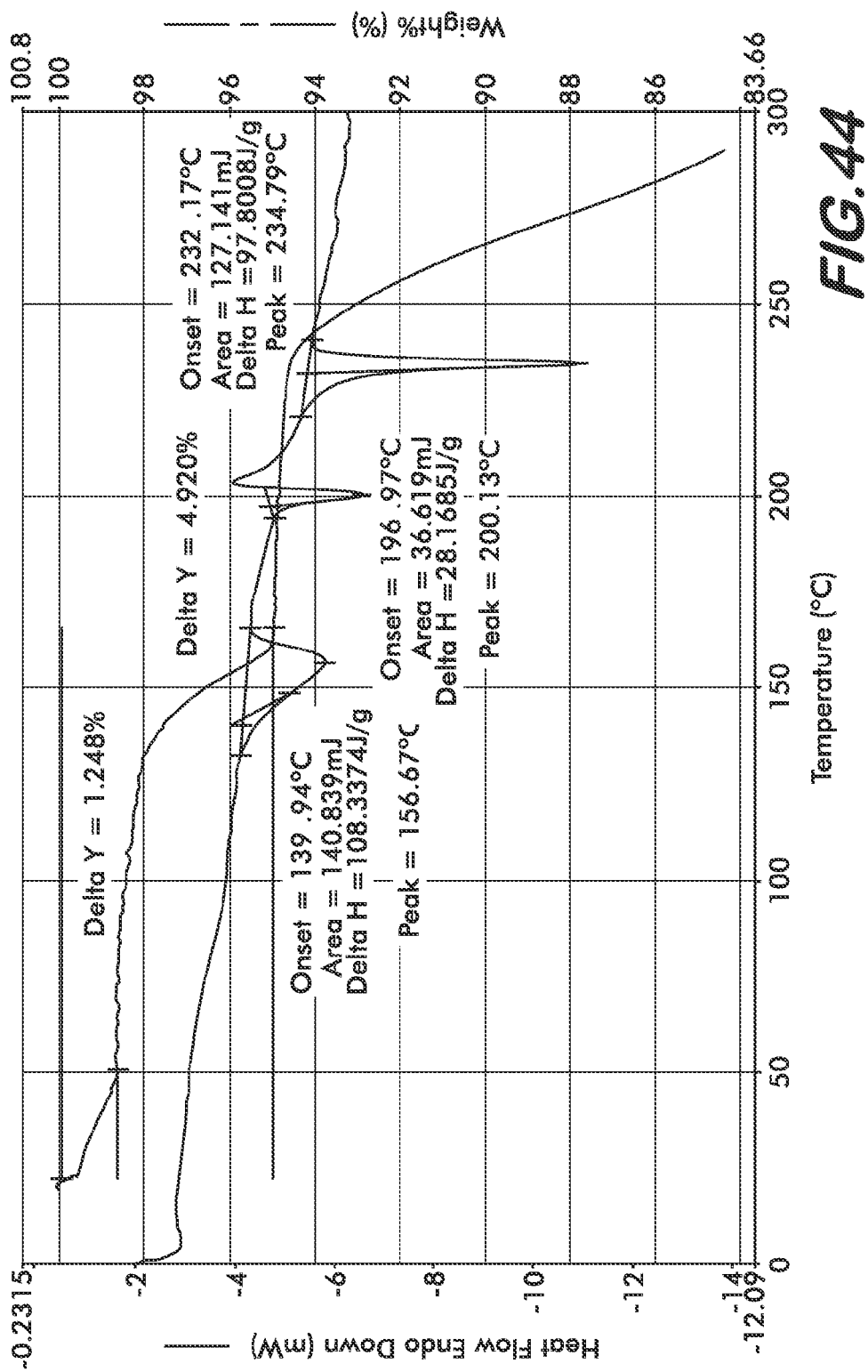
FIG. 44 is a Differential Scanning calorimetry (DSC) Thermogram and Thermo-Gravimetric Analysis (TGA) Thermogram overlay of Form $S6_0$.
Figure 45:
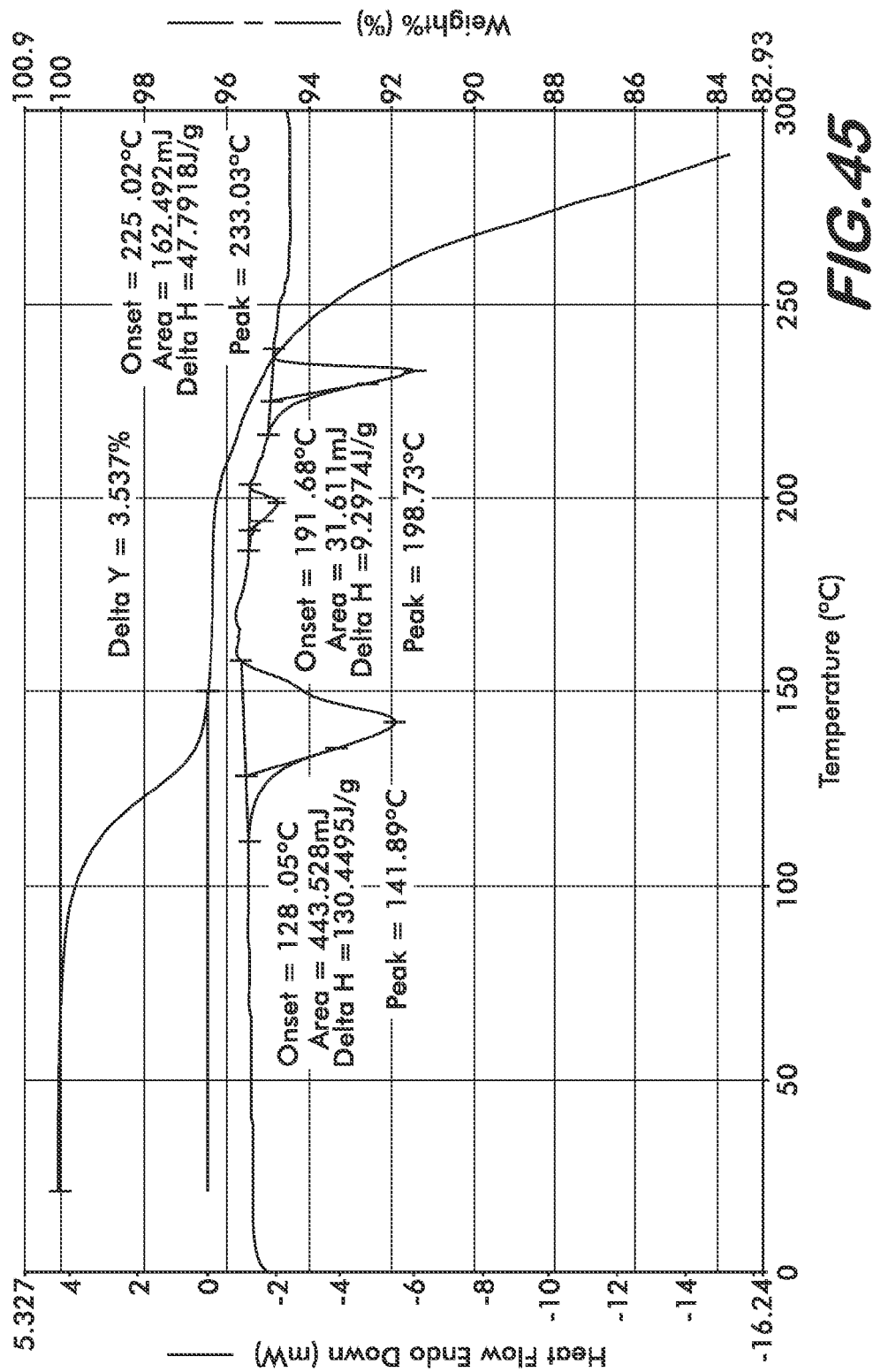
FIG. 45 is a Differential Scanning calorimetry (DSC) Thermogram and Thermo-Gravimetric Analysis (TGA) Thermogram overlay of Form $S7_0$.
Figure 46:
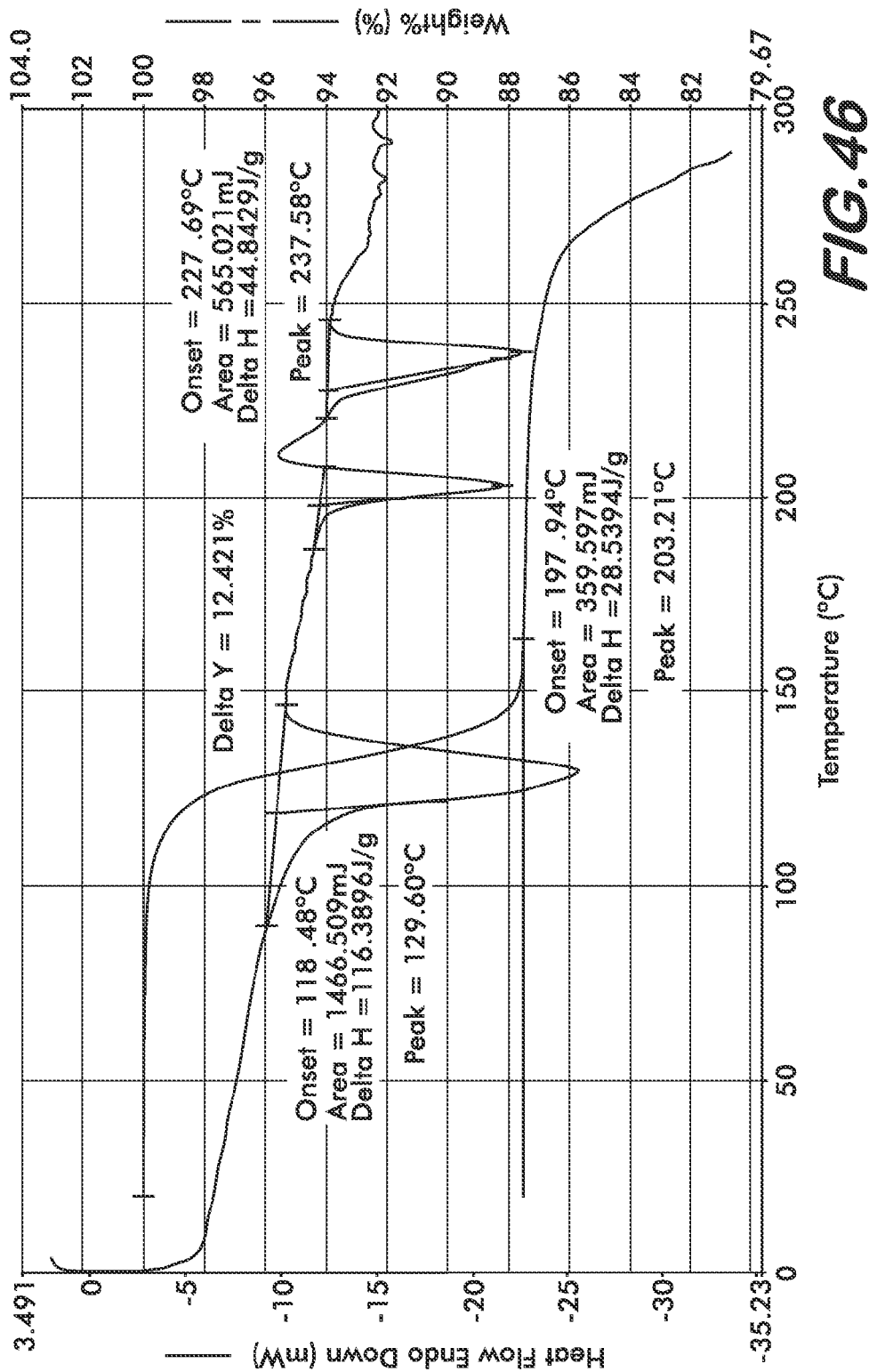
FIG. 46 is a Differential Scanning calorimetry (DSC) Thermogram and Thermo-Gravimetric Analysis (TGA) Thermogram overlay of Form $S9_0$.
Figure 47:
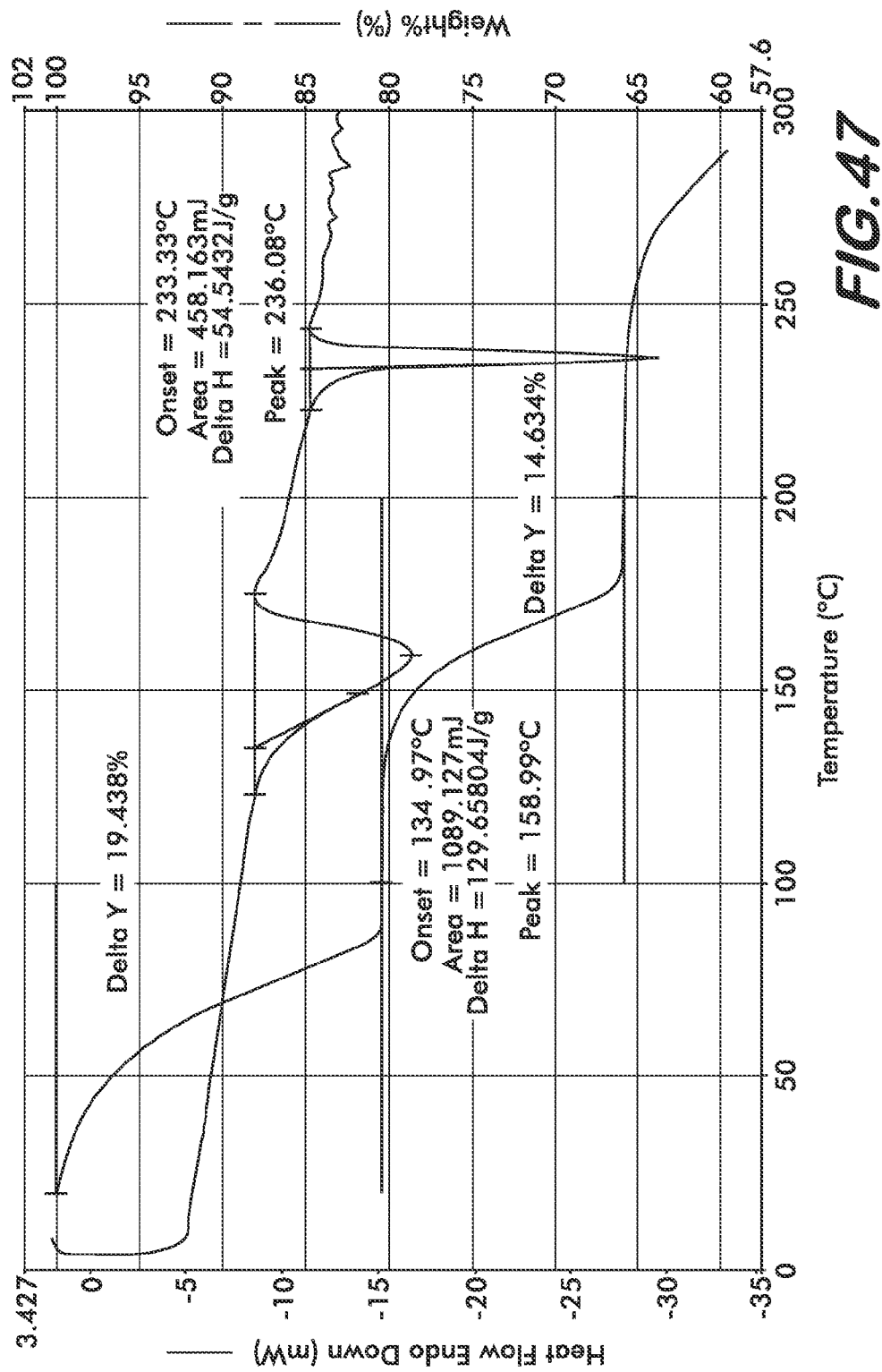
FIG. 47 is a Differential Scanning calorimetry (DSC) Thermogram and Thermo-Gravimetric Analysis (TGA) Thermogram overlay of Form $S10_0$.

Representative XRPD peaks for Form $HC_0$ are listed in the following Table 4. The X-Ray diffraction pattern characteristic of Form $HC_0$ is shown in FIG. 4.

TABLE 4

Form $HC_0$ XRPD peaks

| Peak No. | Angle [°2 Theta] | d-spacing [Angstrom] | Intensity [%] |
|---|---|---|---|
| 1 | 7.49 | 11.79 | 10.37 |
| 2 | 8.36 | 10.56 | 100 |
| 3 | 8.71 | 10.15 | 22.84 |
| 4 | 14.54 | 6.09 | 8.62 |
| 5 | 15.00 | 5.90 | 12.97 |
| 6 | 15.46 | 5.73 | 5.78 |
| 7 | 16.48 | 5.37 | 7.79 |
| 8 | 16.69 | 5.31 | 14.92 |
| 9 | 17.39 | 5.10 | 31.23 |
| 10 | 18.73 | 4.73 | 9.00 |
| 11 | 19.79 | 4.48 | 8.55 |
| 12 | 20.69 | 4.29 | 7.10 |
| 13 | 23.36 | 3.81 | 5.86 |
| 14 | 23.53 | 3.78 | 5.43 |
| 15 | 24.59 | 3.62 | 43.43 |
| 16 | 25.42 | 3.50 | 13.96 |
| 17 | 26.04 | 3.42 | 5.27 |

Representative XRPD peaks for Form $HD_0$ are listed in the following Table 5. The X-Ray diffraction pattern characteristic of Form $HD_0$ is shown in FIG. 5.

TABLE 5

Form $HD_0$ XRPD peaks

| Peak No. | Angle [°2 Theta] | d-spacing [Angstrom] | Intensity [%] |
|---|---|---|---|
| 1 | 7.60 | 11.62 | 100 |
| 2 | 8.99 | 9.83 | 5.05 |
| 3 | 15.16 | 5.84 | 11.66 |

Figure 6:
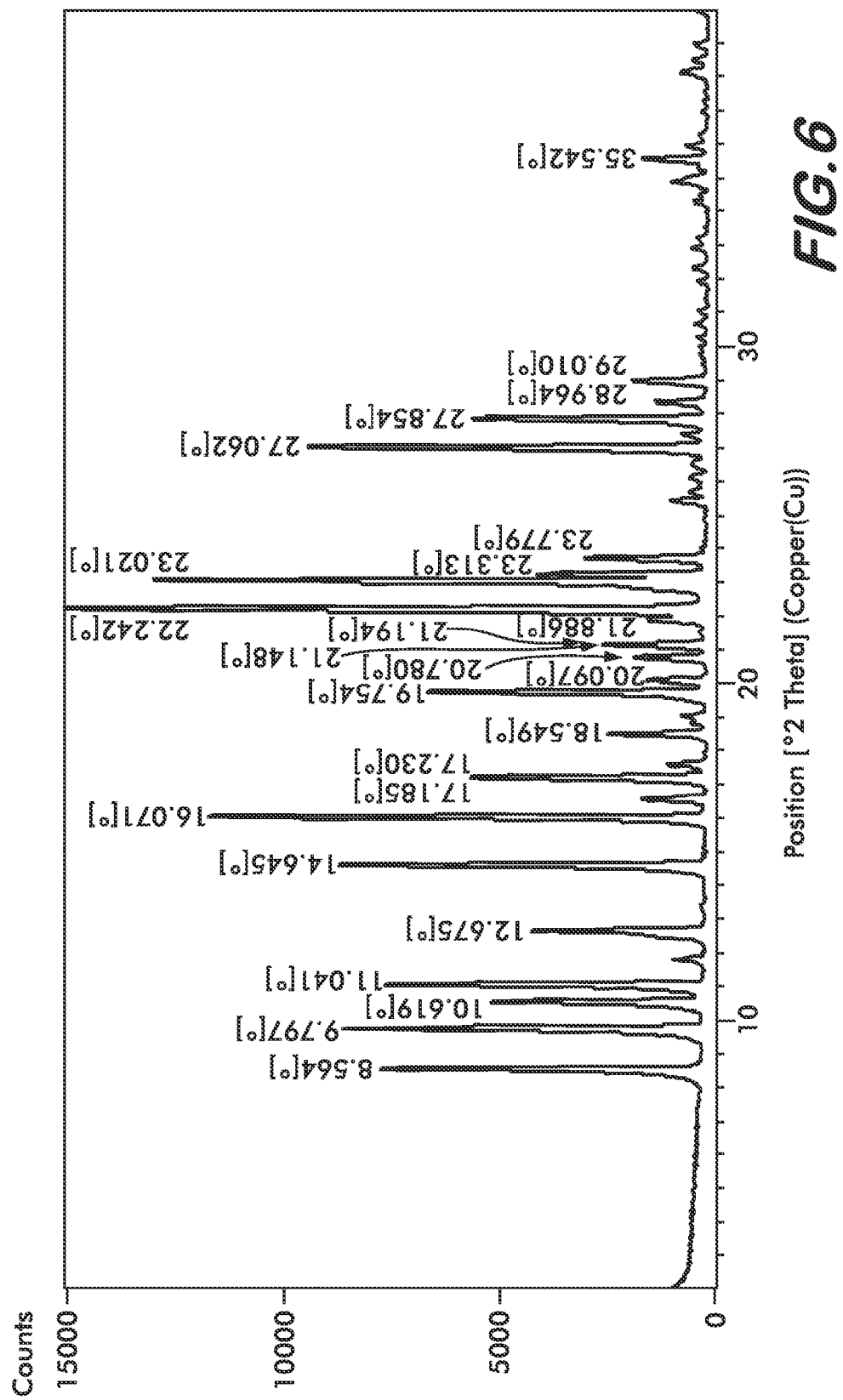
FIG. 6 is an X-ray Powder Diffractogram (XRPD) of Form $S2_0$.

Representative XRPD peaks for the $S2_0$ form are listed in the following Table 6. The X-Ray diffraction pattern characteristic of Form $S2_0$ is shown in FIG. 6.

TABLE 6

$S2_0$ form XRPD peaks

| Peak No. | Angle [°2 Theta] | d-spacing [Angstrom] | Intensity [%] |
|---|---|---|---|
| 1 | 8.56 | 10.32 | 58.9 |
| 2 | 9.80 | 9.02 | 58.8 |
| 3 | 10.62 | 8.32 | 26.8 |
| 4 | 11.04 | 8.01 | 54.2 |
| 5 | 12.68 | 6.98 | 31.8 |
| 6 | 14.64 | 6.04 | 61.0 |
| 7 | 16.07 | 5.51 | 81.0 |
| 8 | 17.18 | 5.16 | 37.5 |
| 9 | 17.23 | 5.14 | 43.7 |
| 10 | 19.75 | 4.49 | 50.9 |
| 11 | 22.24 | 3.99 | 100.0 |
| 12 | 23.02 | 3.86 | 99.5 |
| 13 | 23.31 | 3.81 | 22.8 |
| 14 | 27.06 | 3.29 | 55.8 |
| 15 | 27.85 | 3.20 | 42.6 |

Figure 7:
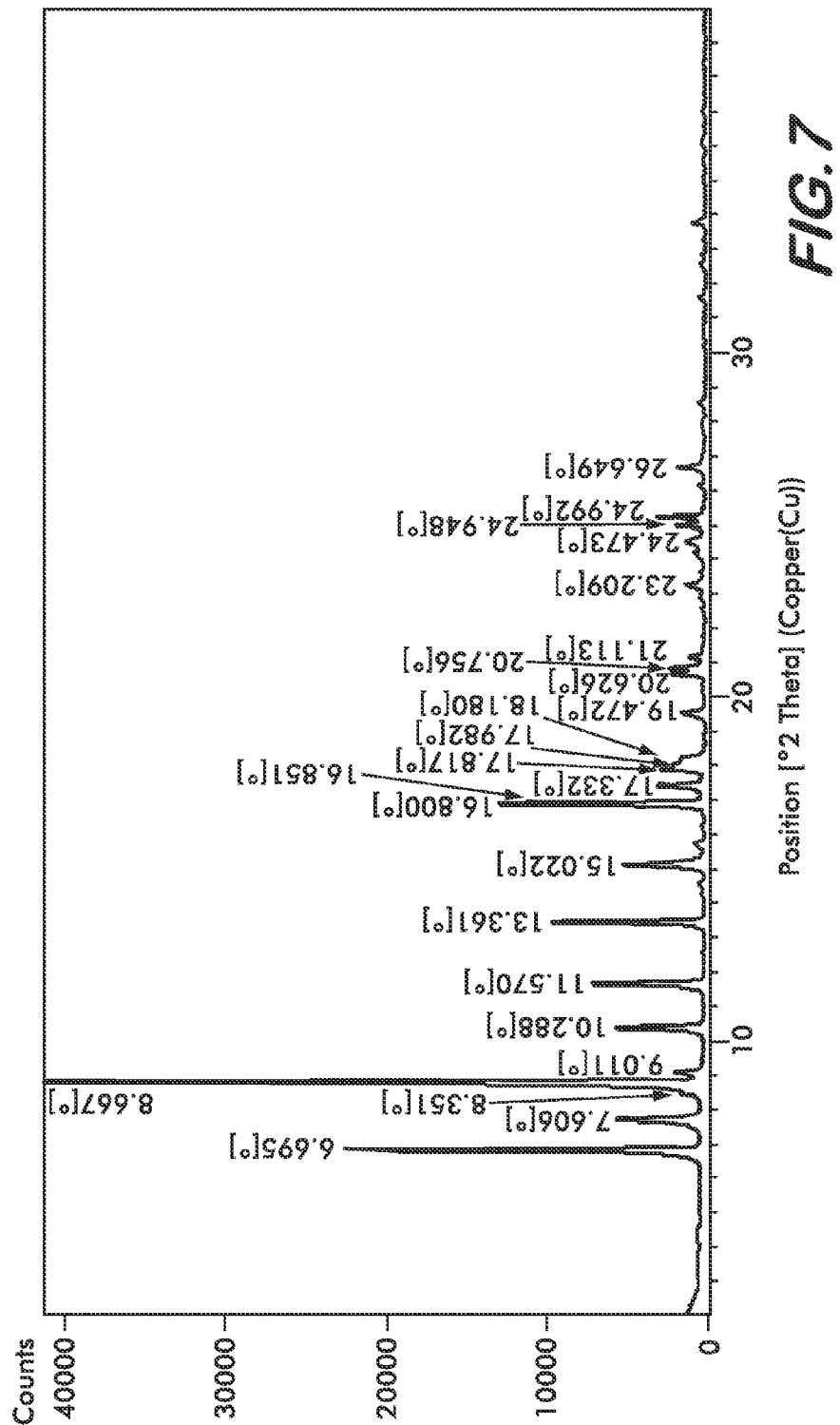
FIG. 7 is an X-ray Powder Diffractogram (XRPD) of Form $S3_0$.

Representative XRPD peaks for the $S3_0$ form are listed in the following Table 7. The X-Ray diffraction pattern characteristic of Form $S3_0$ is shown in FIG. 7.

TABLE 7

$S3_0$ form XRPD peaks

| Peak No. | Angle [°2 Theta] | d-spacing [Angstrom] | Intensity [%] |
|---|---|---|---|
| 1 | 6.70 | 13.19 | 54.7 |
| 2 | 7.61 | 11.61 | 12.5 |
| 3 | 8.67 | 10.19 | 100.0 |
| 4 | 10.29 | 8.59 | 13.3 |
| 5 | 11.57 | 7.64 | 16.7 |
| 6 | 13.36 | 6.62 | 23.3 |
| 7 | 15.02 | 5.89 | 11.7 |
| 8 | 16.80 | 5.27 | 30.8 |
| 9 | 16.85 | 5.26 | 22.1 |
| 10 | 17.33 | 5.11 | 7.1 |
| 11 | 25.20 | 3.53 | 7.1 |

Figure 8:
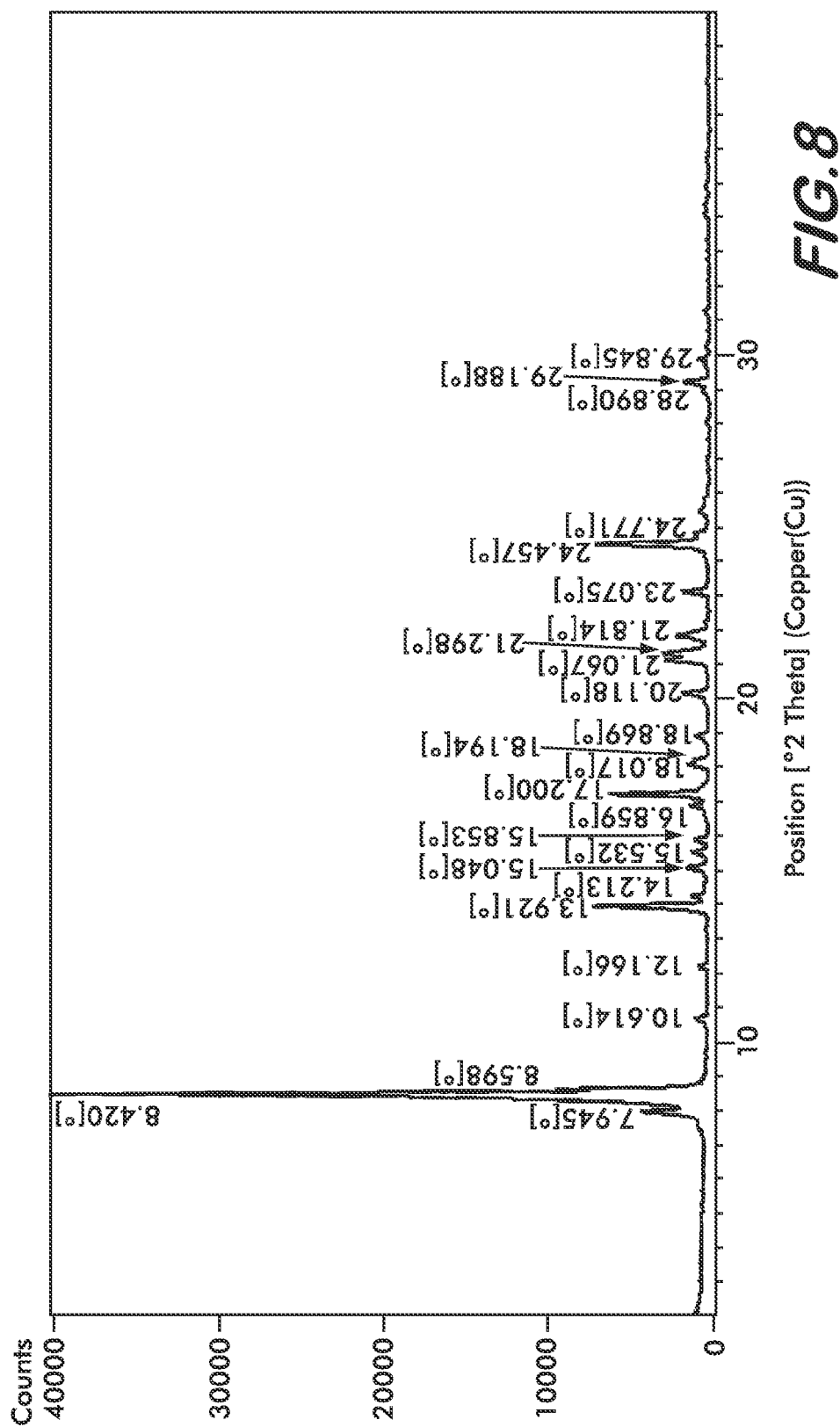
FIG. 8 is an X-ray Powder Diffractogram (XRPD) of Form $S4_0$.

Representative XRPD peaks for the $S4_0$ form are listed in the following Table 8. The X-Ray diffraction pattern characteristic of Form $S4_0$ is shown in FIG. 8.

TABLE 8

$S4_0$ form XRPD peaks

| Peak No. | Angle [°2 Theta] | d-spacing [Angstrom] | Intensity [%] |
|---|---|---|---|
| 1 | 7.95 | 11.12 | 9.3 |
| 2 | 8.42 | 10.49 | 100.0 |
| 3 | 8.60 | 10.28 | 21.9 |
| 4 | 13.92 | 6.36 | 17.4 |
| 5 | 17.20 | 5.15 | 14.1 |
| 6 | 21.07 | 4.21 | 5.9 |
| 7 | 21.30 | 4.17 | 6.4 |
| 8 | 24.46 | 3.64 | 17.3 |

Figure 9:
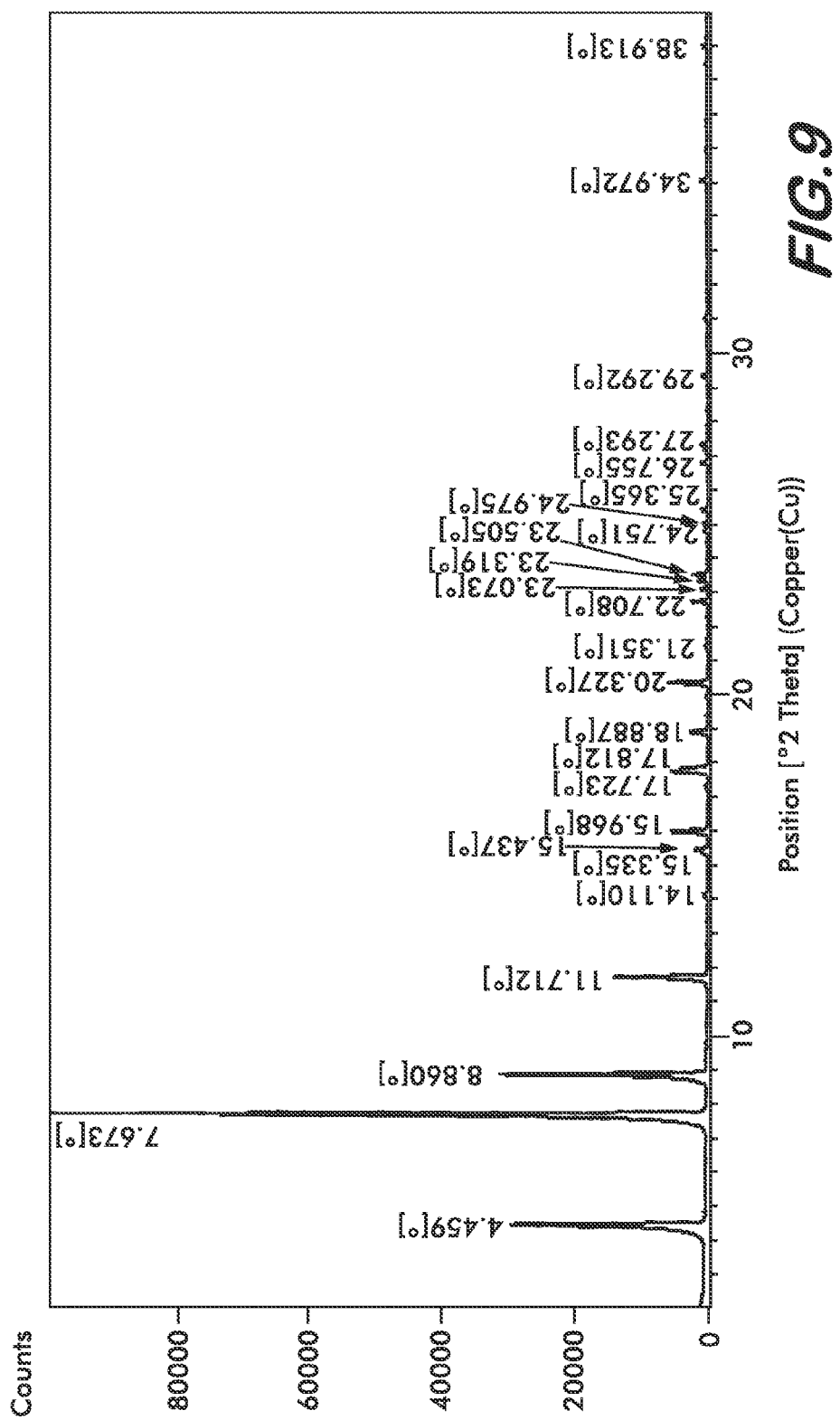
FIG. 9 is an X-ray Powder Diffractogram (XRPD) of Form $S5_0$.

Representative XRPD peaks for the $S5_0$ form are listed in the following Table 9. The X-Ray diffraction pattern characteristic of Form $S5_0$ is shown in FIG. 9.

TABLE 9

S5₀ form XRPD peaks

| Peak No. | Angle [°2 Theta] | d-spacing [Angstrom] | Intensity [%] |
|---|---|---|---|
| 1 | 4.46 | 19.80 | 28.9 |
| 2 | 7.67 | 11.51 | 100.0 |
| 3 | 8.86 | 9.97 | 31.3 |
| 4 | 11.71 | 7.55 | 14.5 |

Figure 10:
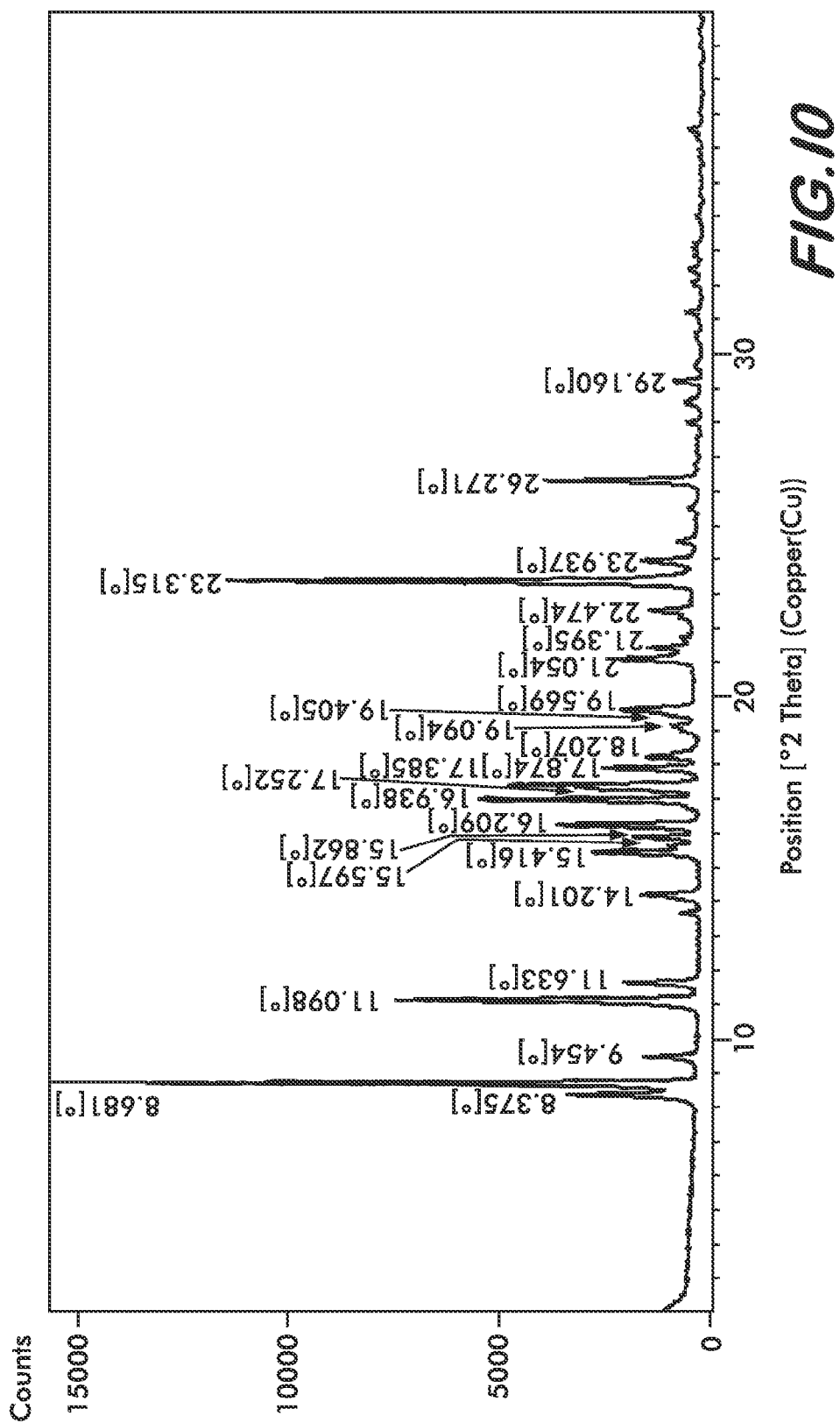
FIG. 10 is an X-ray Powder Diffractogram (XRPD) of Form $S6_0$.

Representative XRPD peaks for the S6₀ form are listed in the following Table 10. The X-Ray diffraction pattern characteristic of Form S6₀ is shown in FIG. 10.

TABLE 10

S6₀ form XRPD peaks

| Peak No. | Angle [°2 Theta] | d-spacing [Angstrom] | Intensity [%] |
|---|---|---|---|
| 1 | 8.36 | 10.57 | 19.7 |
| 2 | 8.68 | 10.18 | 100.0 |
| 3 | 11.10 | 7.97 | 46.3 |
| 4 | 15.42 | 5.74 | 15.7 |
| 5 | 16.21 | 5.46 | 21.6 |
| 6 | 16.94 | 5.23 | 33.2 |
| 7 | 17.25 | 5.14 | 14.7 |
| 8 | 17.39 | 5.10 | 29.0 |
| 9 | 23.31 | 3.81 | 71.4 |
| 10 | 26.27 | 3.39 | 23.7 |

Figure 11:
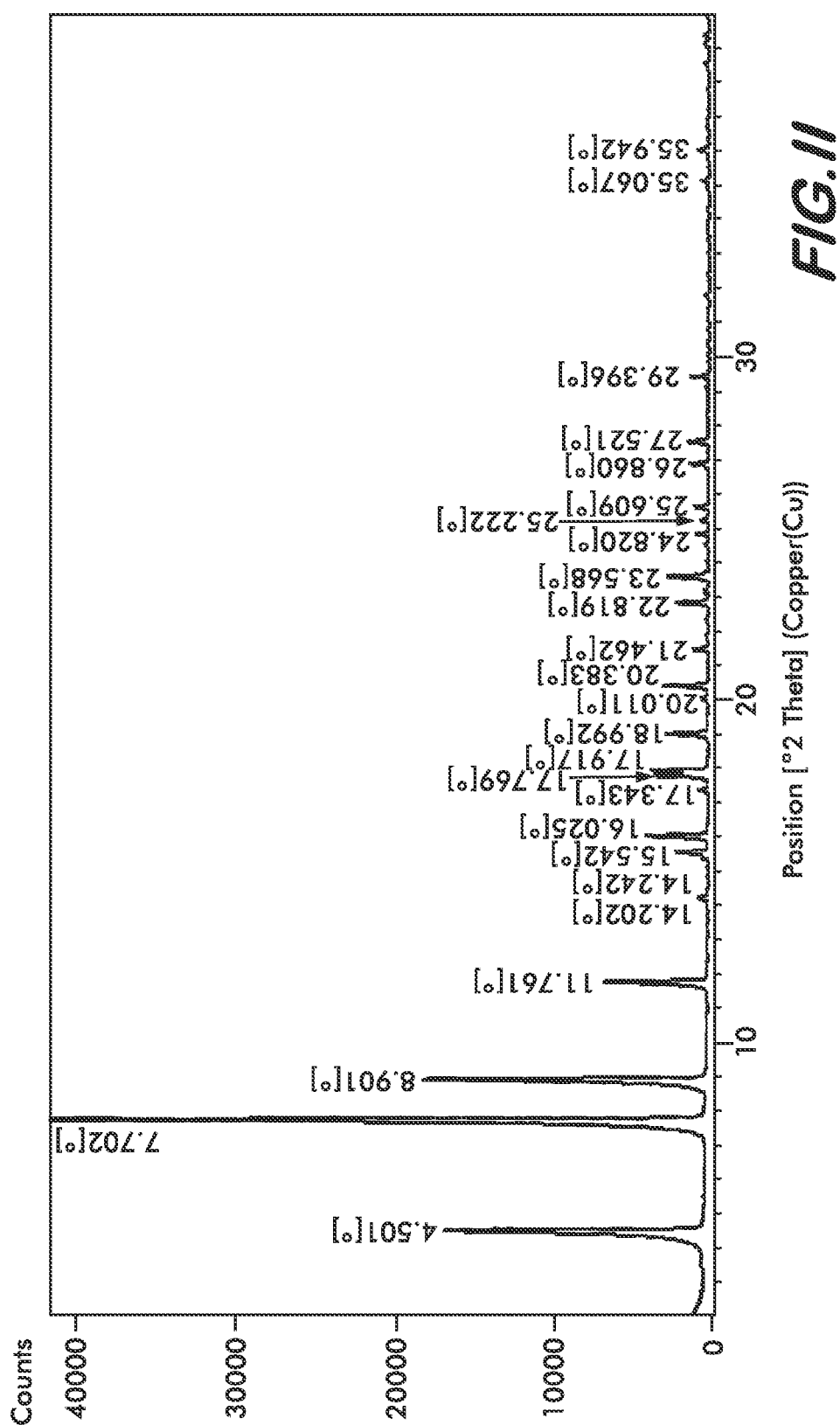
FIG. 11 is an X-ray Powder Diffractogram (XRPD) of Form $S7_0$.

Representative XRPD peaks for the S7₀ form are listed in the following Table 11. The X-Ray diffraction pattern characteristic of Form S7₀ is shown in FIG. 11.

TABLE 11

S7₀ form XRPD peaks

| Peak No. | Angle [°2 Theta] | d-spacing [Angstrom] | Intensity [%] |
|---|---|---|---|
| 1 | 4.50 | 19.62 | 35.4 |
| 2 | 7.70 | 11.47 | 100.0 |
| 3 | 8.90 | 9.93 | 42.3 |
| 4 | 11.76 | 7.52 | 15.6 |

Figure 12:
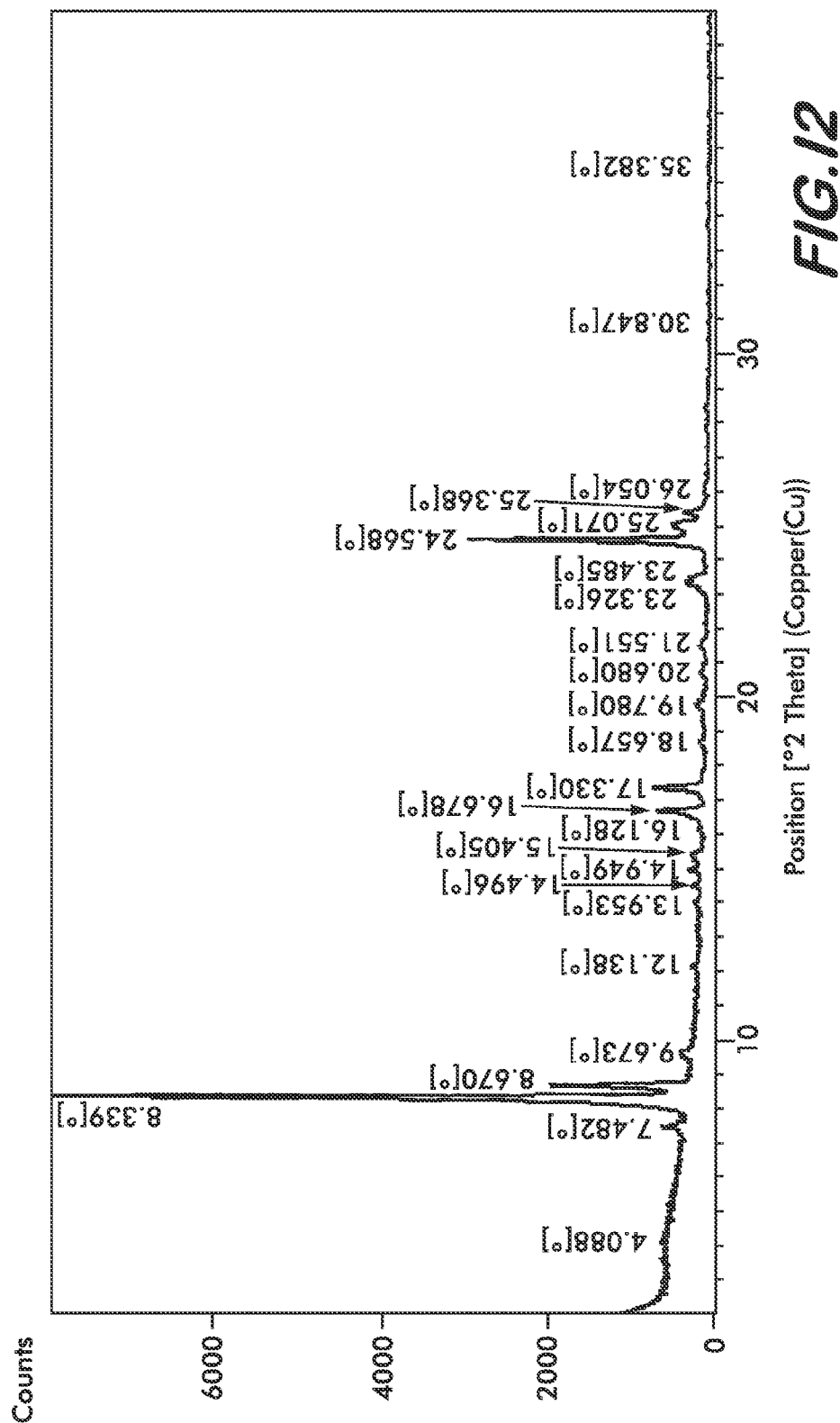
FIG. 12 is an X-ray Powder Diffractogram (XRPD) of Form $S9_0$.

Representative XRPD peaks for the S9₀ form are listed in the following Table 12. The X-Ray diffraction pattern characteristic of Form S9₀ is shown in FIG. 12.

TABLE 12

S9₀ form XRPD peaks

| Peak No. | Angle [°2 Theta] | d-spacing [Angstrom] | Intensity [%] |
|---|---|---|---|
| 1 | 8.34 | 10.59 | 100.0 |
| 2 | 8.67 | 10.19 | 23.0 |
| 3 | 16.68 | 5.31 | 7.2 |
| 4 | 17.33 | 5.11 | 8.5 |
| 5 | 24.57 | 3.62 | 39.3 |

Figure 13:
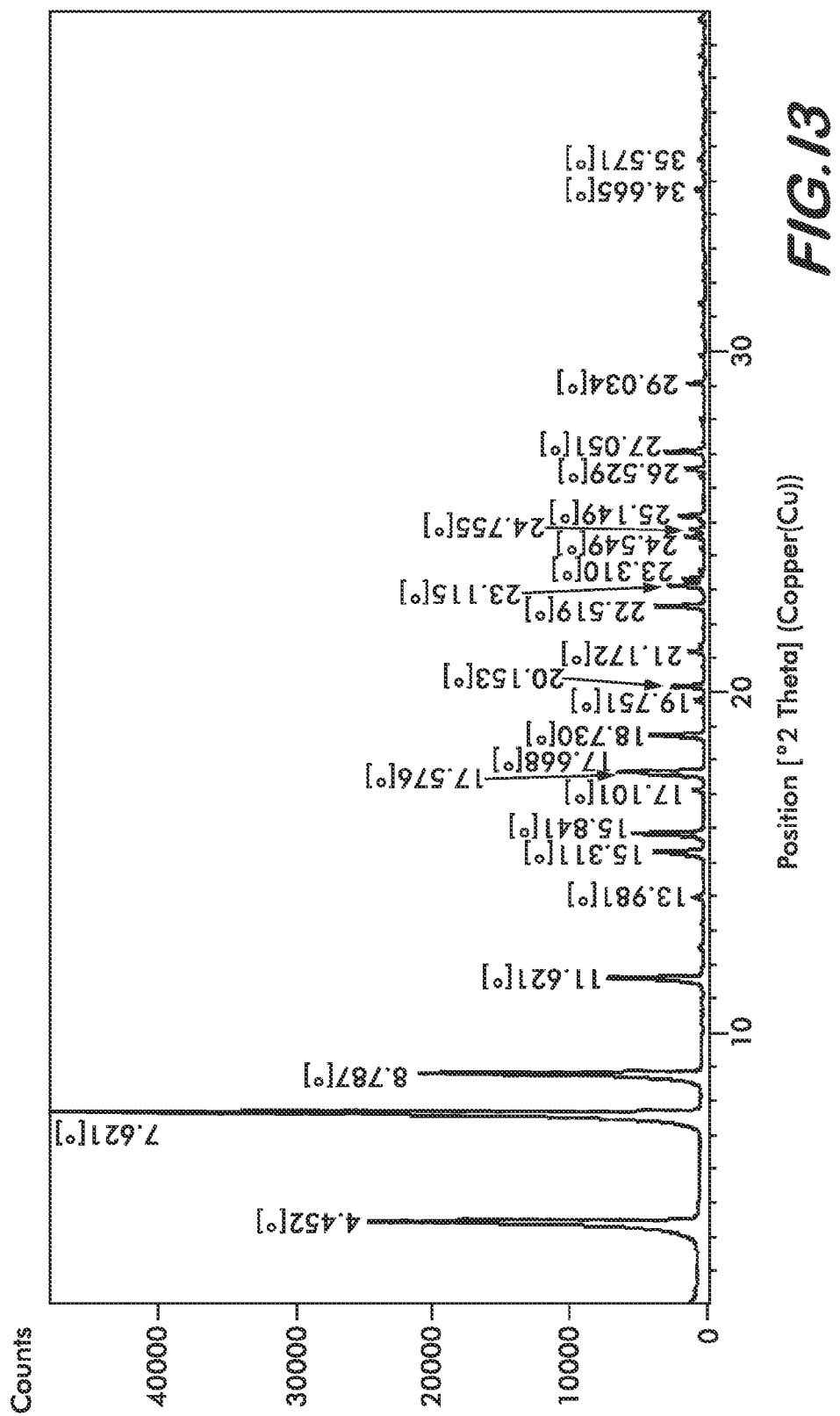
FIG. 13 is an X-ray Powder Diffractogram (XRPD) of Form $S10_0$.

Representative XRPD peaks for the S10₀ form are listed in the following Table 13. The X-Ray diffraction pattern characteristic of Form S10₀ is shown in FIG. 13.

TABLE 13

S10₀ form XRPD peaks

| Peak No. | Angle [°2 Theta] | d-spacing [Angstrom] | Intensity [%] |
|---|---|---|---|
| 1 | 4.45 | 19.83 | 42.6 |
| 2 | 7.62 | 11.59 | 100.0 |

TABLE 13-continued

S10₀ form XRPD peaks

| Peak No. | Angle [°2 Theta] | d-spacing [Angstrom] | Intensity [%] |
|---|---|---|---|
| 3 | 8.79 | 10.06 | 43.4 |
| 4 | 11.62 | 7.61 | 14.7 |
| 5 | 15.84 | 5.59 | 11.3 |
| 6 | 17.67 | 5.02 | 12.9 |

Figure 14:
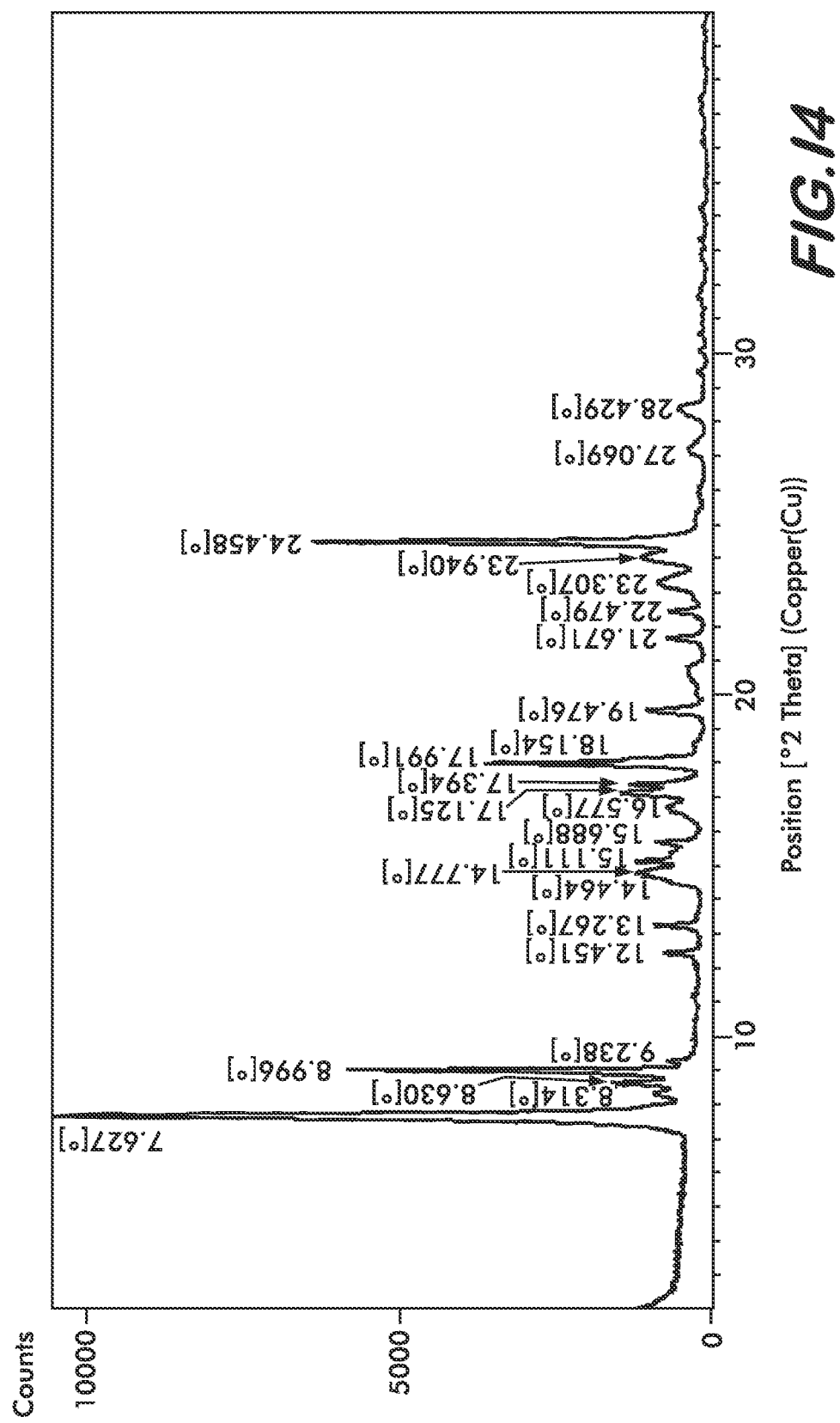
FIG. 14 is an X-ray Powder Diffractogram (XRPD) of Form $S12_0$.
Figure 15:
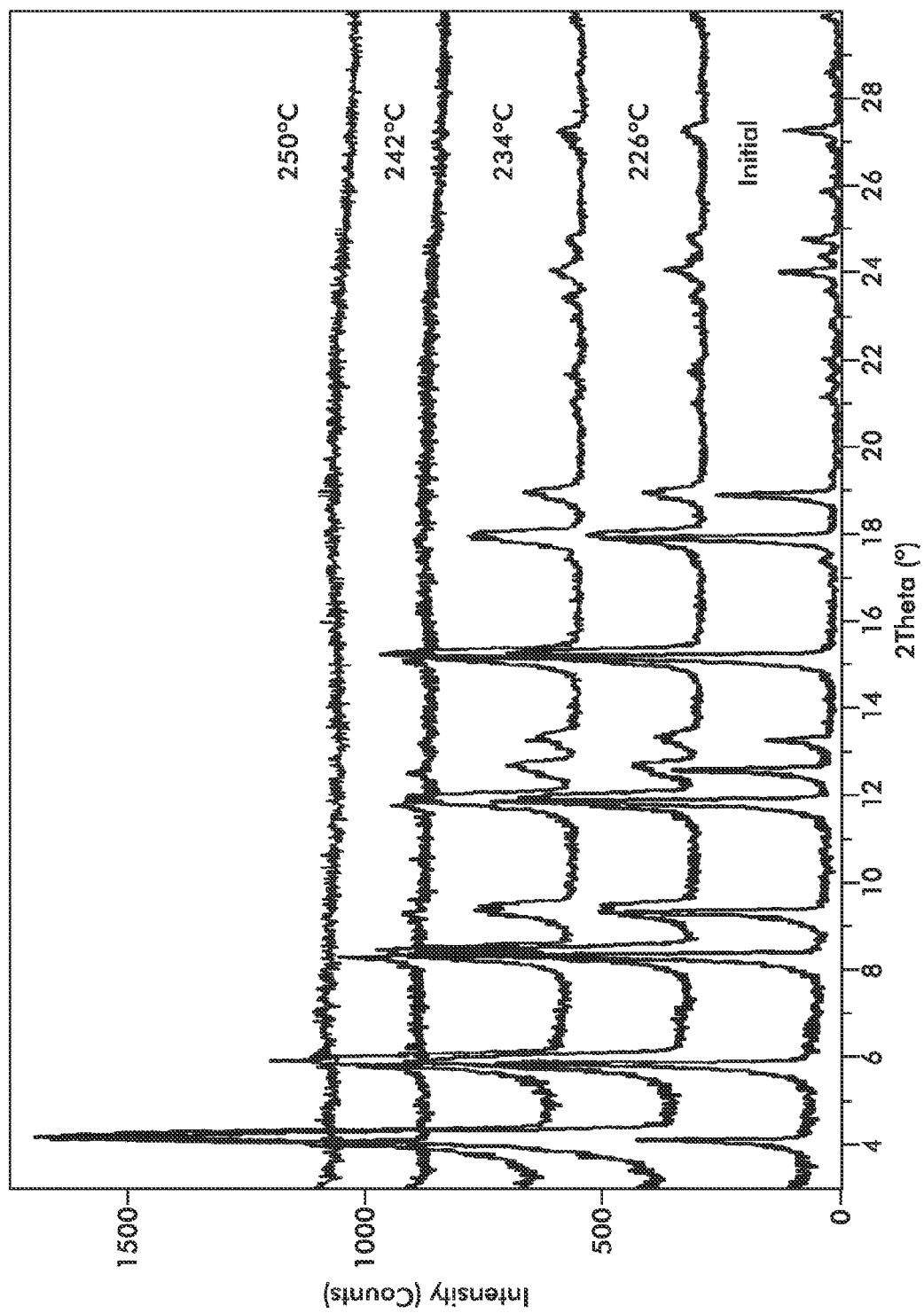
FIG. 15 is a Variable Temperature X-ray Powder Diffractogram (VT-XRPD) of Form $A_0$.
Figure 16:
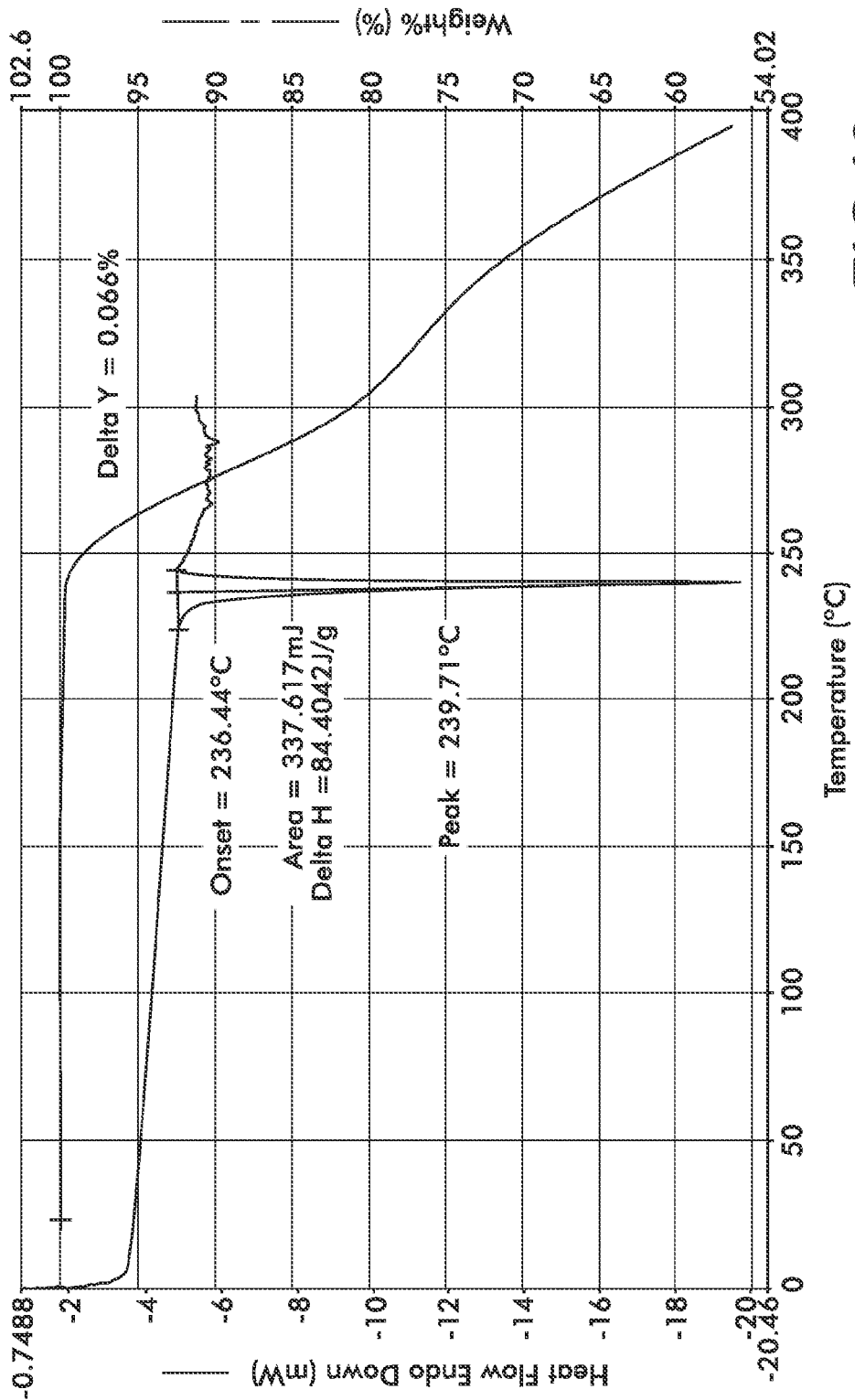
FIG. 16 is a Differential Scanning calorimetry (DSC) Thermogram and Thermo-Gravimetric Analysis (TGA) Thermogram overlay of Form $A_0$.
Figure 17:
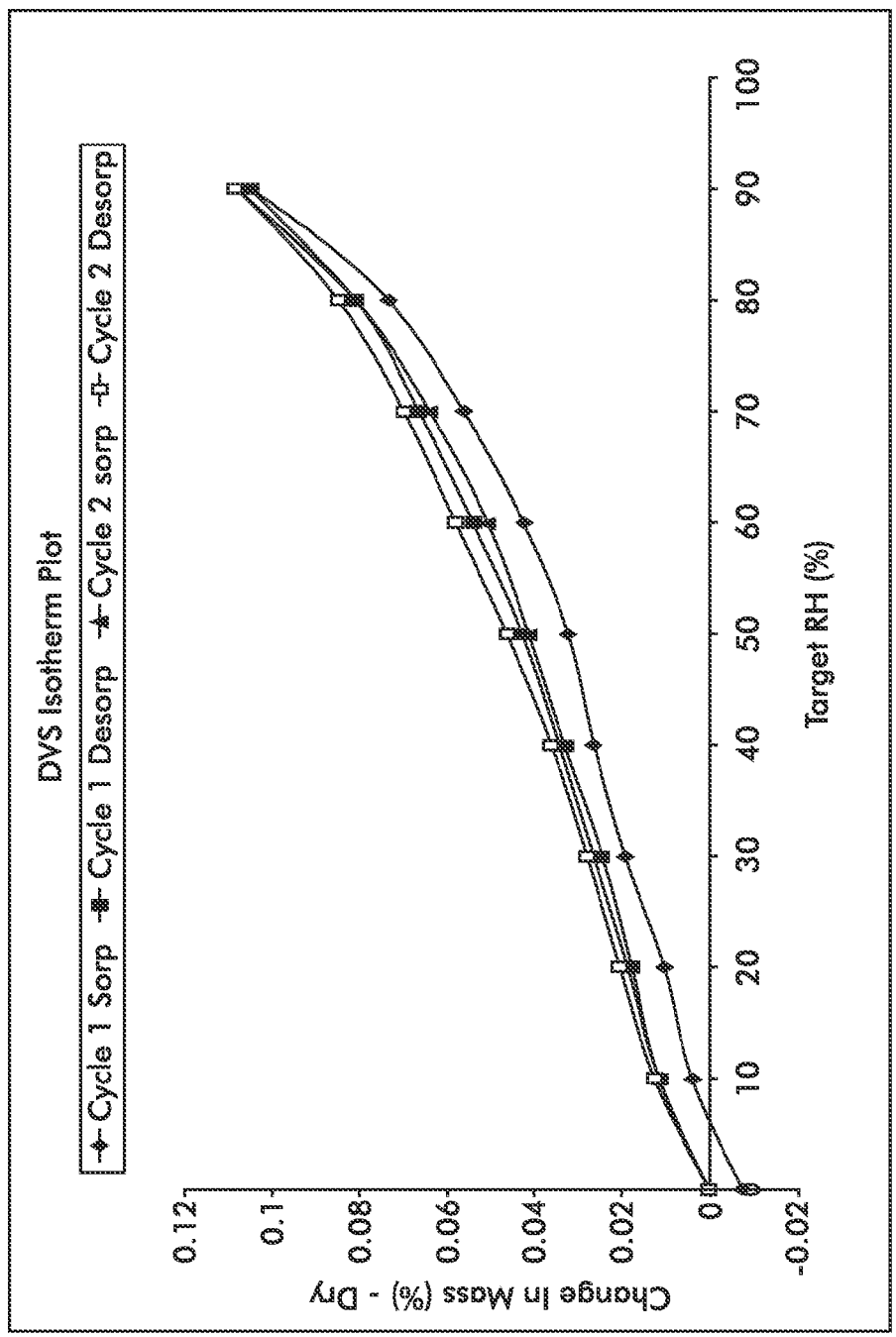
FIG. 17 is a Dynamic Vapor Sorption (DVS) regular isotherm plot of Form $A_0$.

Representative XRPD peaks for the S12₀ form are listed in the following Table 14. The X-Ray diffraction pattern characteristic of Form S12₀ is shown in FIG. 14.

TABLE 14

S12₀ form XRPD peaks

| Peak No. | Angle [°2 Theta] | d-spacing [Angstrom] | Intensity [%] |
|---|---|---|---|
| 1 | 7.63 | 11.58 | 100 |
| 2 | 7.67 | 11.51 | 92 |
| 3 | 8.63 | 10.24 | 12 |
| 4 | 9.00 | 9.82 | 55 |
| 5 | 14.78 | 5.99 | 10 |
| 6 | 17.13 | 5.17 | 12 |
| 7 | 17.39 | 5.09 | 11 |
| 8 | 17.99 | 4.93 | 33 |
| 9 | 18.15 | 4.88 | 10 |
| 10 | 24.46 | 3.64 | 60 |

Accordingly, in one aspect, the present invention pertains to a crystalline form of Compound I that is Form A₀, Form B₀, or a mixture thereof. In a further aspect, the crystalline form is Form A₀. In another aspect, the crystalline form is Form B₀. In a further aspect, the crystalline form is characterized by an X-ray powder diffraction pattern comprising one or more of the following peaks: 4.32, 6.07, 8.55, 12.07 and/or 15.37±0.2 degrees 2-theta. In yet another aspect, the crystalline form has an X-ray powder diffraction pattern substantially as depicted in FIG. 1. In an additional aspect, the crystalline form is characterized by an X-ray powder diffraction pattern comprising one or more of the following peaks: 7.16, 7.89, 10.77, 16.54, and/or 21.20±0.2 degrees 2-theta. In still another aspect, the crystalline form has an X-ray powder diffraction pattern substantially as depicted in FIG. 2.

A further aspect of the present invention pertains to a crystalline form of Compound I that is Form HA₀, Form HC₀, Form HD₀ or a mixture thereof. In another aspect, the crystalline form is Form HA₀. In a further aspect, the crystalline form is Form HC₀. In an additional aspect, the crystalline form is Form HD₀. In still another aspect, the crystalline form is characterized by an X-ray powder diffraction pattern comprising one or more of the following peaks: 7.59, 15.12, 16.06, 17.94 and/or 23.89±0.2 degrees 2-theta. In a further aspect, the crystalline form has an X-ray powder diffraction pattern substantially as depicted in FIG. 3. In an additional aspect, the crystalline form is characterized by an X-ray powder diffraction pattern comprising one or more of the following peaks: 8.36, 8.71, 16.69, 17.39 and/or 24.59±0.2 degrees 2-theta. In yet another aspect, the crystalline form has an X-ray powder diffraction pattern substantially as depicted in FIG. 4. In another aspect, the crystalline form is characterized by an X-ray powder diffraction pattern comprising one or more of the following peaks: 7.60, 8.99 and/or 15.16±0.2 degrees 2-theta. In a further aspect, the crystalline form has an X-ray powder diffraction pattern substantially as depicted in FIG. 5.

Still another aspect of the present invention pertains to a crystalline form of Compound I that is Form S2₀, Form S3₀, Form S4₀, Form S5₀, Form S6₀, Form S7₀, Form S9₀, Form S10$_0$, Form S12$_0$ or a mixture thereof. In a further aspect, the crystalline form is Form S2$_0$. In still another aspect, the crystalline form is Form S3$_0$. In an additional aspect, the crystalline form is Form S4$_0$. In yet a further aspect, the crystalline form is Form S5$_0$. In still an additional aspect, the crystalline form is Form S6$_0$. In another aspect, the crystalline form is Form S7$_0$. In a further aspect, the crystalline form is Form S9$_0$. In still another aspect, the crystalline form is Form S10$_0$. In a further aspect, the crystalline form is Form S12$_0$. In a further aspect, the crystalline form is characterized by an X-ray powder diffraction pattern comprising one or more of the following peaks: 8.56, 14.64, 16.07, 22.24 and/or 23.02±0.2 degrees 2-theta. In yet another aspect, the crystalline form is characterized by an X-ray powder diffraction pattern comprising one or more of the following peaks: 6.70, 8.67, 13.36, 16.80 and/or 16.85±0.2 degrees 2-theta. In an additional aspect, the crystalline form is characterized by an X-ray powder diffraction pattern comprising one or more of the following peaks: 8.42, 8.60, 13.92, 17.20 and/or 24.46±0.2 degrees 2-theta. In another aspect, the crystalline form is characterized by an X-ray powder diffraction pattern comprising one or more of the following peaks: 4.46, 7.67, 8.86 and/or 11.71±0.2 degrees 2-theta. In an additional aspect, the crystalline form is characterized by an X-ray powder diffraction pattern comprising one or more of the following peaks: 8.68, 11.10, 16.94, 17.39 and/or 23.31±0.2 degrees 2-theta. In another aspect, the crystalline form is characterized by an X-ray powder diffraction pattern comprising one or more of the following peaks: 4.50, 7.70, 8.90 and/or 11.76±0.2 degrees 2-theta. In still another aspect, the crystalline form is characterized by an X-ray powder diffraction pattern comprising one or more of the following peaks: 8.34, 8.67, 16.68, 17.33 and/or 24.57±0.2 degrees 2-theta. In an additional aspect, the crystalline form is characterized by an X-ray powder diffraction pattern comprising one or more of the following peaks: 4.45, 7.62, 8.79, 11.62 and/or 17.67±0.2 degrees 2-theta. In another aspect, the crystalline form is characterized by an X-ray powder diffraction pattern comprising one or more of the following peaks: 7.63, 7.67, 9.00, 17.99 and 24.46±0.2 degrees 2-theta.

An additional aspect of the present invention pertains to a process for preparing a crystalline form of Compound I that is Form A$_0$, comprising the steps of: (a) slurrying Compound I in hydrocarbons (such as heptane or toluene); (b) cooling the resulting slurry; (c) filtering the resulting slurry; and (d) drying the filter-cake. In one aspect, Compound I is slurried in 26 to 45 volumes of heptane. In another aspect, Compound I is slurried in 45 volumes of heptane. In an additional aspect, step (a) is performed at 79 to 83° C. In still another aspect, step (a) is performed at 85° C. In yet another aspect, step (a) is performed for 24 to 48 hours. In a further aspect, step (a) is performed for 45 hours. In another aspect, step (b) occurs at a temperature of 30-65° C.

In still another aspect, step (b) is performed at 65° C. In an additional aspect, step (d) is performed at room temperature for 0.33 to 3 hours. In still another aspect, step (d) is performed at room temperature for three hours.

A further aspect of the present invention pertains to a process for preparing a crystalline form of Compound I that is Form A$_0$, comprising the steps of: (a) dissolving Compound I in a solvent; (b) filtering the resulting solution; (c) partially distilling the solvent while adding an anti-solvent to precipitate Compound I; (d) further distilling the resulting slurry while adding additional anti-solvent to reduce the volume of the solvent used in step (a); (e) heating the slurry to achieve complete conversion to Form A$_0$; (f) cooling; (g) collecting the product via filtration; and (h) drying. In a further aspect, step (a) is performed using 27 to 35 volumes of THF. In another aspect, step (a) is performed using 30 volumes of THF. In a further aspect, the solution produced via step (a) may optionally be treated with a metal scavenger or carbon. In still a further aspect, the filtering step (b) comprises one or both of the following steps: (i) filtering to remove the metal scavenger; and (ii) polish filtering through a 1-micron inline cartridge filter. In a further aspect, the solvent present in step (c) is distilled to 60 to 90% of its original volume. In an additional aspect, step (c) is performed using a hydrocarbon (such as heptane) as the anti-solvent. In another aspect, step (d) is performed until less than 5% THF by volume remains. In still another aspect, step (e) is performed at a temperature of about 90 to 96° C. In an additional aspect, step (e) may be optionally omitted. In another aspect, the slurry is agitated for about 3 to 5 hours. In a further aspect, step (f) is performed at ambient temperature (25±5° C.). In an additional aspect, the filtration of step (g) is performed using a dry, inert gas. In another aspect, step (h) is performed at a temperature up to 80° C. In yet another aspect, the residual water and/or solvate(s) are azeotropically removed.

Yet another aspect of the present invention pertains to a pharmaceutical composition comprising Form A$_0$, Form B$_0$, Form HA$_0$, Form HC$_0$ or Form HD$_0$, or a mixture thereof A further aspect pertains to a method of treating cancer comprising the step of administering to a patient in need thereof a therapeutically effective amount of a pharmaceutical composition comprising Form A$_0$, Form B$_0$, Form HA$_0$, Form HC$_0$ or Form HD$_0$ or a mixture thereof. In an additional aspect, the present invention pertains to a method of treating cancer comprising the step of administering to a patient in need thereof a therapeutically effective amount of a pharmaceutical composition comprising Form A$_0$.

TERMINOLOGY

The term "amorphous," as used herein, means lacking a characteristic crystal shape or crystalline structure.

The term "anti-solvent," as used herein, means a solvent in which a compound is substantially insoluble.

The term "crystalline," as used herein, means having a regularly repeating arrangement of molecules or external face planes.

The term "crystalline form," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and de-solvated solvates.

The term "polymorphic" or "polymorphism" is defined as the possibility of at least two different crystalline arrangements for the same chemical molecule.

The term "solute" as used herein, refers to a substance dissolved in another substance, usually the component of a solution present in the lesser amount.

The term "solution," as used herein, refers to a mixture containing at least one solvent and at least one compound at least partially dissolved in the solvent.

The term "solvate," as used herein, refers to a crystalline material that contains solvent molecules within the crystal structure.

The term "solvent," as used herein, means a substance, typically a liquid, that is capable of completely or partially dissolving another substance, typically a solid. Solvents for the practice of this invention include, but are not limited to, water, acetic acid, acetone, acetonitrile (ACN), benzyl alcohol, 1-butanol, 2-butanol, 2-butanone, butyronitrile, tert-butanol, N-butyl acetate, chlorobenzene, chloroform, cyclohexane, 1-2 dichloloroethane (DCE), dichloromethane (DCM), diethylene glycol dibutyl ether (DGDE), diisopropyl amine (DIPA), diisopropyl ether (DIPE), 1,2-dimethoxyethane (DE), N,N-dimethylacetamide (DMA), 4-dimethylaminopyridine (DMAP), N,N-dimethylformamide (DMF), dimethyl sulfoxide, 1,4-dioxane, ethyleneglycoldiemethylether, ethanol, ethyl acetate, ethyldiisopropylamine, ethylene glycol, ethyl formate, formic acid, heptane, isobutyl alcohol, isopropyl acetate (IPAC), isopropyl alcohol (IPA), isopropyl amine, lithium diisopropylamide (LDA), methanol, methoxy benzene (MTB), methyl acetate, methyl ethyl ketone (MEK), methyl isobutyl ketone (MIK), 2-methyltetrahydrofuran, methyl tert-butyl ether (MTBE), 1:1 formamide:water, 1:1 N-methylpyrrolidinone (NMP): water, 2-pentanone, 3-pentanone, 1-pentanol, 1,2-propanediol, 2-propanol (IPA), 1-propanol, propanonitrile, propylene carbonate, 1,2-propylene glycol (PG), pyridine, tetrahydrofuran (THF), tetrahydropyran (THP), toluene, triethyl amine, xylene, mixtures thereof and the like. These solvents are categorized into five classes according to their functional group: Class 1: "Protic" or hydrogen bond donating solvents (Lewis acids), including benzyl alcohol, ethanol, IPA, methanol, and water; Class 2: Hydrogen bonding acceptor solvents (Lewis bases), including acetone, 1,4-dioxane, DMF, ethyl acetate, MEK, MTBE, THF, and water; Class 3: Polar aprotic solvents, better termed "nonhydroxylic solvents," including acetonitrile, DMA, DMF, and DMSO; Class 4: Chlorocarbon solvents, which include chloroform; Class 5: Hydrocarbon solvents, both saturated and unsaturated, including n-heptane, toluene, p-xylene, and xylene.

The term "therapeutically effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the crystalline forms would be administered at lower dosage levels, with a gradual increase until the desired effect is achieved.

Unless stated otherwise, percentages stated throughout this specification are weight/weight (w/w) percentages.

The term "pharmaceutically acceptable excipients," as used herein, includes any and all solvents, dispersion media, coatings, antibacterial and antifungal agents, isotonic and absorption delaying agents and the like. The use of such media and agents for pharmaceutical active substances is well known in the art, such as in *Remington: The Science and Practice of Pharmacy*, 20th ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

For therapeutic purposes, the crystalline forms of the present invention can be administered by any means that results in the contact of the active agent with the agent's site of action in the body of the subject. The crystalline forms may be administered by any conventional means available for use in conjunction with pharmaceuticals, either as individual therapeutic agents or in combination with other therapeutic agents, such as, for example, analgesics. The crystalline forms of the present invention are preferably administered in therapeutically effective amounts for the treatment of the diseases and disorders described herein to a subject in need thereof.

In therapeutic or prophylactic use, the crystalline forms of the present invention may be administered by any route that drugs are conventionally administered. Such routes of administration include intraperitoneal, intravenous, intramuscular, subcutaneous, intrathecal, intracheal, intraventricular, oral, buccal, rectal, parenteral, intranasal, transdermal or intradermal. Administration may be systemic or localized.

The crystalline forms described herein may be administered in pure form, combined with other active ingredients, or combined with pharmaceutically acceptable nontoxic excipients or carriers. Oral compositions will generally include an inert diluent carrier or an edible carrier. Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings.

Alternative preparations for administration include sterile aqueous or nonaqueous solutions, suspensions, and emulsions. Examples of nonaqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

Preferred methods of administration of the crystalline forms to mammals include intraperitoneal injection, intramuscular injection, and intravenous infusion. Various liquid formulations are possible for these delivery methods, including saline, alcohol, DMSO, and water based solutions. The concentration may vary according to dose and volume to be delivered and can range from about 1 to about 1000 mg/mL. Other constituents of the liquid formulations can include preservatives, inorganic salts, acids, bases, buffers, nutrients, vitamins, or other pharmaceuticals such as analgesics or additional PARP and kinase inhibitors.

Instrumentation

X-Ray Powder Diffraction (XRPD)

XRPD patterns were recorded on a PANalytical X' Pert Pro diffractometer using Cu Kα radiation at 40 kV and 40 mA. A silicon standard was run to check the x-ray tube alignment.

The sample was pressed onto a zero-background quartz plate in an aluminum holder. The standard X-ray powder pattern scans were collected from ca. 2 to 40° 2θ with a 0.0080° step size and 96.06 sec counting time which resulted in a scan rate of approximately 0.5°/min.

For the single crystal studies, the crystals chosen were coated with paratone oil and flash frozen on an Oxford diffraction CCD diffractometer (Xcalibur S, with a Sapphire detector). Data were collected with standard area detector techniques. The structures were solved and refined with the SHELXTL package. Default Reitveld refinement of the single crystal parameters against the measured XRPD pattern gave a good fit with no unexplained peaks.

Variable Temperature X-Ray Powder Diffraction (VT-XRPD)

Variable temperature studies were performed under a nitrogen atmosphere with an Anton Paar TTK450 temperature chamber under computer control through an Anton Paar TCU100 temperature control unit. Two measurement schemes were used, restricted and continuous. In the restricted mode, measurements were made, only after the TK450 chamber reached the requested temperature. In the continuous mode, the sample was heated at 10° C./minute and fast scans were measured as the temperature changed. After the requested temperature was reached, the sample was cooled at 30 or 35° C./minute and a slower scan measured 25° C. The temperatures chosen were based on DSC results.

Differential Scanning Calorimetry (DSC)

Thermal curves were acquired using a Perkin-Elmer Sapphire DSC unit equipped with an autosampler running Pyris software version 6.0 calibrated with indium prior to analysis. Solid samples of 1-11 mg were weighed into 20 μL aluminum open sample pans. The DSC cell was then purged with nitrogen and the temperature heated from 0° to 275° C. at 10° C./min.

Thermogravimetric Analysis (TGA)

Thermal curves were acquired using a Perkin-Elmer Pyris 1 TGA unit running Pyris software version 6.0 calibrated with calcium oxalate monohydrate. TGA samples between 1-15 mg were monitored for percent weight loss as heated from 25° to 400° C. at 10° C./min in a furnace purged with helium at ca. 50 mL/min.

Dynamic Vapor Sorption (DVS)

Gravimetric vapor sorption experiments were carried out using the DVS-HT instrument (Surface Measurement Systems, London, UK). This instrument measures the uptake and loss of vapor gravimetrically using a recording ultra-microbalance with a mass resolution of ±0.1 μg. The vapor partial pressure (±1.0%) around the sample was controlled by mixing saturated and dry carrier gas streams using electronic mass flow controllers. The desired temperature was maintained at ±0.1° C.

The samples (10-25 mg) were placed into the DVS-HT instrument at the desired temperature. Two types of dynamic vapor sorption experiments were performed:
1. The sample was initially dried in stream of dry air (<0.1% relative humidity (RH)) for 20 hours to establish a dry mass and exposed to two 0-90% RH cycles (in 10% RH increments).
2. The sample was exposed at 90% RH for 20 hours and exposed to two 90-0% RH cycles (in 10% RH increments).

Infrared Spectrometry (FTIR)

Spectra were obtained using a Thermo Electron-Nicolet Avatar 370 DTGS instrument with the Smart Orbit ATR attachment containing a diamond crystal window. Thermo Electron Omnic™ software (version 3.1) was used to compute the spectrum from 4000 to 400 cm$^{-1}$ from the initial interferogram. A background scan was collected before obtaining each sample spectrum. For each sample, 32 scans were obtained at 4 cm$^{-1}$ spectral resolution and averaged.

Raman Spectrometry

The Raman spectra of the sample were recorded with a FT-Raman module on a vertex 70 FTIR spectrometer (Bruker RAM II, Bruker optics, Germany). A germanium photodiode was used to record FT-Raman spectra excited by an Nd:Yag laser (suppression of fluorescence). A polystyrene standard was run prior to sample analyses. Acquisition time for each spectrum was 1 minute, with a resolution of 4 cm$^{-1}$ and the power of the 1064 nm laser at the sample was 50 mW.

Identity, Assay and Purity

Typically 10 μL aliquots of the sample solutions were diluted to 1 mL with acetonitrile and the assay concentrations were determined from an average of duplicate injections using the following HPLC method. The purity and impurity analyses are done using conventional HPLC.

Column: Zorbax Eclipse XDB C$_{18}$, 4.6×150 mm, 5μ

Column temperature: 25° C.

Injection volume: 5 μL

Detection: UV, 238 nm

Flow rate: 0.8 mL/min

Run time: 30 minutes

Mobile phase A: 0.1% TFA in water

Mobile phase B: 0.1% TFA in acetonitrile

| Time (min) | % A | % B |
|---|---|---|
| 0 | 70 | 30 |
| 6.0 | 55 | 45 |
| 10 | 55 | 45 |
| 25 | 10 | 90 |
| 25.1 | 70 | 30 |
| 30 | 70 | 30 |

EXAMPLES

Process for Preparing Compound I

Compound I can be prepared according to Scheme I:

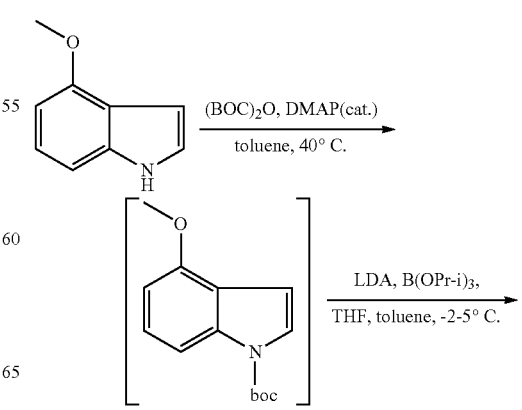

Scheme I.

-continued

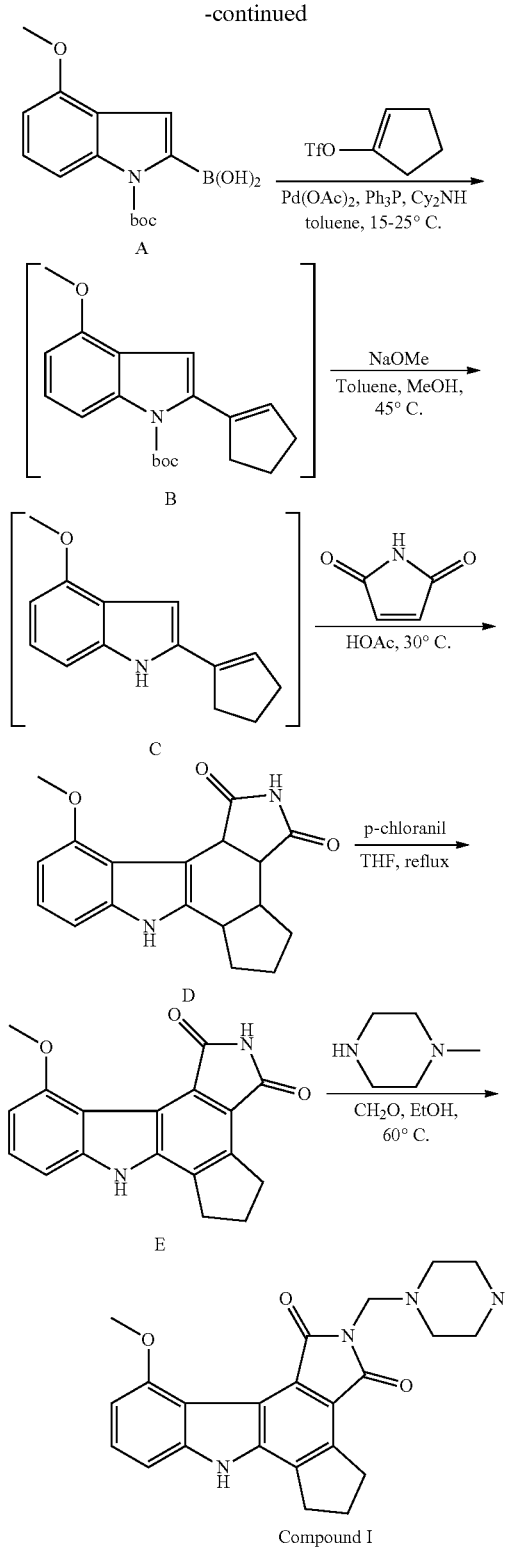

In Scheme I, the synthesis is initiated with 4-methoxyindole, a commercially available starting material. Upon masking the indole nitrogen with di-tert-butyldicarbonate ((Boc)$_2$O), the indole derivative is activated with lithium diisopropylamide (LDA) to generate the carbanion at the 2-position of the indole, which reacts in-situ with triisopropyl borate. Acidic workup hydrolyzes the boronate ester intermediate to the corresponding indole boronic acid compound A. Compound A is then coupled with 1-cyclopentenyl trifluoromethanesulfonate (also called enol triflate in this report) in the presence of catalytic amounts of palladium acetate and triphenylphoshpine under Suzuki conditions to give the key diene intermediate compound B. After removing the Boc protecting group with sodium methoxide, diene compound C is coupled with maleimide via Diels-Alder reaction in acetic acid to give the pentacyclic intermediate compound D. Aromatization via chloranil oxidation converts compound D to compound E, which is coupled with 1-methylpiperazine under Mannich conditions to furnish the target molecule Compound I. Detailed aspects of the synthesis are provided below.

Synthesis of N-Boc-4-Methoxyindole

Into a 100-gal glass-lined reactor was charged 4-methoxyindole (20.0 kg, 136 mol, Yixing Zhongyu Medicine Technology Co., Ltd.), followed by DMAP (0.50 kg, 4.1 mol, Aldrich) and toluene (92 kg, Corco reagent grade). The resulting mixture was stirred and warmed to about 40° C. Meanwhile, a solution of di-tert-butyl dicarbonate (31.8 kg, 146 mol, Lacamas Laboratories, Inc.) in toluene (60 kg, Corco reagent grade) was prepared in a second reactor. This solution was added to the indole solution over about 1$^3$/4 hours. The slightly exothermic reaction (maximum temperature about 41° C.) was accompanied by gas evolution. After being agitated for an additional hour at 40° C. the reaction solution was cooled to 20±3° C. An in-process test revealed that 4-methoxyindole was consumed completely. Deionized water (15 gallons) was added to decompose the excess (Boc)$_2$O (Caution: gas evolution). The resulting mixture was agitated vigorously for ½ hour then allowed to stand overnight. After the lower aqueous layer was removed, the organic layer was partially concentrated under reduced pressure to remove about 145 L of distillate (60° C. jacket, up to 60 mmHg). At this point, additional toluene (30 kg, Corco reagent grade) was charged in and distillation continued until a total of approximately 200 L of distillate was collected. The batch was then cooled to room temperature and drained into a poly drum, resulting in 62.3 kg of a dark amber solution containing 33.6 kg of N-Boc-4-methoxyindole (theoretical yield assumed). This was used in the next stage without further purification.

Synthesis of Compound A

2-Borono-4-methoxy-1H-indole-1-carboxylic acid 1-(1,1-dimethylethyl) ester

Approximately half of the above solution was charged into a 100-gal glass-lined reactor, followed by the additions of toluene (3.0 kg to dilute the charge to 50 wt %), triisopropyl borate (19.9 kg, 105.9 moles, Anderson Development Co.), and THF (91 kg, Corco reagent grade). The resulting solution was agitated and cooled to −2° C. At this point, lithium diisopropylamide (37.3 kg, 91.8 moles, 27% solution in ethyl benzene/tetrahydrofuran/heptane, FMC Lithium) was added over one hour, keeping the batch temperature below 3° C. (−10° C. jacket). The resulting reaction mixture was agitated at 0±3° C. after the addition of LDA until the completion of the reaction was detected by HPLC (0.6 A % of N-Boc-4-methoxyindole remaining 30 min after the addition of LDA). Meanwhile, a solution of 3 N HCl was prepared and cooled to ~5° C. in a second reactor by diluting 27 kg of concentrated hydrochloric acid in 16.3 gallons of de-ionized water. This dilute HCl was added to the batch over one hour to maintain the batch temperature at <15° C. (Batch temperature reached 8° C. at the end of the addition.) The jacket temperature was then set to 20° C. The reactor and addition lines were rinsed with deionized water (6 gallons) and the rinse was combined with the batch. This was followed by the addition of MTBE (27 kg, Pride). The resulting mixture was agitated for ½ hour then stopped for phase separation. The aqueous layer was separated and back-extracted with MTBE (14 kg, Pride) in a second reactor. The combined organic layers were washed consecutively with 5% NaCl (34 L), 5% NaHCO$_3$ (34 L), and 10% NaCl (19 L). After being dropped to a drum and weighed (172.2 kg), the organic phase was returned to the reactor and concentrated under reduced pressure (reactor jacket set point: 30° C.), removing 116 kg of distillate over a three-hour period. The resulting slurry was diluted with n-heptane (75 kg, CORCO reagent grade) and further distilled to remove additional 75 L of distillate. After being stirred at room temperature overnight, the slurry was cooled to ~5° C. for one hour. The product was collected on an Aurora filter and washed with 33 kg of n-heptane. The filter cake was tray-dried under house vacuum overnight with nitrogen bleeding but no heat. There resulted 17.8 kg (88.8% yield, corrected) of compound A as an off-white solid. HPLC purity: 100 LCAP, 95.8 LCWP.

Synthesis of 1,1,1-trifluoromethanesulfonic acid 1-cyclopenten-1-yl ester

Into a 100-gallon glass-lined reactor at room temperature was charged cyclopentanone (8.95 kg, 106.5 mol), followed by toluene (116.40 kg, CORCO reagent grade) and ethyldiisopropylamine (16.6 kg, 128.7 mol). The resulting solution was agitated and heated to 45±5° C. At this point, trifluoromethanesulfonic anhydride (36.2 kg, 128.4 mol) was added over approximately one hour from a 30-L addition flask. The addition of trifluoromethanesulfonic anhydride was very exothermic. Jacket cooling (set at 10° C.) was applied to maintain the batch temperature at 45±5° C. The batch did fall below 40° C. for 7 minutes during the 44 minute addition. Agitation continued at 39-45° C. for 20 minutes after the addition of trifluoromethanesulfonic anhydride. An in-process test after this 20 minutes revealed the total consumption of cyclopentanone. After being cooled to 19.6° C., the batch was filtered through a pad of Celite (18.0 kg) in a filter. The filtrate was collected in a clean poly-lined steel drum. The Celite pad was rinsed with toluene (37.0 kg, CORCO reagent grade). The rinse was combined with the batch in the same poly-lined steel drum. The filtrate (159.85 kg) was analyzed against a reference standard to show it contained 19.50 kg (83.3% yield) of enol triflate. This enol triflate solution in toluene was kept in the cold room overnight and used in the subsequent Suzuki coupling without further purification.

Synthesis of Compound B 2-(1-Cyclopenten-1-yl)-4-methoxy-1H-indole-1-carboxylic acid 1,1-dimethylethylester Into a 100-gal glass-lined reactor at room temperature were charged compound A (18.00 kg, 61.8 mol), triphenylphosphine (648.8 g, 2.47 mol), and palladium acetate (277.0 g, 1.23 mol). The reactor was then evacuated and refilled with nitrogen three times. Toluene (78.3 kg, CORCO reagent grade) was jet pumped into the reactor followed by dicyclohexylamine (44.5 kg, 245.4 mol). This addition took 4 minutes. The resulting slurry was allowed to agitated vigorously (125 rpm) at room temperature for 21 minutes, followed by the slow addition of enol triflate stream in toluene (131.7 kg, containing 16.07 kg of enol triflate, 74.3 mol) over 43 minutes. The addition of enol triflate was exothermic. Jacket cooling was applied to keep the batch temperature at 18.8-27.5° C. The resulting heterogeneous mixture was agitated at 18.4-22.3° C. until the completion of the reaction was detected by HPLC (Note: Though the reaction was complete in less than an hour it was still agitated at the room temperature overnight before continuing the work up. This was strictly for the sake of convenience. The batch may be held at room temperature for up to 100 hours with no adverse effect on the product.) Celite (9.00 kg) was added to the batch. The batch was agitated at room temperature for 10 minutes, and then filtered through a pad of Celite (2.70 kg) in a filter. The filtrate was collected in two clean poly-lined steel drums. The filter cake was rinsed with toluene (47.8 kg, CORCO reagent grade). The rinse was combined with the batch in the same poly-lined steel drums. The filtrate (260.45 kg) was analyzed against a reference standard to show it contained 20.59 kg (106.4% yield) of compound B. It was assumed based on the assay that this reaction went in 100% yield, and the charges for the next step were done as if it had gone in 100% yield. The solution of compound B in toluene was kept in the pilot plant at room temperature and used in the subsequent deprotection procedures without further purification.

Synthesis of Compound C 2-(Cyclopenten-1-yl)-4-methoxy-1H-indole

Into a 100-gal glass-lined reactor at room temperature was charged the toluene stream of compound B (12.82 kg of compound B, 40.96 moles), followed by the addition of sodium methoxide (44.0 kg, 25-30 wt % solution in MeOH, 203.7 moles). The resulting solution was agitated and heated to 45±5° C. Agitation continued at 45±5° C. until the completion of the reaction was detected by HPLC (reaction complete in ~4 hrs, HPLC data returned at ~8 hrs). The batch was then cooled to 23.5° C. over 26 minutes. The batch was agitated overnight at 22±2° C. After ~17 hours at 22° C. approximately ½ of the batch (111.15 kg) was transferred to a second reactor and worked up separately. To the first reactor was charged DI water (21 gallons). The resulting mixture was agitated for 16 minutes then stopped. After the batch was allowed to settle at room temperature for 46 minutes, the bottom aqueous layer was removed. This was followed by a small portion of a rag layer that was drained into a clean carboy. The remaining organic layer was filtered through a pad of Celite (3.84 kg) in a filter. The filtrate was collected in a clean poly-lined steel drum. The rag layer was then filtered through the same celite pad and the filtrate was collected in a new carboy. The Celite pad was washed with toluene (6.20 kg, CORCO reagent grade) and this wash was combined with the filtered rag layer. The filtered rag layer was then transferred to a glass addition vessel where the bottom aqueous layer was removed and the organic layer from the rag was combined with the original organic layer. The above workup procedure was repeated on the second half of the batch, generating the second toluene solution of compound C. As much of the second solution as would fit was placed in the poly-lined steel drum with the first organic layer (164.70 kg, containing 8.14 kg of compound C). The remaining second organic layer was contained in a small poly drum (19.05 kg, containing 0.49 kg of compound C). These two solutions were held in the pilot plant for further processing in the next stage without any further purification. A total of 8.63 kg (99.2% yield) of compound C was generated.

Synthesis of Compound D 3a,3b,4,5,6,6a,7,11c-Octahydro-[1-methoxy-1H-cyclopentaia]pyrrolo[3,4-c]carbazole-1,3 (2H)-dione Into a 100-gal glass-lined reactor at room temperature was charged a toluene stream of compound C (12.58 kg of compound C, 59.1 mol). This solution was concentrated under full house vacuum and <40° C. internal temperature until the residue was approximately six times the weight of compound C (targeted volume ~75.5 L) over approximately 7 hours. This residue was drained into a clean polyethylene drum and used in the following Diels-Alder reaction without any further purification. Into a second 100-gal glass-lined reactor was charged maleimide (7.45 kg, 76.8 mol, Carbosynth Limited), followed by glacial acetic acid (145.70 kg). The resulting mixture was stirred to achieve a solution. At this point, the concentrated compound C solution from above (84.95 kg) was charged in over approximately 20 minutes to control the batch temperature at 20±10° C. (Jacket temperature was set at 15° C.) The resulting mixture was agitated at 30±3° C. until the completion of the reaction was detected by HPLC (reaction is done at ~15.5 hours, HPLC data is received at ~17.5 hours). The batch was then cooled to 23.2° C. over approximately 20 minutes. After the mother liquor was analyzed by a weight based HPLC assay and confirmed that it contained less than 10% of compound D (found: 5.88%), the batch was filtered on an Aurora filter (2.5 hrs from reaching 23.2° C. to filter time). The filter cake was rinsed with glacial acetic acid (39.65 kg) and pulled dry in the filter under vacuum with a stream of nitrogen until the purity of compound D met the set specification (>90 wt %) by HPLC weight based assay (drying was done over 3 nights, purity was 99.5 wt % after 3 nights). The product was then unloaded to a double polyethylene bag-lined fiber drum to give 13.43 kg (73.3% yield) desired compound D as a tan solid. This material was used in the subsequent chloranil oxidation without any further purification.

Synthesis of Compound E 4,5,6,7-tetrahydro-11-methoxy-1H-cyclopenta[a]pyrrolo[3,4-c]carbazole-1,3(2H)dione Into a 100-gal glass-lined reactor at room temperature was charged compound D (28.66 kg, 92.45 mol), followed by tetrachloro-p-benzoquinone (45.50 kg, 185.0 mol, 99%, ACROS) and THF (253.1 kg, CORCO reagent grade). The resulting heterogeneous mixture was heated to 65±5° C. and agitated at this temperature until the completion of the reaction was detected by HPLC (reaction is done in ~22 hrs, HPLC data is received at ~23 hrs). The batch was then cooled to 22±5° C. over 35 minutes, analyzed for the loss of compound E in the solution (<10% specification. found: 1.9%), and filtered on a filter. The reactor, lines, and filter cake were rinsed with a mixture of THF-EtOH—H$_2$O (prepared in a second reactor by mixing 62.0 kg of THF with 41.25 kg of EtOH and 4.64 gallons of de-ionized water). The wet cake was dried in a filter under vacuum with a stream of nitrogen until the product meets the set specification (>80 wt % of compound E spec. found: 80.8 wt % after 5 days). The product was then unloaded to two double polyethylene bag-lined plastic pails, yielding 23.84 kg (86.7% yield) of compound E as a dark greenish yellow solid. This material was used directly in the subsequent Mannich reaction without further purification.

Synthesis of Compound I

Into a 100-gal glass-lined reactor was charged compound E (15.20 kg, 40.1 moles), followed by paraformaldehyde (2.51 kg, 80.9 moles, 97%, ACROS) and denatured ethanol (223.45 kg, reagent grade). The resulting mixture was agitated (121 rpm) while 1-methylpiperazine (6.65 kg, 65.77 moles, ACROS, 99%) was added over approximately 10 min from an addition flask. The resulting reaction mixture was heated and agitated at 70° C. The progress of the reaction was monitored by HPLC (1.35 A % compound E remaining after ~5 hours). After being agitated at 70° C. for a total of 9 hours, the batch was cooled to 20±3° C. and stirred at this temperature overnight. The product was filtered on a filter. The filter cake was rinsed with ethanol (43.9 kg, reagent grade) and pulled dry on the filter with nitrogen bleeding until the residual ethanol was less than 12 wt % by $^1$H NMR (8.4 wt % vs. compound I). The product was then unloaded to a polyethylene bag-lined fiber drum to give 18.05 kg (95.8% yield) of crude compound I as a yellow solid: 98.6 LCAP, 89.2 LCWP. This material was used directly in the down stream process without further purification.

Polymorph Screening Studies

Crystallization studies were performed to investigate polymorphism in 48 different solvents. Solvents were selected on the basis of acceptability (ICH Class 3 and 2) and to give a range of dielectric constants, dipole moments and functional groups. Two starting materials were selected: Form $A_0$ and Lot 7 (a mixture of Form $A_0$, Form $HC_0$ and Form $HD_0$). When possible, full characterization was performed on the new forms that were generated during the polymorphism screening of Compound I. This characterization consisted of: XRPD, thermal analysis, DVS, storage at 40° C./75% RH and purity.

Four crystallization procedures including cooling, evaporation and anti-solvent addition were employed to obtain different polymorphic forms of Compound I. The details of each crystallization procedure are given below. The solid forms obtained from each solvent from these procedures are summarized in Table 15.

Crystallization Procedure:
1. Rapid Crystallization Screen
Two small scale screening procedures were used:
A. Approximately 1 mg of Compound I was weighed into a 0.5 mL polypropylene centrifuge tube and 0.5 mL of a solvent. The centrifuge tube was allowed to stand for 18 hours undisturbed at room temperature and observed for changes. The tube was then agitated for 2.5 hours at 52.5° C. and each tube observed for changes. The warmed centrifuge tube was then agitated for 20 hours at 2-8° C. and observations made for changes in crystallinity (if any) from initial room temperature condition were recorded.
B. Plates containing 10 volumes of Compound I (40 mg of Lot 7 in 400 µL) were heated from 20° C. to an initial temperature of 80° C. at a rate of 4.8° C./min and after 30 minutes, cooled at a slow (0.28° C./min), or fast (10° C./min) rate to a final temperature of 5° C. and kept at that temperature for 18 hours. The crystallization experiments were carried out in glass vial (4 mL) well plates, and solid material was isolated by filtration. The solid was dried at 57° C. for 10 hours.
2. Quick Cool Crystallization
Samples were prepared by adding 40 mg (±2) of Compound I solid material into a solvent volume to assure saturated conditions at the boiling point. The mixture was cooled and filtered through a 0.2μ nylon membrane filter into a warmed glass vial or Erlenmeyer flask. The solution was cooled to room temperature and placed in a refrigerator (ca. 4° C.) until crystal formation appeared to reach completion as determined by visual inspection. Each refrigerator-sample was decanted and the crystals were transferred to weighing paper and dried to constant weight under ambient laboratory conditions. Samples difficult to decant were centrifuged at 12000 rpm for four minutes. If the quick-cool procedure did not result in solid materials, these samples were concentrated by evaporating approximately half the solvent volume. The solutions were again placed in the refrigerator and any solid material was isolated by decanting or centrifugation.

3. Crystallization by Maturation with Lot 7 and Form $A_0$

Two types of maturation studies were performed:

A. Samples were prepared by adding approximately 10 mg of either Lot 7 or Form $A_0$ to 1.0 mL of each solvent in a screw cap vial (about 4.0 mL volume). These were then warmed to 64° C. while being shaken. After holding at 64° C. for 40 minutes, the samples were chilled down to 5° C. (at a rate of −0.25° C./min). The samples were held at 5° C. for a total of 18 hours and transferred via pipette to 1.5 mL polypropylene centrifuge tubes and spun at 12000 RPM for 1 minute. The supernatant liquid was decanted. The residues in the centrifuge tubes or glass vials were then dried in a vacuum drying oven at 110° C. for 18 hours and analyzed by XRPD.

B. Approximately 40 mg of Form $A_0$ was slurried in the different solvents (10 volumes (40 mg in 400 μL). The slurries were shaken for 48 hours with alternating 4 hour periods at 50° C. (0.5° C./min) and 5° C. (−0.5° C./min). Any solid material was then isolated by filtration and analyzed by XRPD and thermal analysis.

4. Crystallization by Slurry with Form $A_0$

The slurries (20 mg of form $A_0$ in 500 μL of each solvent) were shaken at 25° C. with different times. The solid was isolated by filtration and dried at 57° C. for 2 hours and analyzed by XRPD.

The XRPD results from the isolated solids from the four crystallization methods are recorded in Table 15 below.

TABLE 15

Summary of forms of Compound I obtained based on XRPD results from 48 different solvents and different crystallization methods

| Solvent | Forms Obtained by XRPD |
| --- | --- |
| 1,2-dichloroethane | $A_0$, $HA_0$, $HC_0$, $HD_0$ |
| 1,2-dimethoxyethane | $HA_0$ |

TABLE 15-continued

Summary of forms of Compound I obtained based on XRPD results from 48 different solvents and different crystallization methods

| Solvent | Forms Obtained by XRPD |
| --- | --- |
| 1,4-dioxane | $A_0$, $HC_0$, $HD_0$ |
| 1-butanol | $HD_0$ |
| 1-pentanol | $HD_0$ |
| 1-propanol | $S9_0$, $HC_0$, $HD_0$ |
| 2-butanol | $A_0$, $HC_0$, $HD_0$ |
| 2-butanone | $HC_0$, $HD_0$ |
| 2-methyl-tetrahydrofuran | $A_0$, $HC_0$, $HD_0$ |
| 2-pentanone | $HA_0$, $HC_0$, $HD_0$ |
| 2-propanol | $S3_0$, $HC_0$, $HD_0$ |
| 3-pentanone | $A_0$, $HA_0$, $HC_0$, $HD_0$ |
| Acetone | $A_0$, $HC_0$, $HD_0$ |
| Acetonitrile | $HC_0$, $HD_0$ |
| Butyronitrile | $A_0$, $HA_0$, HD |
| Chlorobenzene | $A_0$, $HD_0$ |
| Chloroform | HC, $HD_0$ |
| Cyclohexane | $A_0$, $HC_0$, $HD_0$ |
| Dichloromethane | $A_0$, $HC_0$, $HD_0$ |
| Diethylene glycol dibutyl ether | $A_0$ |
| Diisopropyl amine | $A_0$, $HD_0$ |
| Diisopropyl ether | $A_0$, $HA_0$, $HC_0$, $HD_0$ |
| Dimethyl sulfoxide | $HC_0$, $HD_0$ |
| Ethanol | $S4_0$ |
| Ethyl acetate | $A_0$, $HC_0$, $HD_0$ |
| Ethyl formate | $HA_0$ |
| Ethylene glycol | $S6_0$ |
| Heptane | $A_0$, $HC_0$, $HD_0$ |
| Isobutanol | $S12_0$, $HD_0$ |
| Isopropyl acetate | $A_0$, $HC_0$, $HD_0$ |
| Methanol | $S2_0$ |
| Methoxybenzene | $HD_0$ |
| Methyl acetate | $A_0$, $HA_0$, $HC_0$, $HD_0$ |
| Methyl isobutyl ketone | $A_0$, $HC_0$, $HD_0$ |
| Methyl tert-butyl ether | $A_0$, $HA_0$, $HC_0$, $HD_0$ |
| N,N-dimethylacetamide | $S10_0$ |
| N,N-dimethylformamide | $S5_0$ |
| N-butyl acetate | $A_0$, $HC_0$, $HD_0$ |
| Propanonitrile | $A_0$, $HA_0$, $HC_0$, $HD_0$ |
| Propylene carbonate | $A_0$, $HC_0$, $HD_0$ |
| Pyridine | $S7_0$ |
| Tert-butanol | $A_0$, $HC_0$, $HD_0$ |
| Tetrahydrofuran | $A_0$, $HC_0$, $HD_0$ |
| Tetrahydropyran | $HC_0$, $HD_0$ |
| Toluene | $A_0$, $HC_0$, $HD_0$ |
| Triethylamine | $HC_0$, $HD_0$ |
| Water | $A_0$, $HA_0$, $HC_0$, $HD_0$ |
| Xylene | $A_0$, $HA_0$, $HC_0$, $HD_0$ |

The polymorph screening of Compound I yielded fourteen forms and a new form (Form $B_0$) obtained only on heating the hydrates above 120° C. A summary of the results of the isolated forms is shown in Table 16 below.

TABLE 16

Characterization data for isolated forms of Compound I

| Form | XRPD | DSC | TGA (weight loss 25° C. to 150° C.) | Physical Stability (XRPD post 4 weeks at 40° C./75% RH) | Chemical Stability (HPLC (post 4 weeks at 40° C./75% RH (Area %) | DVS % increase in mass at 90% RH | XRPD post DVS analysis | Purity (%) |
| --- | --- | --- | --- | --- | --- | --- | --- | --- |
| $A_0$ | Crystalline | Melt endotherm at 239.7° C. | 0.07% | No significant changes | 99.0 | 0.1 | No significant changes | 99.2 |
| $B_0$ | Crystalline | Melt endotherm at 199.8° C. | — | — | — | — | — | — |

TABLE 16-continued

Characterization data for isolated forms of Compound I

| Form | XRPD | DSC | TGA (weight loss 25° C. to 150° C.) | Physical Stability (XRPD post 4 weeks at 40° C./75% RH) | Chemical Stability (HPLC (post 4 weeks at 40° C./75% RH (Area %) | DVS % increase in mass at 90% RH | XRPD post DVS analysis | Purity (%) |
|---|---|---|---|---|---|---|---|---|
| $HA_0$ | Crystalline | Broad endotherm at 99° C. due to water loss. Conversion to form $B_0$ occurs on losing water | 3.9% | No significant changes | 99.0 | 1.5 | No significant changes | 99.6 |
| $HC_0$ | Crystalline | Broad endotherm at 112° C. due to water loss. Conversion to form $B_0$ occurs on losing water | 3.8% | No significant changes | 99.0 | 0.44 | No significant changes | 99.6 |
| $HD_0$ | Crystalline | Broad endotherm at 110° C. due to water loss. Conversion to form B0 occurs on losing water | 4.0% | No significant changes | 92.3 | Insufficient material | No significant changes | 93.5 |

Description of Stable Solid State Forms

Preparation of Anhydrous Form $A_0$

Approximately 200 mg of Compound I was slurried in 45 volumes of heptane at 85° C. for 45 hours, cooled to 65° C. and filter-dried under high vacuum at room temperature for 3 hours. The recovery of Form $A_0$ was 97%.

In an alternative procedure, the conversion of Compound I to Form $A_0$ was achieved according to the following process:
1) Compound I was dissolved in 30 volumes of THF. The solution may be treated with a metal scavenger or carbon at this point, if desired.
2) The resulting solution was filtered to remove the metal scavenger or carbon followed by a polish filtration through a 1-micron inline cartridge filter to remove any external particulates.
3) The solvent (THF) was partially distilled to approximately 60% of the original volume under vacuum at ambient temperature followed by the slow addition of an equivalent volume of an anti-solvent (heptane) to precipitate Compound I.
4) Vacuum distillation and addition of more heptane was continued until the solvent contained less than 5% of THF by volume.
5) The resulting slurry was heated to 90-96° C. and agitated at this temperature for 3-5 hours to achieve a complete conversion to Form $A_0$.
6) The slurry was cooled to ambient temperature (25±5° C.).
7) The product/Compound I was collected via filtration under a dry, inert gas to avoid moisture being sucked through the product.
8) The wet cake was dried at up to 80° C. until the residual solvents in the product met the specifications. Drying may be performed at atmospheric pressure or under vacuum.

Characterization of Form $A_0$ Using Variable Temperature X-Ray Powder Diffraction (VT-XRPD)

No solid-solid transformation takes place in the temperature range 20° C. to 250° C. for Form $A_0$. After exposure to ambient conditions, there is no significant change in the XRPD pattern of the sample obtained by heating to 220° C. (See FIG. 15).

Characterization of Form $A_0$ by Thermal Gravitmetric Analysis (TGA)

Form $A_0$ shows a single peak at ca. 239° C. with an enthalpy of fusion ($\Delta H_{Fus}$) of 84.4 J/g. No loss of mass is detected by TGA. The existence of a desolvation process was discounted because no loss of weight was detected by TGA (See FIG. 16).

Characterization of Form $A_0$ by Water Sorption (DVS)

Regular DVS (0 to 90% RH)

Figure 18:
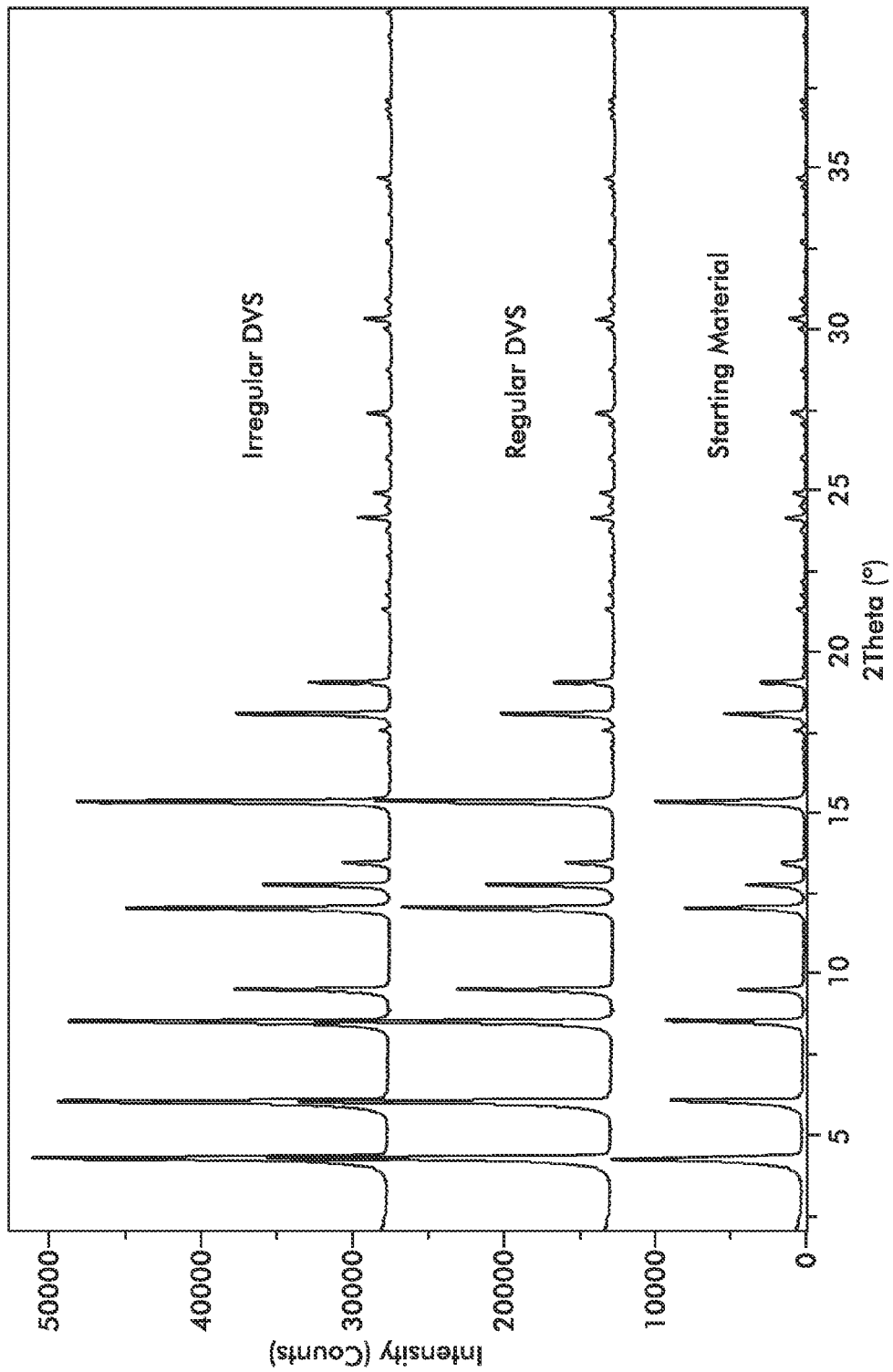
FIG. 18 depicts X-ray Powder Diffractograms (XRPD) of Form $A_0$ before and after Dynamic Vapor Sorption (DVS) analysis.

The amount of moisture adsorbed at 75% RH was less than 0.08% and approximately 0.1% at 90% RH. The adsorption and desorption curves overlap suggesting that Form $A_0$ is not hygroscopic (See FIG. 17 and Table 25). No significant changes were observed by XRPD re-analysis after DVS (FIG. 18).

TABLE 17

DVS Data for Form $A_0$ (Regular)

| Form | At 75% RH uptake | Total uptake at 90% RH |
|---|---|---|
| $A_0$ | 0.08 | 0.1 |

Irregular DVS (90 to 0% RH)

Figure 19:
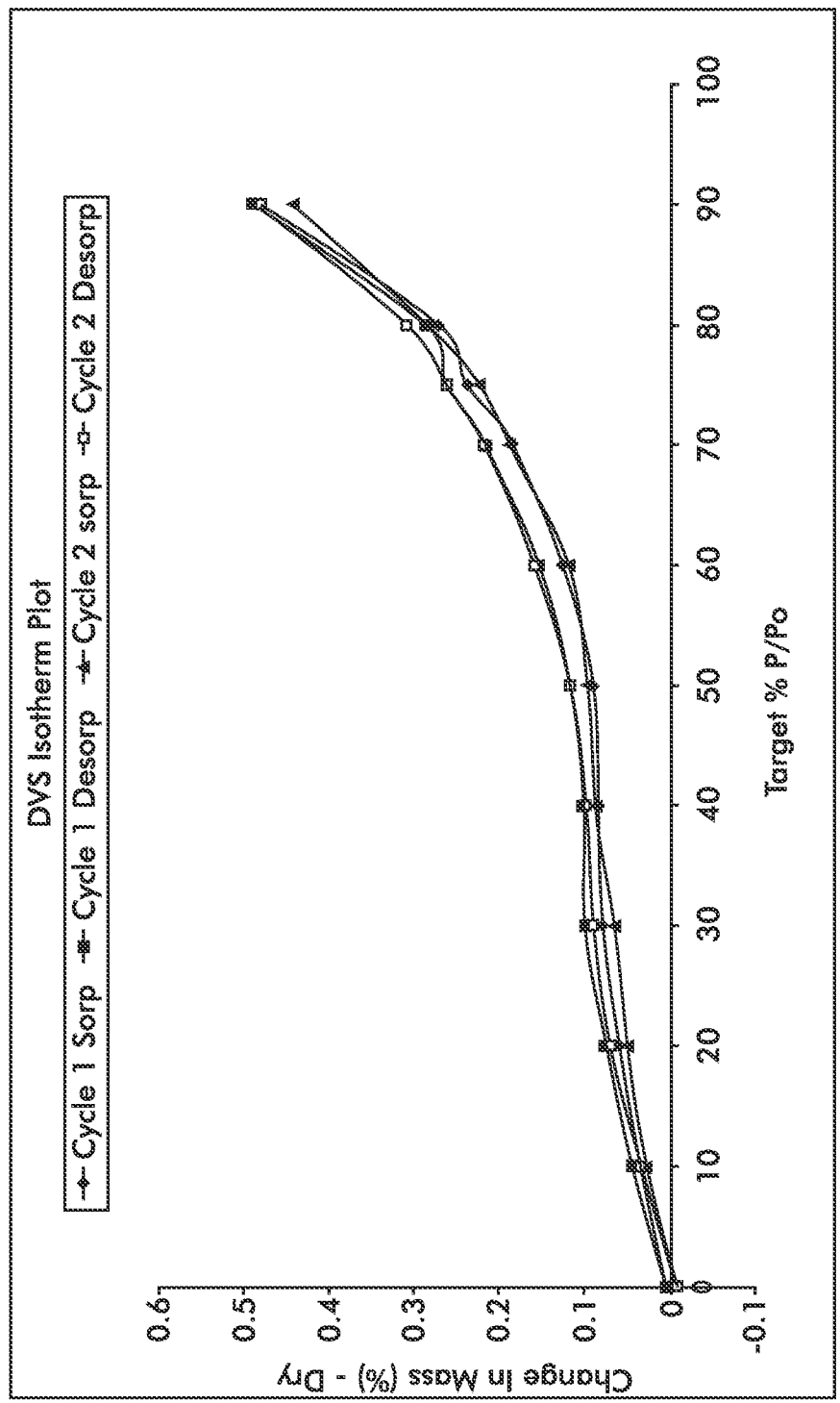
FIG. 19 is a Dynamic Vapor Sorption (DVS) irregular isotherm plot of Form $A_0$.

The sample mass only increases at 0.5% at 90% RH. The hysteresis gap suggests only surface water adsorption is occurring. The isotherm is reversible with a total increase in mass <0.6%. (FIG. 19 and Table 26). No significant changes were observed by XRPD re-analysis after DVS (FIG. 18).

TABLE 18

DVS data for Form $A_0$ (Irregular)

| Form | At 75% RH uptake | Total uptake at 90% RH |
|---|---|---|
| $A_0$ | 0.15 | 0.5 |

Figure 20:
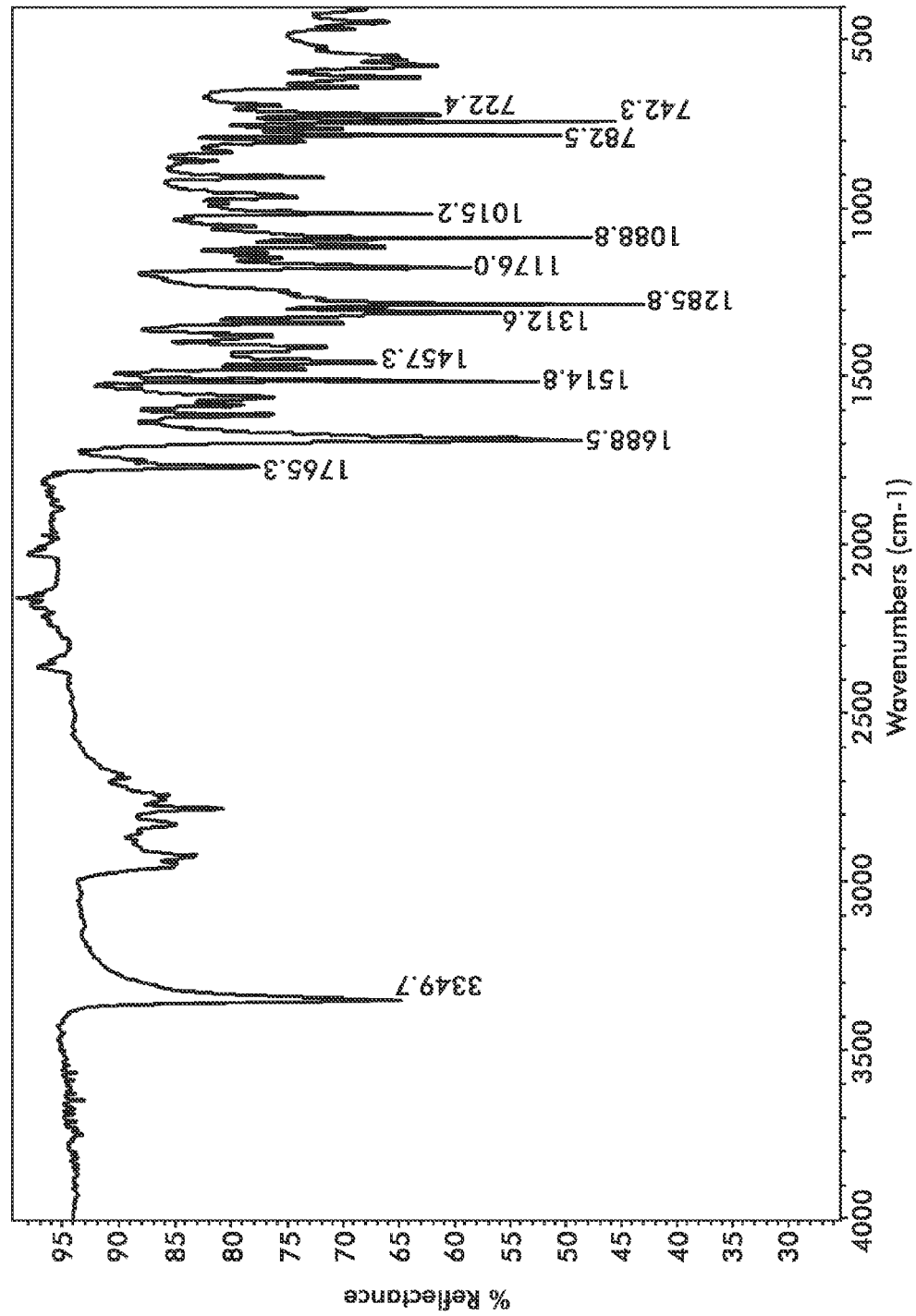
FIG. 20 is a Fourier Transform Infrared (FTIR) spectrum of Form $A_0$.
Figure 21:
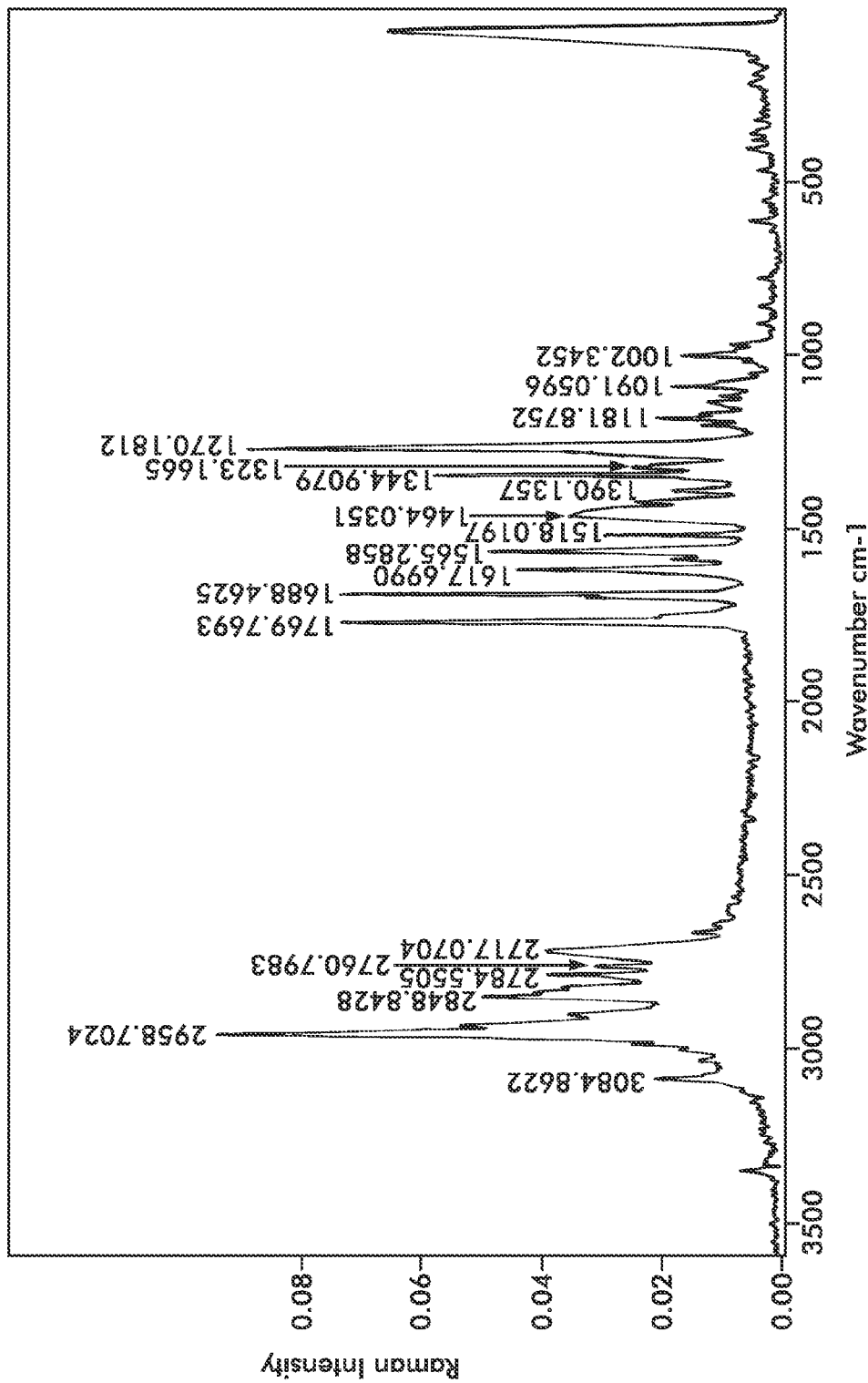
FIG. 21 is a Raman Spectrum of Form $A_0$.

Characterization of Form $A_0$ by Fourier Transform Infrared Spectroscopy (FTIR) and Raman Spectroscopy The FTIR and Raman spectra of the crystalline Form $A_0$ are shown in FIG. 20 and FIG. 21, respectively.

Preparation of Anhydrous Form $B_0$

Form $B_0$ was obtained by heating 20 mg of Compound I to 125° C. under nitrogen flow.

Characterization of Form $B_0$ by Variable Temperature X-Ray Powder Diffraction (VT-XRPD)

Figure 22:
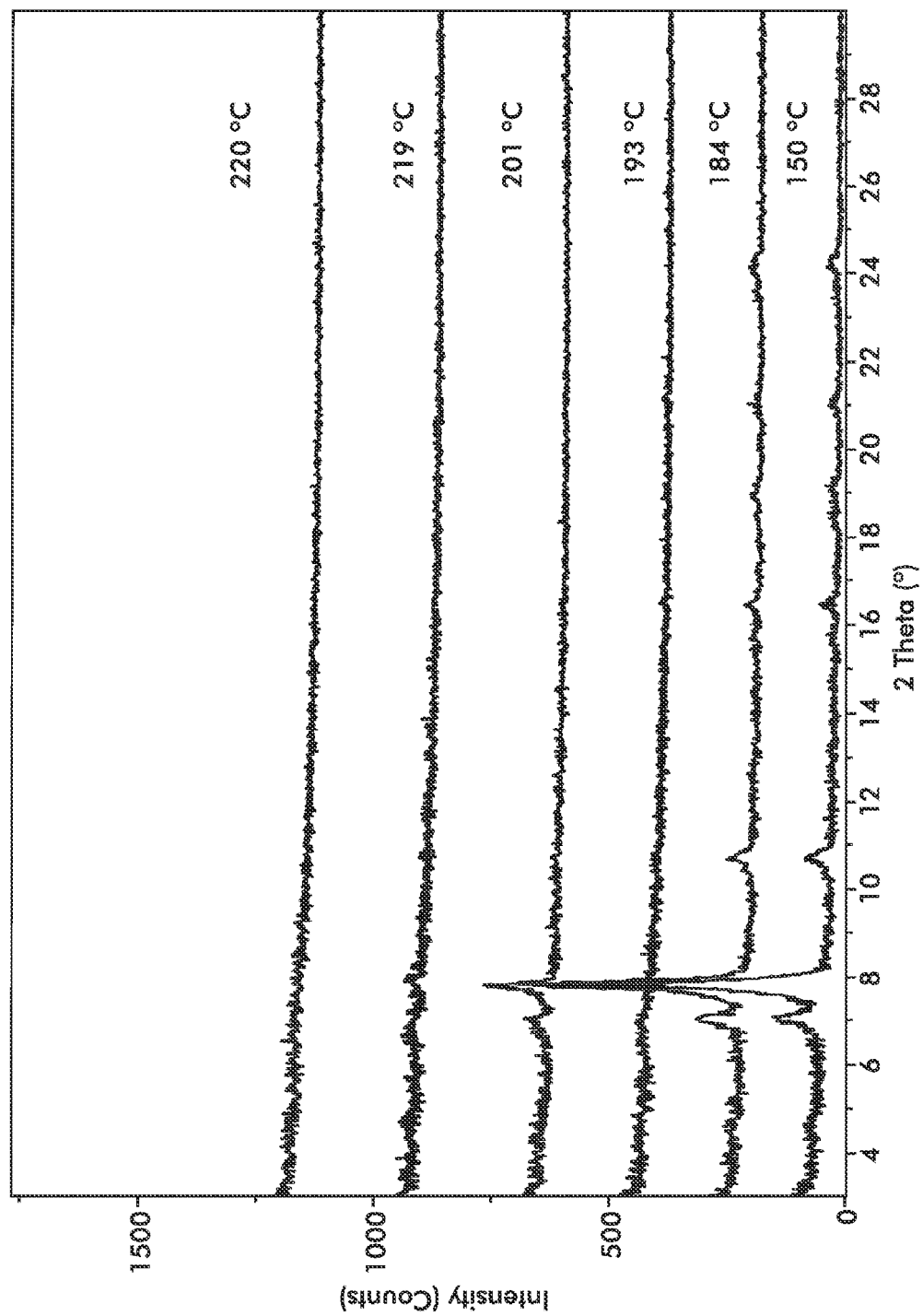
FIG. 22 is a Variable Temperature X-ray Powder Diffractogram (VT-XRPD) of Form $B_0$.

After the dehydration, no solid-solid transformation takes place in the range 150° C. to 200° C. for Form $B_0$ (See FIG. 22).

Characterization of Form $B_0$ by Thermal Analysis

Figure 23:
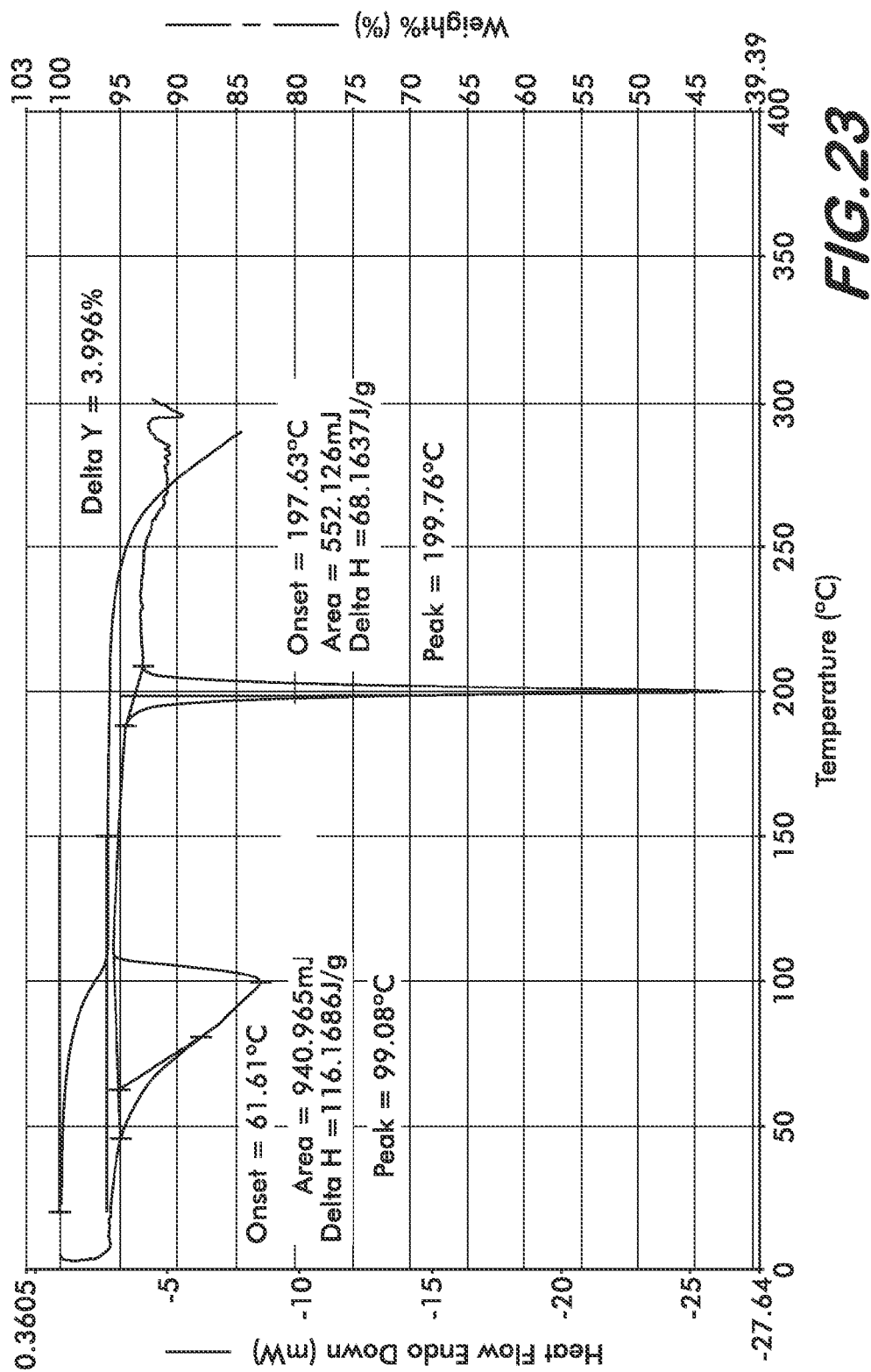
FIG. 23 is a Differential Scanning calorimetry (DSC) Thermogram and Thermo-Gravimetric Analysis (TGA) Thermogram overlay of Form $B_0$.

The Differential Scanning calorimetry (DSC) diagram of Form $B_0$ presents melting at ca. 197° C. with an enthalpy of fusion ($\Delta H_{fus}$) of 68.2 J/g (FIG. 23). A solid-solid transition occurs before the melting point of the form Compound I-$B_0$. Form $B_0$ was obtained only by desolvation. The relative thermodynamic stability of the forms is reflected in the DSC data shown between 120° C. and 199° C.

Preparation of Hydrate Form $HA_0$
Crystallization from THF/Heptane

Form $HA_0$ was obtained as 200 mg of Compound I was precipitated from 70 volumes of THF with 143 volumes of heptane at room temperature. The solid was isolated by filtration. The material was dried at 57° C. for 18 hours.

Preparation by Solid-Solid Transition

Form $HA_0$ was obtained as 20 mg Compound I was heated to 125° C. and cooled to room temperature without nitrogen flow.

Characterization of Form $HA_0$ by Thermal Analysis

Figure 24:
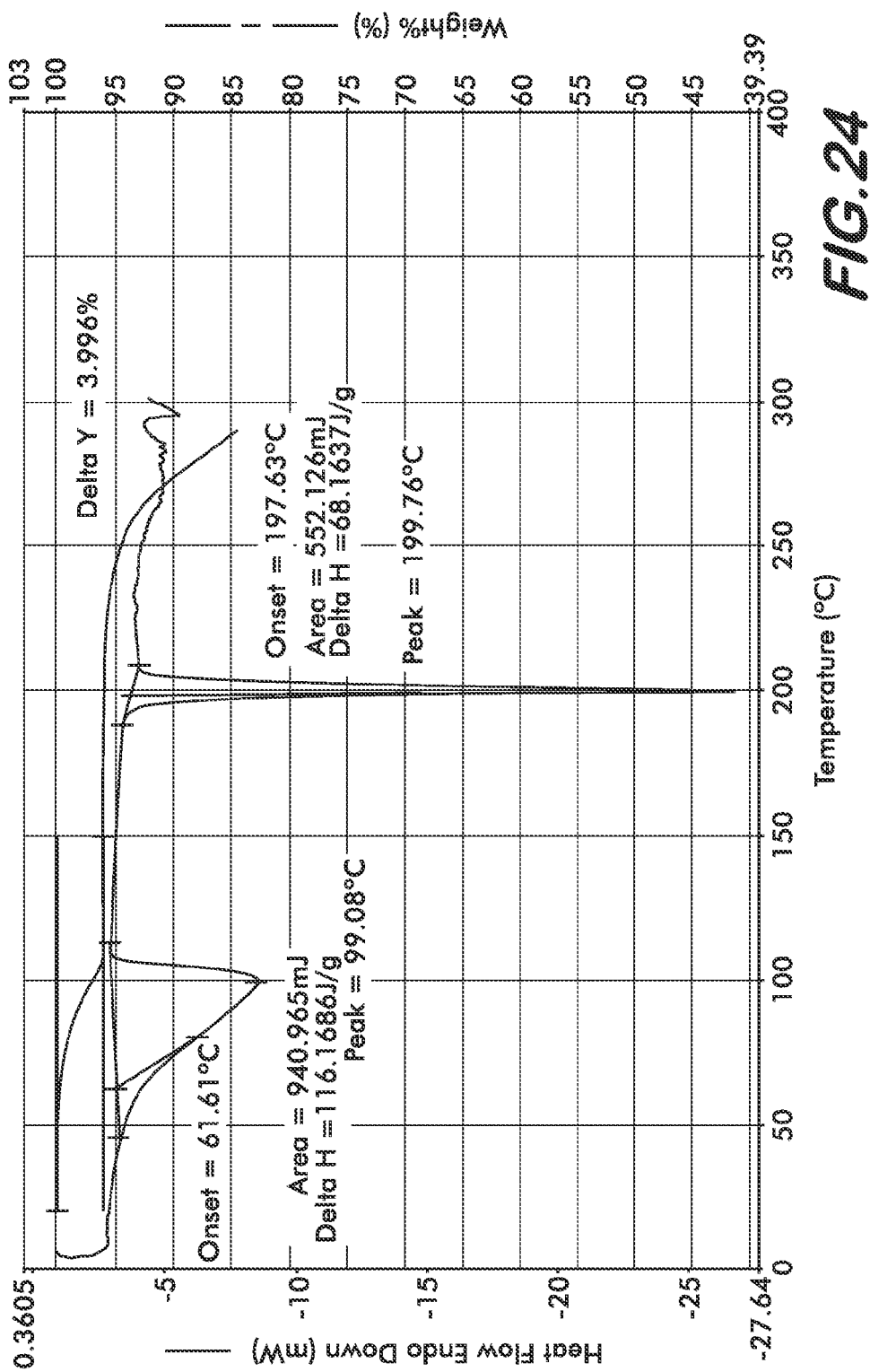
FIG. 24 is a Differential Scanning calorimetry (DSC) Thermogram and Thermo-Gravimetric Analysis (TGA) Thermogram overlay of Form $HA_0$.

The DSC thermograms of Form $HA_0$ show the presence of two different endothermic peaks (FIG. 24 and Table 27). In an open pan, hydrates exhibit a broad endothermic peak between approximately 60 and 120° C. corresponding to the total amount of water escaping from the crystal. The endothermic event corresponds to the dehydration process involving the escape of water from the lattice. Desolvation occurs in the solid state with an endothermic peak. The position and energy of this endothermic peak depend on the phase diagram of two components, the drug substance and the solvent and the stability of the component formed. The DSC thermograms of the solvates present broad endothermic peaks at temperatures near the boiling points of their respective solvents that can be assigned to desolvation processes, is confirmed by TGA. The monohydrate Form $HA_0$, when studied by TGA, demonstrated an average weight loss of 4.0% between 50 and 120° C. This agrees with the theoretical value for incorporation of one mole of water with one mole of Compound I is 4.1%

TABLE 19

DSC onset and peak temperatures of desolvation for Form $HA_0$

| Classification | Solvent | Solvate Weight loss (%) | Principal onset Temp./ ° C. | Peak Temp./ ° C. |
|---|---|---|---|---|
| $HA_0$ | Water | 4.0 | 61.6 | 99.1 |

Characterization of Form $HA_0$ by Water Sorption

Figure 25:
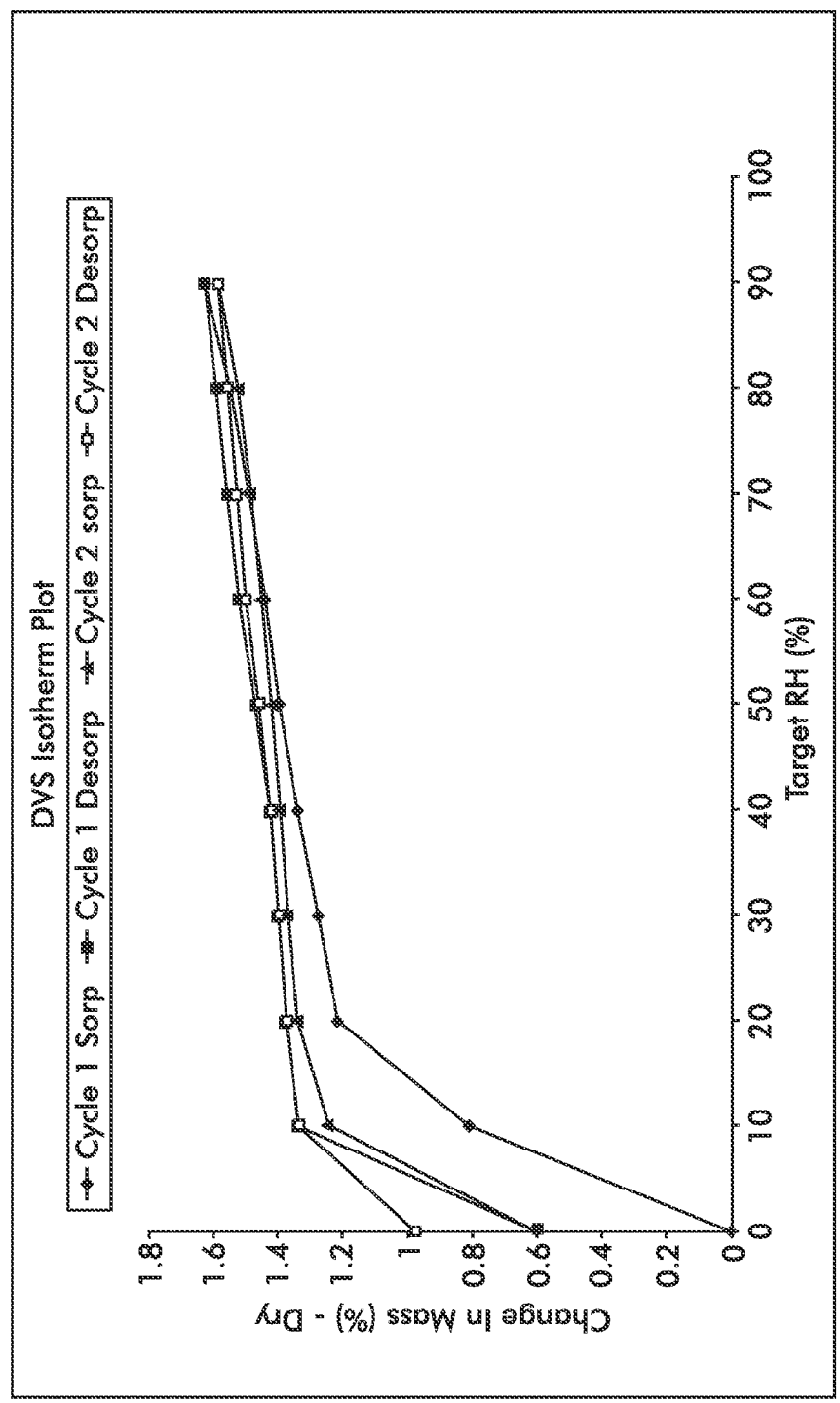
FIG. 25 is a Dynamic Vapor Sorption (DVS) isotherm plot of Form $HA_0$.

FIG. 25 displays the dynamic vapor sorption data collected on Form $HA_0$. Upon drying, there is an immediate uptake upon exposure to moisture. The isotherm of the Form $HA_0$ shows a 1.25% weight decrease between 20-30% RH. From 30-90% RH the uptake begins to reach equilibrium. During the first desorption phase there is a slight hysteresis suggesting only surface adsorption. There is almost no desorption during second desorption phase, but the sample experiences a second change of ~0.4%. The sorption shows evidence that this form is a channel hydrate. The non-stoichiometric hydration comes from incomplete hydration of the lattice channels. No significant changes were observed on XRPD re-analysis after DVS.

Characterization by FTIR and Raman Spectroscopy

Figure 26:
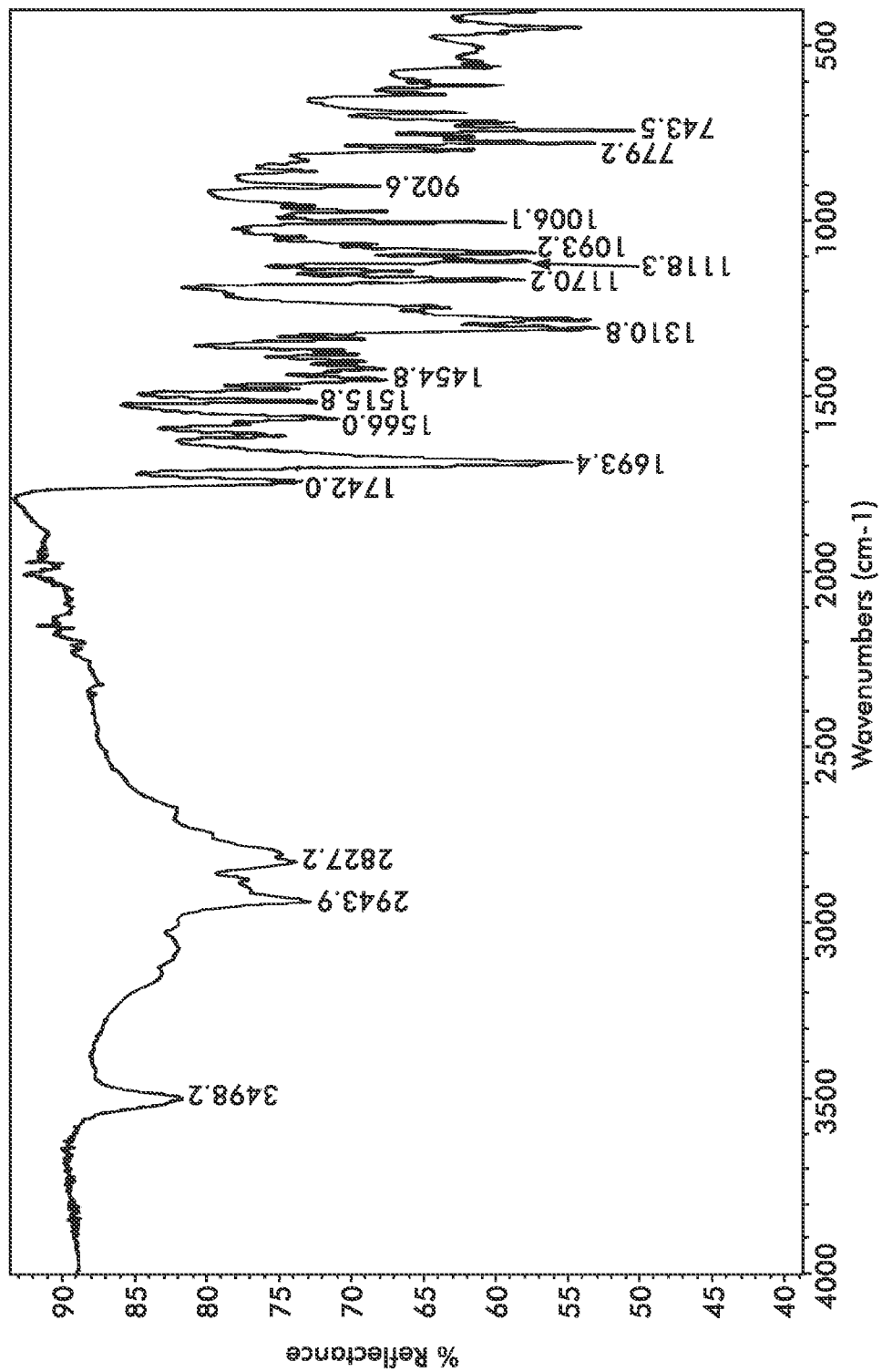
FIG. 26 is a Fourier Transform Infrared (FTIR) spectrum of Form $HA_0$.
Figure 27:
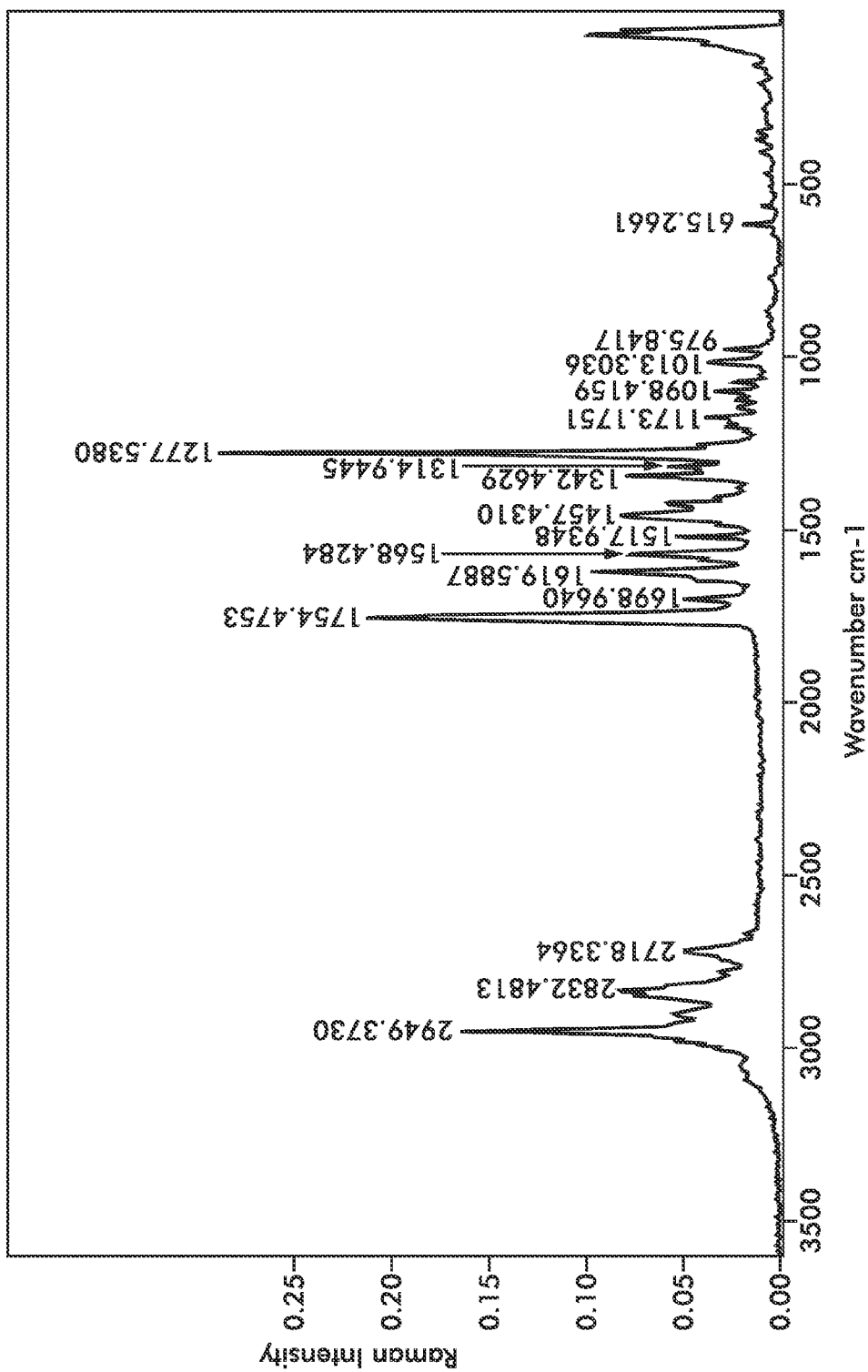
FIG. 27 is a Raman spectrum of Form $HA_0$.

The FTIR and Raman spectra of the crystalline Form $HA_0$ are shown in FIG. 26 and FIG. 27, respectively.

Preparation of Hydrate Form $HC_0$
Recrystallization from Ethanol/Water

Form $HC_0$ was obtained as 40 mg of Lot 7 was added in 400 μL of ethanol and 100 μL of water. The sample was heated to an initial temperature of 80° C. at a rate of 4.8° C./min and, after 30 minutes, cooled at 0.28° C./min to a final temperature of 5° C. and kept at that temperature for 18 hours. The solid was isolated by filtration. The material was dried at 57° C. for 10 hours.

Storage at 40° C./75% RH with the Ethanol Solvate

Form $HC_0$ was obtained as 20 mg of ethanol solvate of Compound I was stored at 40° C./75% RH for 9 days.

Preparation of Crystal Structure

Single crystals were prepared by adding 200 mg of Lot 7 solid material to tetrahydrofuran for the monohydrate $HC_0$ to assure saturated conditions at the boiling point. The mixture was cooled and filtered through a 0.22μ nylon membrane filter into a warmed glass vial. The solution was cooled to 20° C.±0.2° C. in order to increase the supersaturation value, and the homogeneous solution was left standing for several days.

Crystal Structure Determination by Single Crystal X-Ray Diffraction

Single crystal X-Ray data was obtained for $HC_0$ Cell parameters obtained from the data are presented in Table 28.

The data were collected at a temperature of 103K using the ω-2θ scan technique. A colorless plate of $C_{24}H_{28}N_4O_4$ having approximate dimensions of 0.30×0.16×0.11 mm was mounted on a glass fiber in a random orientation. The triclinic cell parameters (P-1, Z=2) and calculated volumes are:

| | |
|---|---|
| a = 7.6128(10) | α = 65.839(18)° |
| b = 11.5697(15) | β = 79.137(16)° |
| c = 13.193(4)Å | γ = 86.800(10)° |
| V = 1040.9(3)Å³. | |

TABLE 20

Crystal X-ray data collection and refinement parameters for Form $HC_0$

| Identification code | Form $HC_0$ |
|---|---|
| Empirical formula | $C_{24}H_{28}N_4O_4$ |
| Formula weight | 436.50 |
| Temperature | 103(2) K |
| Wavelength, Å | 0.71073 |
| Crystal system, Space group | Triclinic, P-1 |
| Unit cell dimensions a, Å | 7.6128(10) |
| b, Å | 11.5697(15) |
| c, Å | 13.193(4) |
| α, ° | 65.839(18) |
| β, ° | 79.137(16) |
| γ, ° | 86.800(10) |
| Volume | 1040.9(3) |
| Z | 2 |
| F(000) | 464 |
| Density (calculated), Mg/m3 | 1.393 |
| Absorption coefficient, mm−1 | 0.096 |
| Crystal size, mm3 | 0.30 × 0.16 × 0.11 |
| Theta range for data collection | 3.86 to 28.75°. |
| Index ranges | −9 <= h <= 9 |
|  | −15 <= k <= 15 |
|  | −16 <= l <= 17 |
| Reflections collected | 8739 |
| Independent reflections | 4527 |
|  | 0.026 |
| Completeness to theta = 28.75° | 83.6% |
| Absorption correction | None |
| Max. and min. transmission | 0.9895 and 0.9716 |
| Refinement method | Full-matrix least-squares on F2 |
| Data/restraints/parameters | 4527/0/298 |
| Goodness-of-fit on F2 | 1.069 |
| Final R indices [I > 2sigma(I)] | R1 = 0.044 |
|  | wR2 = 0.099 |
| R indices (all data) | R1 = 0.072 |
|  | wR2 = 0.112 |
| Largest diff. peak and hole, e.Å-3 | 0.25 and −0.24 |

Characterization of Form $HC_0$ by Thermal Analysis

Figure 28:
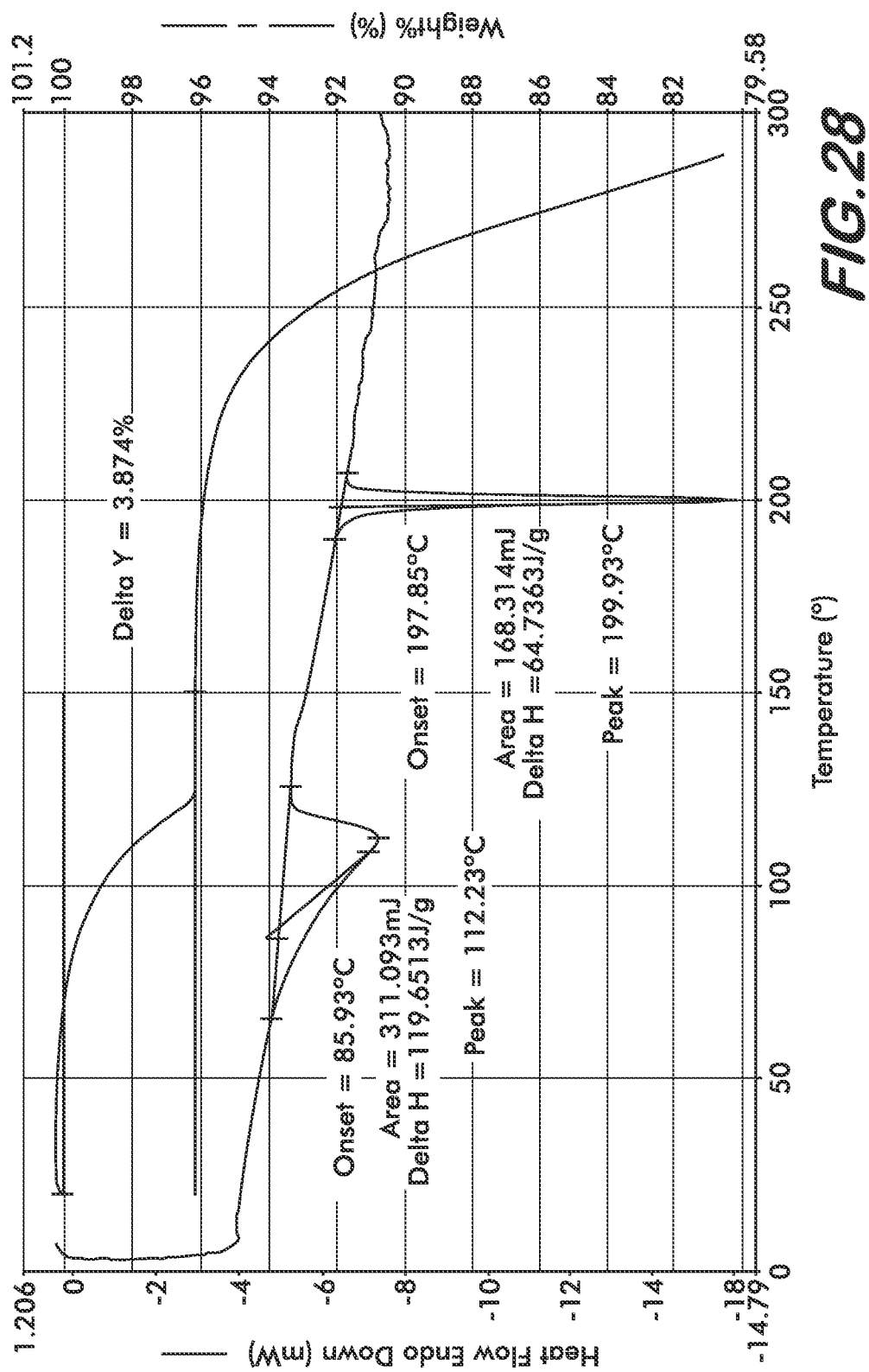
FIG. 28 is a Differential Scanning calorimetry (DSC) Thermogram and Thermo-Gravimetric Analysis (TGA) Thermogram overlay of Form $HC_0$.

The DSC thermogram of Form $HC_0$ shows the presence of two different endothermic peaks (FIG. 28 and Table 29). The monohydrate $HC_0$, when subjected to TGA, demonstrated an average weight loss of 3.9% between 50 and 120° C. This corresponds to the theoretical value for incorporation of one mole of water with one mole of Compound I of 4.1%.

TABLE 21

DSC onset and peak desolvation temperatures for Form $HC_0$

| Classification | Solvent | Solvate Weight loss (%) | Principal onset Temp./ ° C. | Peak Temp./ ° C. |
|---|---|---|---|---|
| $HC_0$ | Water | 3.9 | 85.9 | 112.2 |

Characterization of Form $HC_0$ by Water Sorption
Regular DVS (0 to 90% RH)

Figure 29:
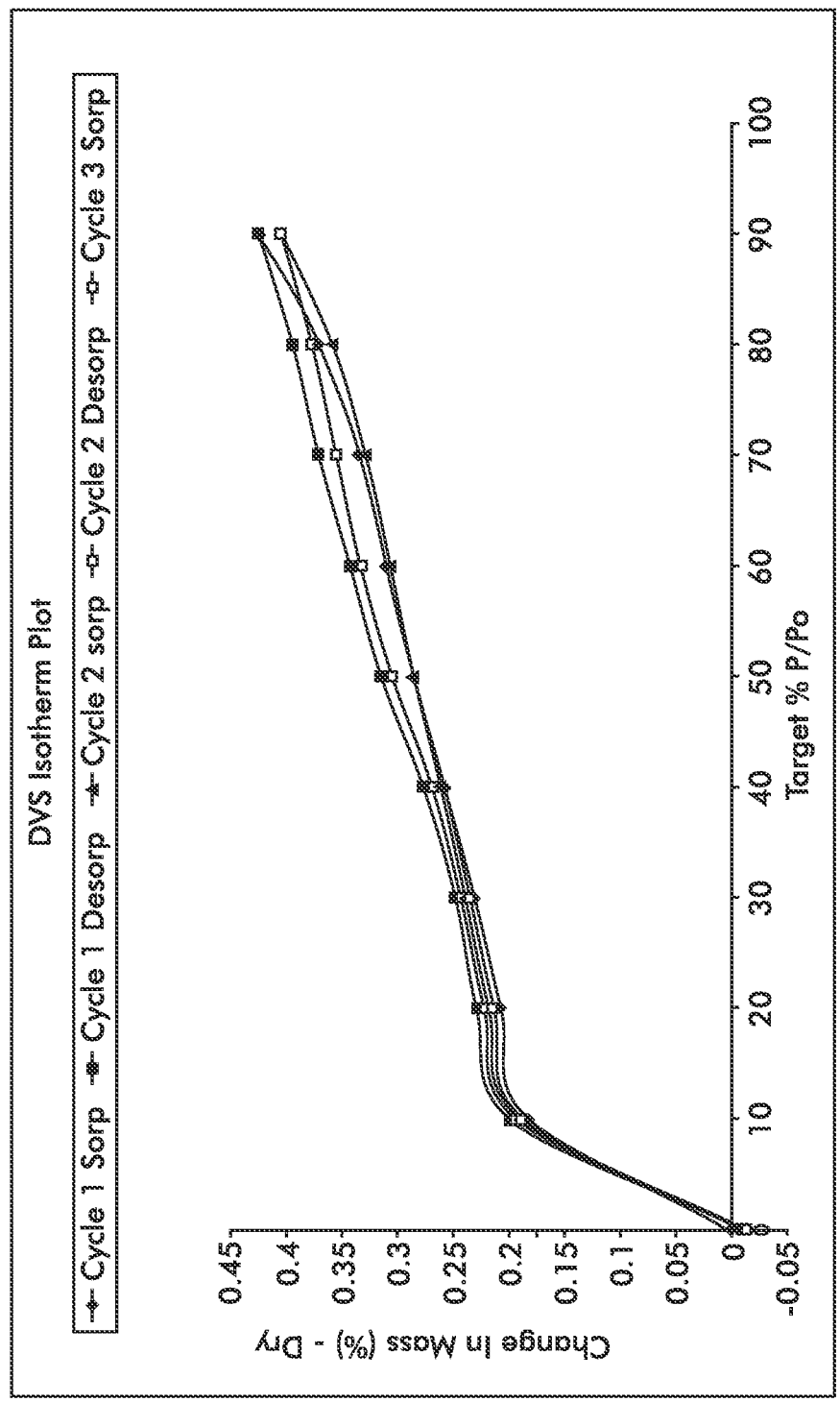
FIG. 29 is a Dynamic Vapor Sorption (DVS) regular isotherm plot of Form $HC_0$.
Figure 30:
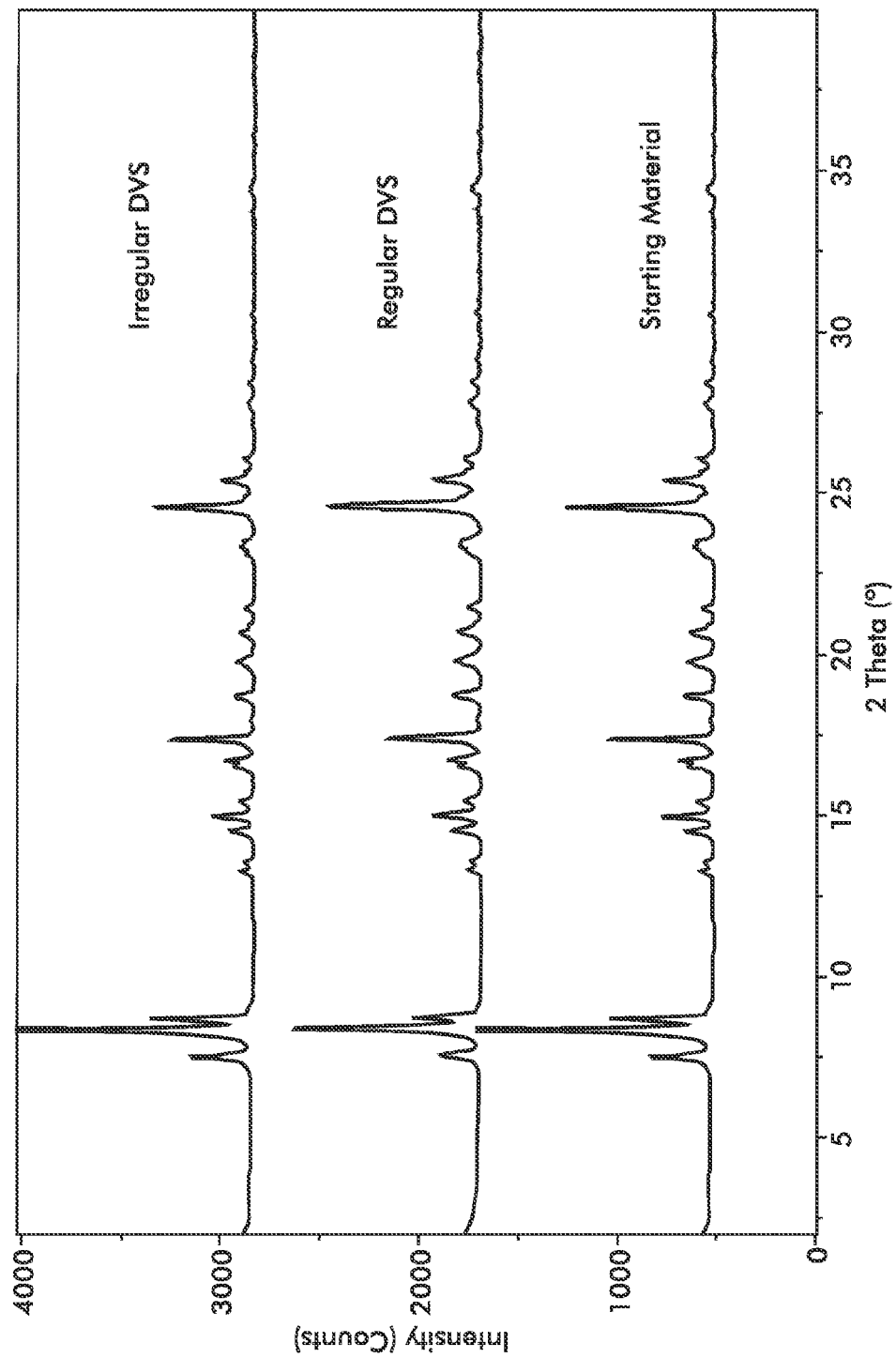
FIG. 30 depicts X-ray Powder Diffractograms (XRPD) of Form $HC_0$ before and after Dynamic Vapor Sorption (DVS) analysis.

The hysteresis gap suggests only surface water adsorption is occurring with a total uptake of 0.4% (FIG. 29 and Table 30). No significant changes were observed by XRPD re-analysis after DVS (FIG. 30).

TABLE 22

DVS data for Form $HC_0$ (Regular)

| Form | At 75% RH uptake | Total uptake at 90% RH |
|---|---|---|
| $HC_0$ | 0.3 | 0.4 |

Irregular DVS (90 to 0% RH)

Figure 31:
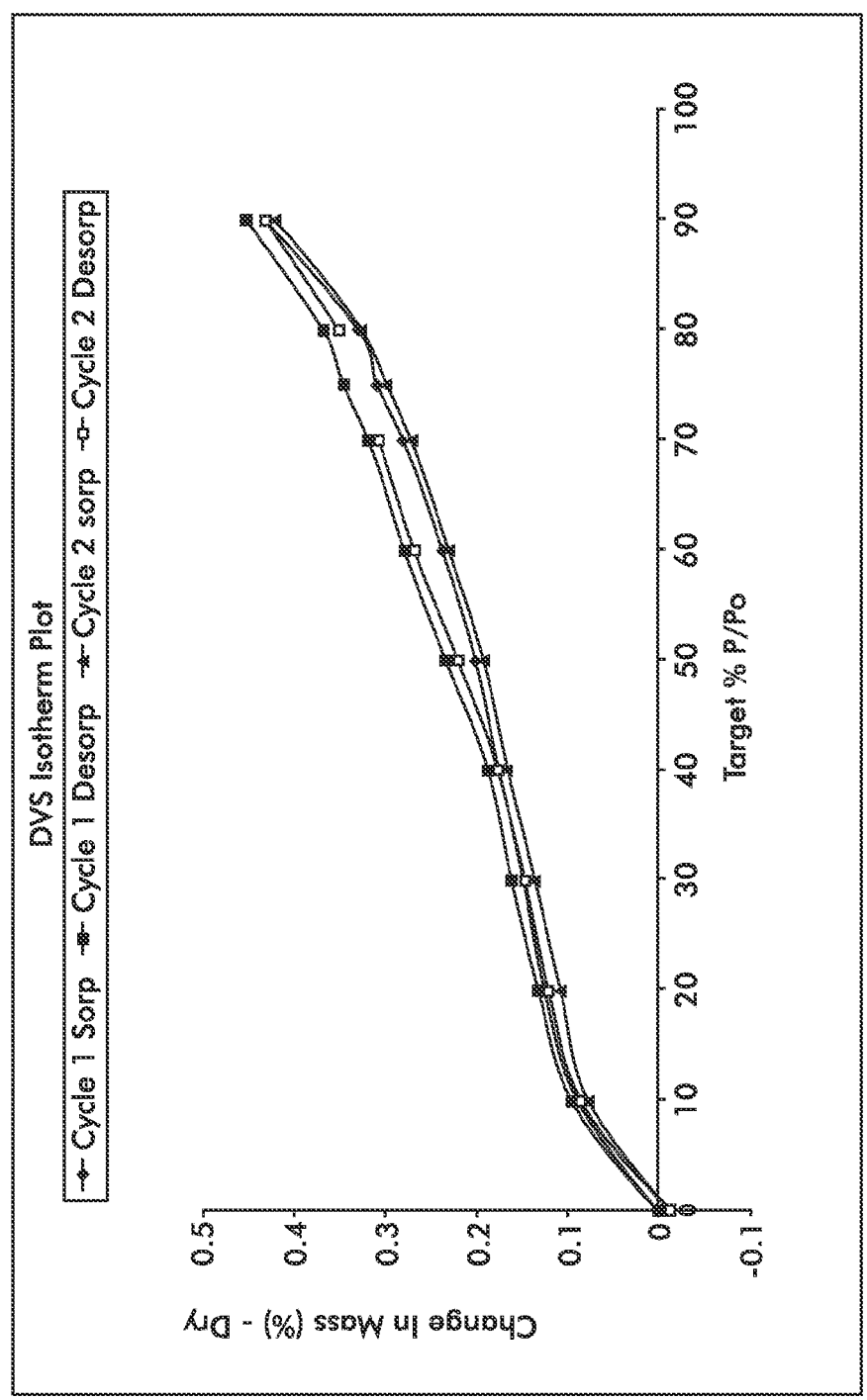
FIG. 31 is a Dynamic Vapor Sorption (DVS) irregular isotherm plot of Form $HC_0$.

The hysteresis gap suggests only surface water adsorption is occurring from 0-40% RH. From 40-90% RH there appears to be bulk absorption occurring (FIG. 31 and Table 31). No significant changes were observed by XRPD re-analysis after DVS (FIG. 30).

TABLE 23

DVS Data for Form $HC_0$ (Irregular)

| Form | At 75% RH uptake | Total uptake at 90% RH |
|---|---|---|
| $HC_0$ | 0.3 | 0.4 |

Characterization by FTIR and Raman Spectroscopy

Figure 32:
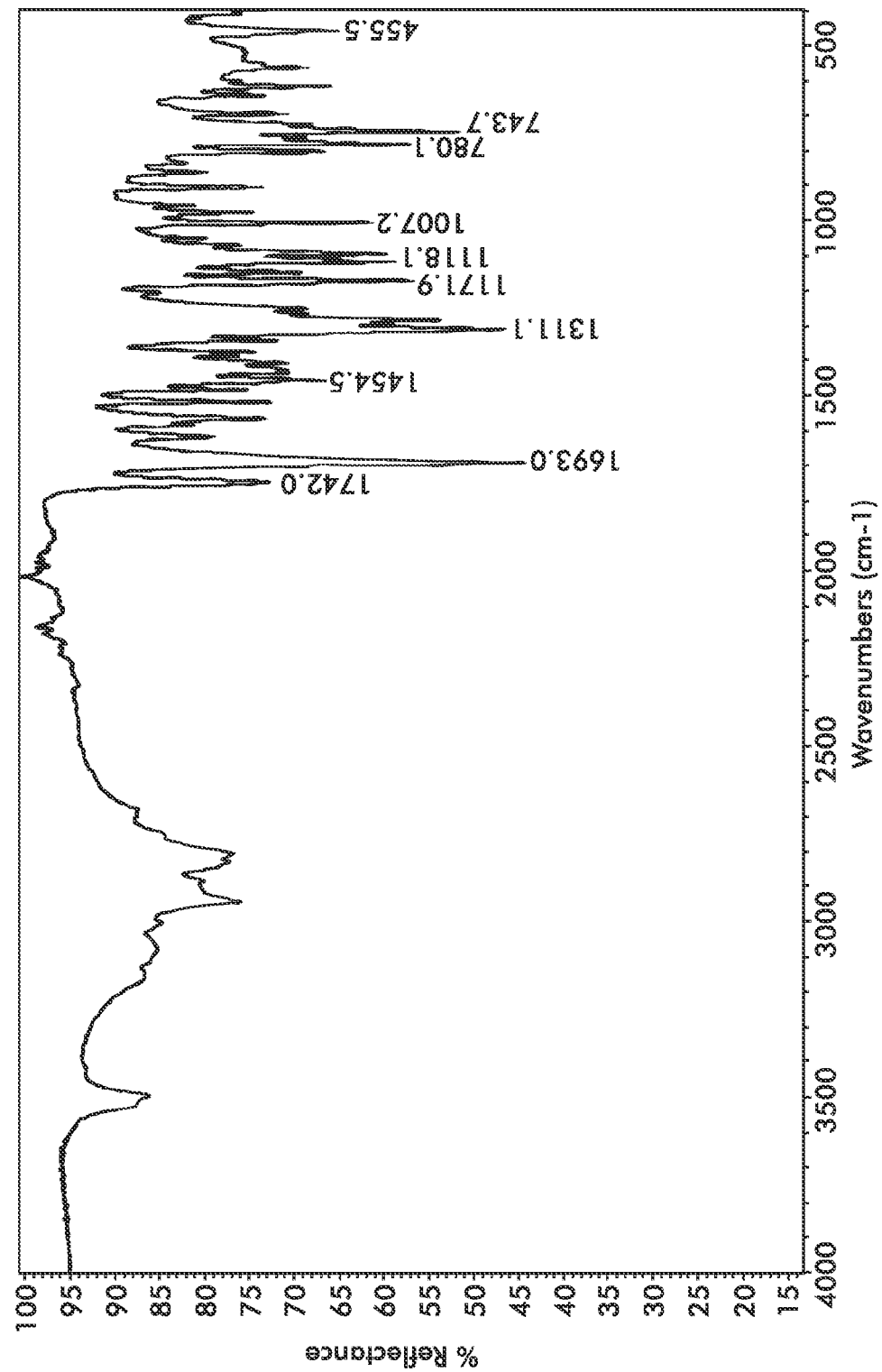
FIG. 32 is a Fourier Transform Infrared (FTIR) spectrum of Form $HC_0$.
Figure 33:
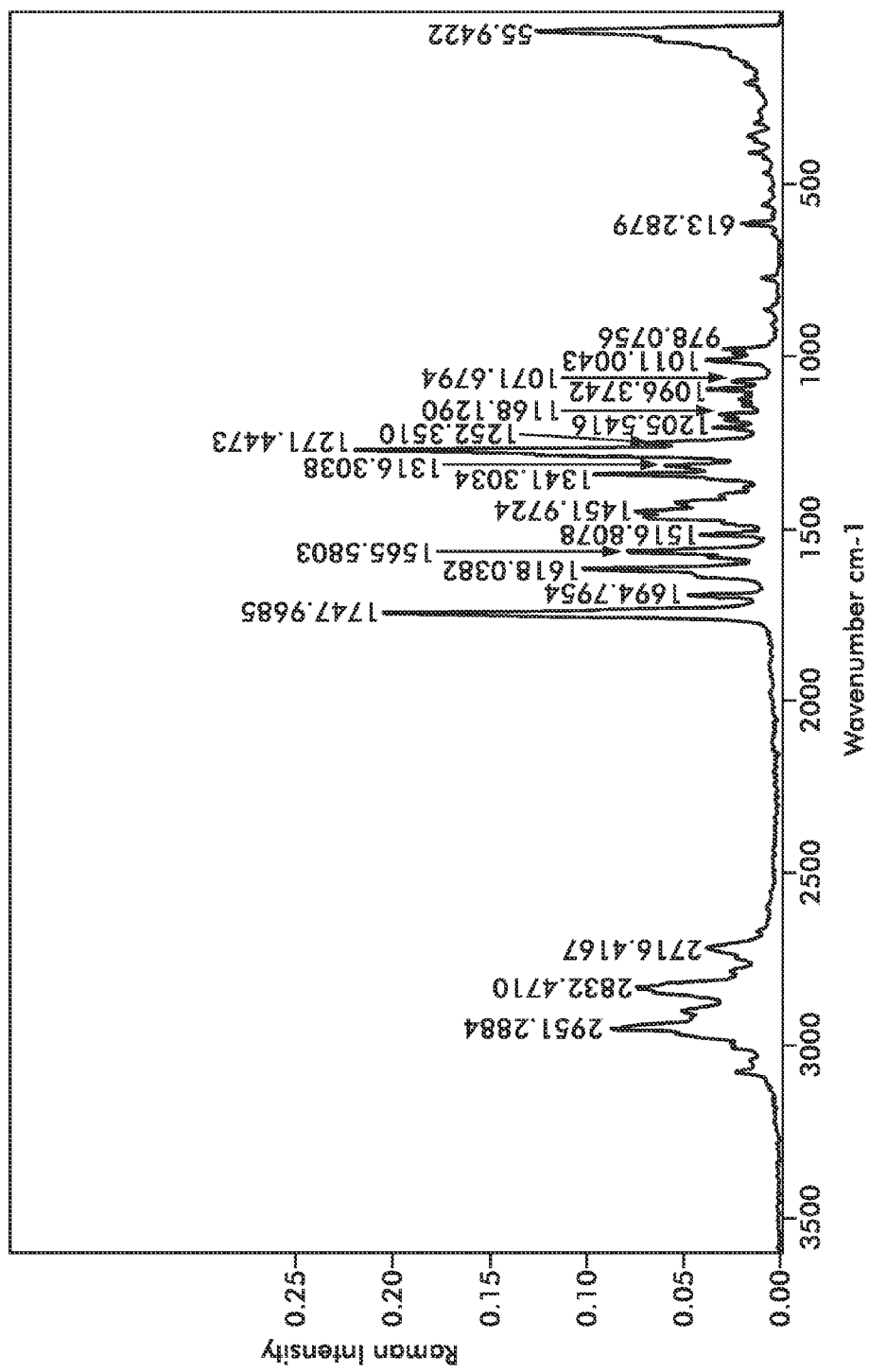
FIG. 33 is a Raman spectrum of Form $HC_0$.

The FTIR and Raman spectra of the crystalline Form $HC_0$ are shown in FIG. 32 and FIG. 33, respectively.

Preparation of Hydrate Form $HD_0$
Recrystallization from Acetone/Water

Form $HD_0$ was obtained as 40 mg of Lot 7 was added in 400 μL of acetone and 100 μL of water. The sample was heated to an initial temperature of 80° C. at a rate of 4.8° C./min and, after 30 minutes, cooled at 0.28° C./min to a final temperature of 5° C. and kept at that temperature for 18 h. The solid was isolated by filtration. The material was dried at 57° C. for 10 hours.

Recrystallization from 2-Methyl-2-Propanol

Form $HD_0$ was obtained as 0.54 g of Compound I in 55 mL of 2-methyl-2-propanol was almost completely dissolved by heating to the boiling point. The cloudy solution was syringe filtered using a 5μ nylon membrane syringe filter to give a clear solution (about 15% spilled and lost). The solution was concentrated to 25-30 mL and chilled for 4.5-5 hours at 2-8° C. to give a solid. The solid was melted in the oven at 50° C. and insoluble material isolated by suction filtration on a warm apparatus to prevent freezing of t-butyl alcohol. The solid that resulted was dried in a 50° C. oven for 2 hours to yield 0.42 g (75% recovery).

Recrystallization from Isopropyl Acetate

Form $HD_0$ was obtained as 0.45 g of Compound I in 7.5 mL of isopropyl acetate was stirred for 20 hours at room temperature with a magnetic stirring bar in a glass 20 mL scintillation vial with the cap fastened lightly. The slurry was suction filtered and the solid was allowed to dry over 110 hours exposed to air in the fume hood. The dried material weighed 380 mg (84% recovery).

Preparation of Crystal Structure

Single crystals were prepared by adding 200 mg of Lot 7 solid material to tetrahydrofuran for the monohydrate $HC_0$ to assure saturated conditions at the boiling point. The mixture was cooled and filtered through a 0.22μ nylon membrane filter into a warmed glass vial. The solution was cooled to 20° C.±0.2° C. in order to increase the supersaturation value and the homogeneous solution was left standing for several days.

Crystal Structure Determination by Single Crystal X-Ray Diffraction

Single crystal X-Ray data was obtained for $HD_0$. Cell parameters obtained from the data is presented in Table 32 below. The data were collected at a temperature of 103K using the ω-2θ scan technique. A colorless plate of $C_{24}H_{28}N_4O_4$ having approximate dimensions of 0.40×0.25× 0.08 mm was mounted on a glass fiber in a random orientation. The triclinic cell parameters (P−1, Z=2) and calculated volume are:

a = 8.171(2)  α = 111.173(18)°
b = 11.419(3)  β = 92.863(17)°
c = 12.7305(19)Å  γ = 102.07(2)°
V = 1072.8(4)Å$^3$.

TABLE 24

Crystal X-Ray Data Collection and Refinement Parameters for HD$_0$

| Identification code | Form HD$_0$ |
|---|---|
| Empirical formula | C$_{24}$H$_{28}$N$_4$O$_4$ |
| Formula weight | 436.50 |
| Temperature | 103(2) K |
| Wavelength, Å | 0.71073 |
| Crystal system, Space group | Triclinic, P-1 |
| Unit cell dimensions a, Å | 8.171(2) |
| b, Å | 11.419(3) |
| c, Å | 12.7305(19) |
| α, ° | 111.173(18) |
| β, ° | 92.863(17) |
| γ, ° | 102.07(2) |
| Volume | 1072.8(4) |
| Z | 2 |
| F(000) | 464 |
| Density (calculated), Mg/m3 | 1.351 |
| Absorption coefficient, mm−1 | 0.094 |
| Crystal size, mm3 | 0.40 × 0.25 × 0.08 |
| Theta range for data collection | 3.95 to 26.56°. |
| Index ranges | −10 <= h <= 10 |
|  | −14 <= k <= 14 |
|  | −15 <= l <= 15 |
| Reflections collected | 9366 |
| Independent reflections | 4373 |
|  | 0.040 |
| Completeness to theta = 28.75° | 97.7% |
| Absorption correction | None |
| Max. and min. transmission | 0.9926 and 0.9635 |
| Refinement method | Full-matrix least-squares on F2 |
| Data/restraints/parameters | 4373/0/302 |
| Goodness-of-fit on F2 | 1.166 |
| Final R indices [I > 2sigma(I)] | 0.051 |
|  | 0.099 |
| R indices (all data) | 0.087 |
|  | 0.113 |
| Largest diff. peak and hole, e.Å-3 | 0.24 and −0.25 |

Characterization of Form HD$_0$ by Thermal Analysis

Figure 34:
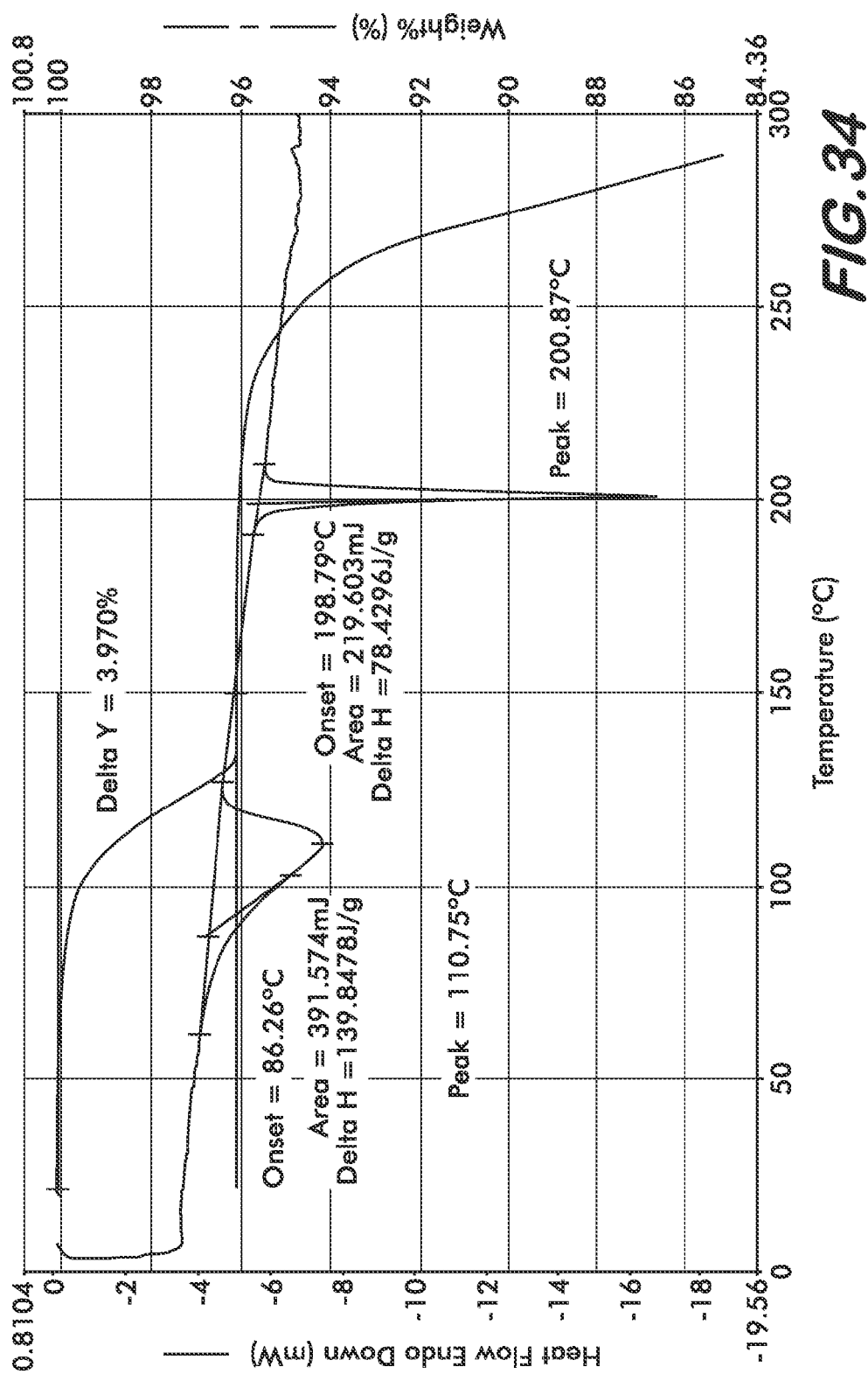
FIG. 34 is a Differential Scanning calorimetry (DSC) Thermogram and Thermo-Gravimetric Analysis (TGA) Thermogram overlay of Form $HD_0$.

The DSC thermograms of Form HD$_0$ show the presence of two different endothermic peaks (FIG. 34 and Table 33). The monohydrate HD$_0$, when subjected to TGA, demonstrated an average weight loss of 4.0% between 50 and 120° C. The theoretical value for incorporation of one mole of water with one mole of Compound I is 4.1%.

TABLE 25

Onset and DSC Peak of desolvation temperatures of Form HD$_0$

| Classification | Solvent | Solvate Weight loss (%) | Principal onset Temp./ ° C. | Peak Temp./ ° C. |
|---|---|---|---|---|
| HD$_0$ | Water | 4.0 | 86.3 | 110.7 |

Characterization of Form HD$_0$ by Water Sorption
Regular DVS (0 to 90% RH)

Figure 35:
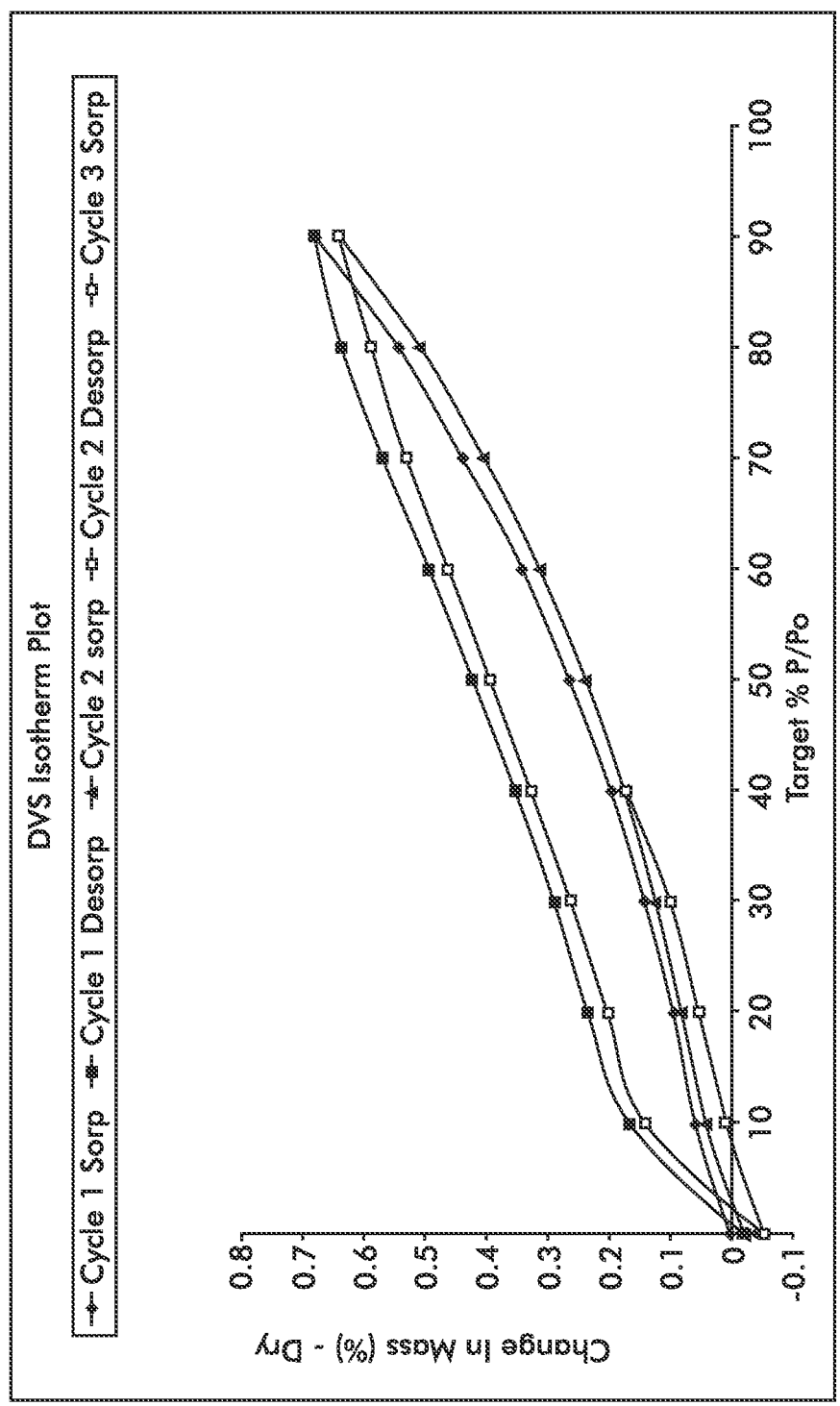
FIG. 35 is a Dynamic Vapor Sorption (DVS) regular isotherm plot of Form $HD_0$.
Figure 36:
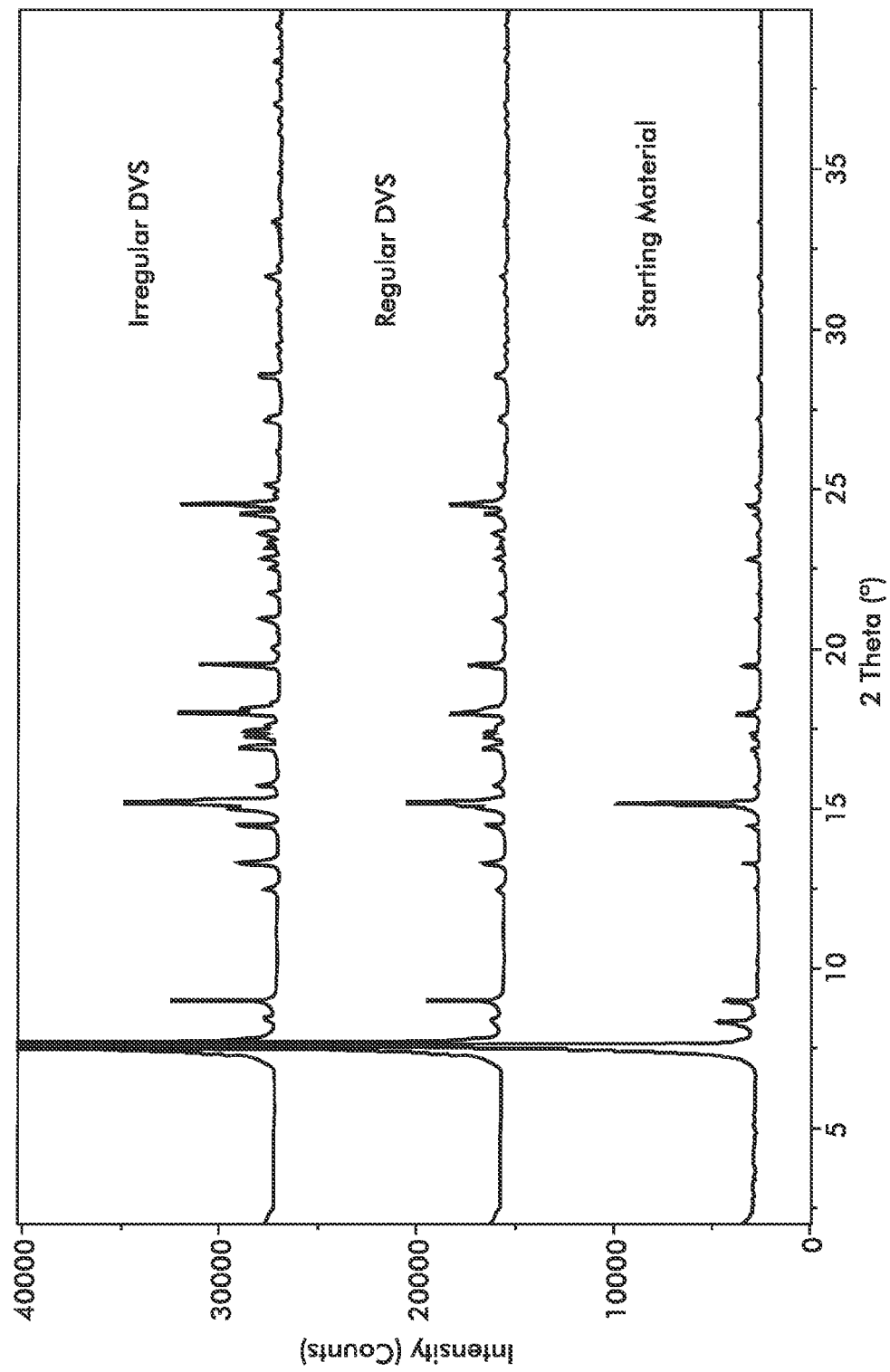
FIG. 36 depicts X-ray Powder Diffractogram (XRPD) of Form $HD_0$ before and after Dynamic Vapor Sorption (DVS) analysis.

The sample mass only increases 0.6% at 90% RH. The hysteresis gap suggests that surface water adsorption and bulk absorption is occurring (FIG. 35 and Table 34). No significant changes were observed by XRPD re-analysis after DVS (FIG. 36).

TABLE 26

DVS data for form HD$_0$ (regular)

| Form | At 75% RH uptake | Total uptake at 90% RH |
|---|---|---|
| HD$_0$ | 0.4 | 0.6 |

Irregular DVS (90 to 0% RH)

Figure 37:
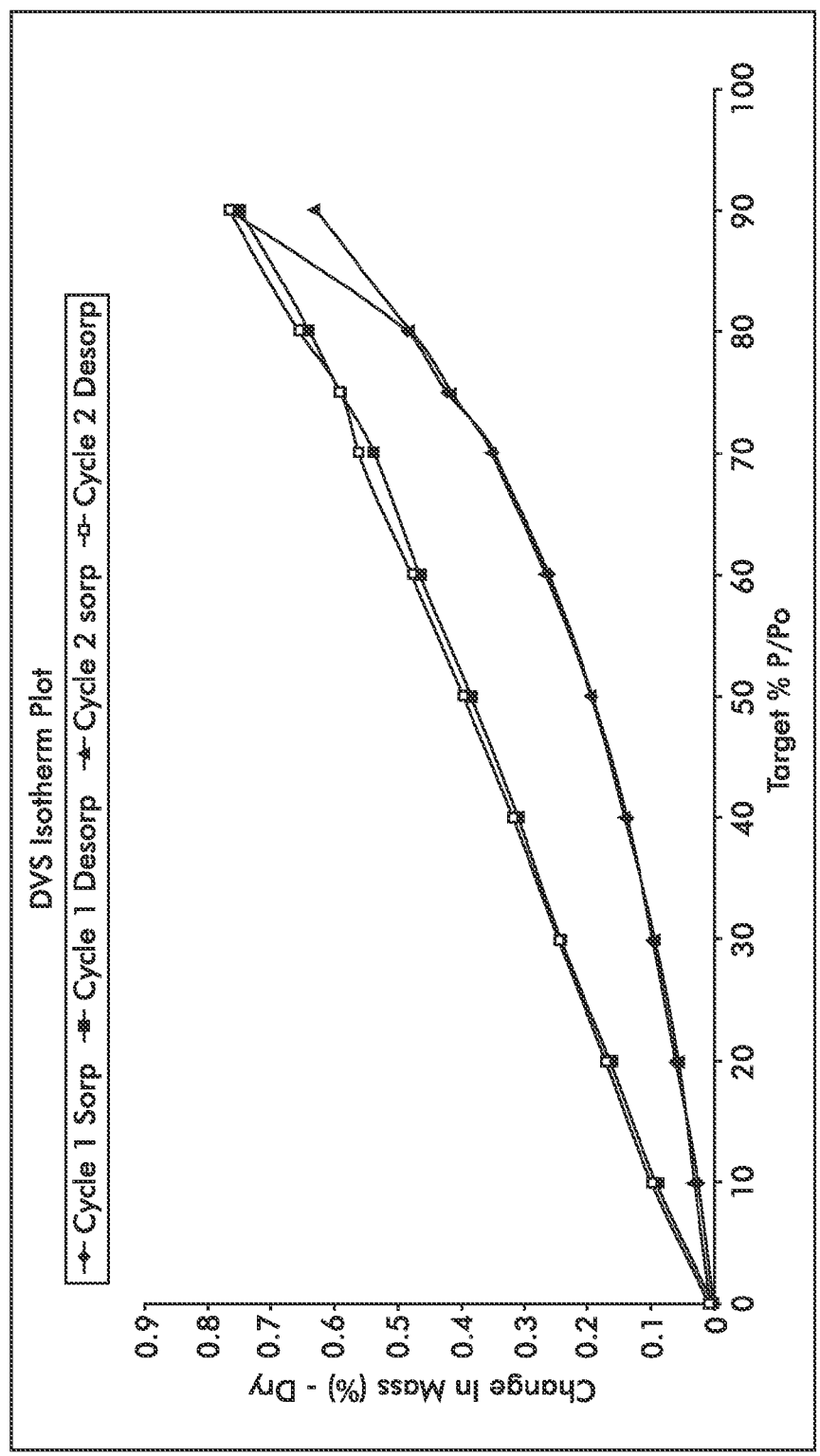
FIG. 37 is a Dynamic Vapor Sorption (DVS) irregular isotherm plot of Form $HD_0$.

The sample mass only increases 0.8% at 90% RH. The hysteresis gap suggests that surface water adsorption and limited bulk absorption is occurring (FIG. 37 and Table 26). No significant changes were observed by XRPD re-analysis after DVS (FIG. 27).

TABLE 27

DVS data for form HD$_0$ (irregular)

| Form | At 75% RH uptake | Total uptake at 90% RH |
|---|---|---|
| HD$_0$ | 0.4 | 0.8 |

Characterization of Form HD$_0$ by FTIR and Raman Spectrometry

Figure 38:
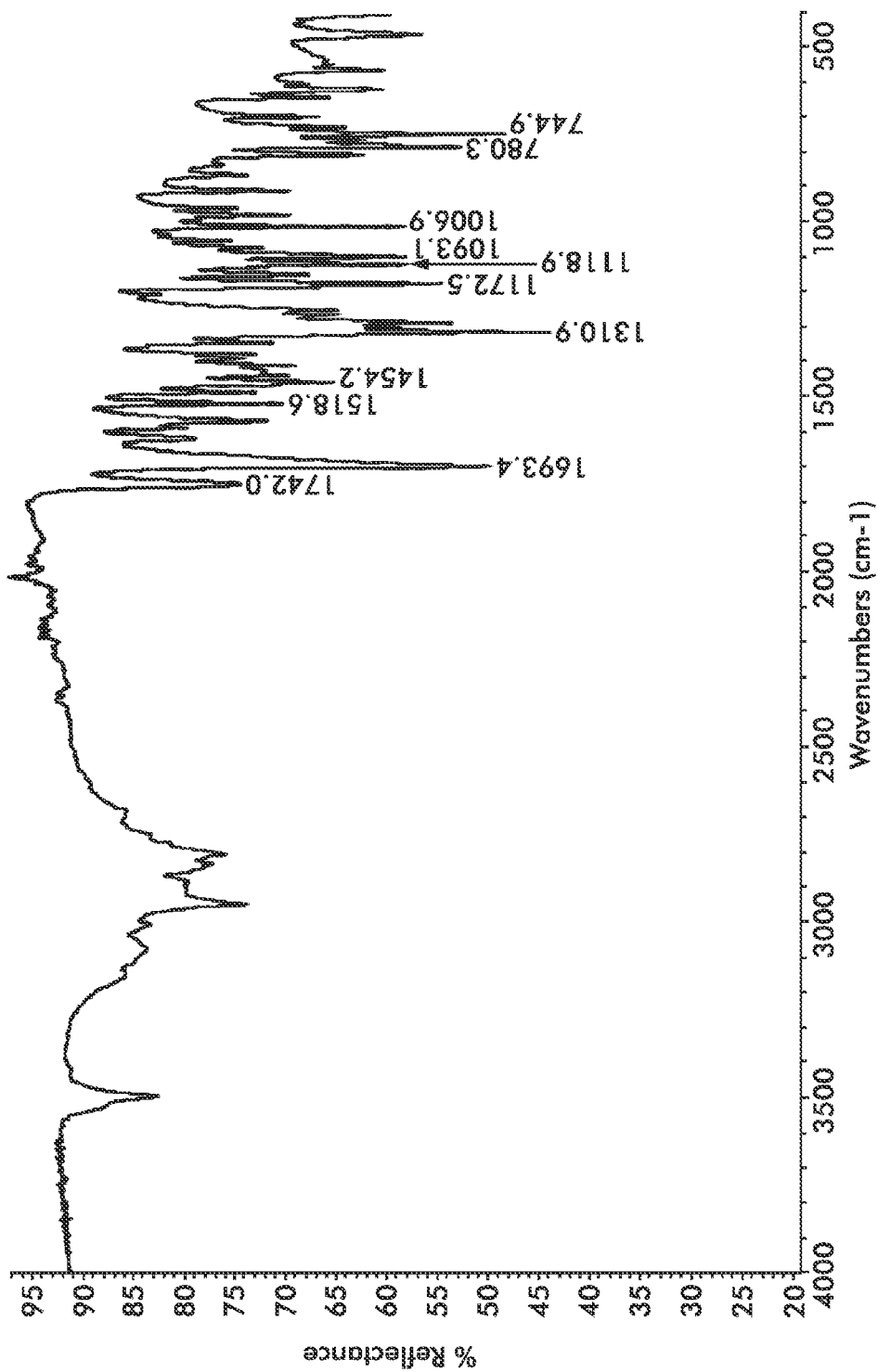
FIG. 38 is a Fourier Transform Infrared (FTIR) spectrum of Form $HD_0$.
Figure 39:
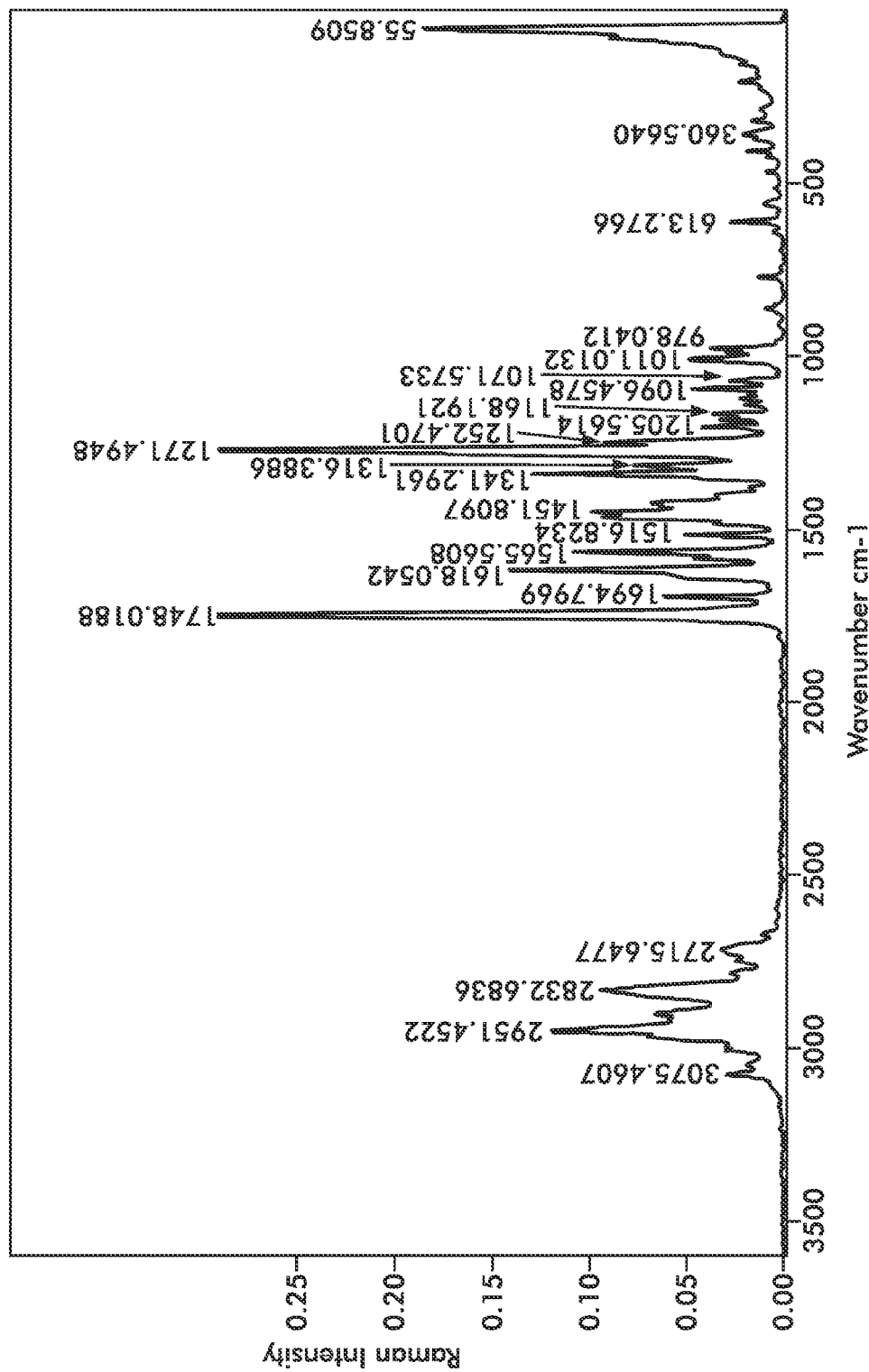
FIG. 39 is a Raman spectrum of Form $HD_0$.
Figure 40:
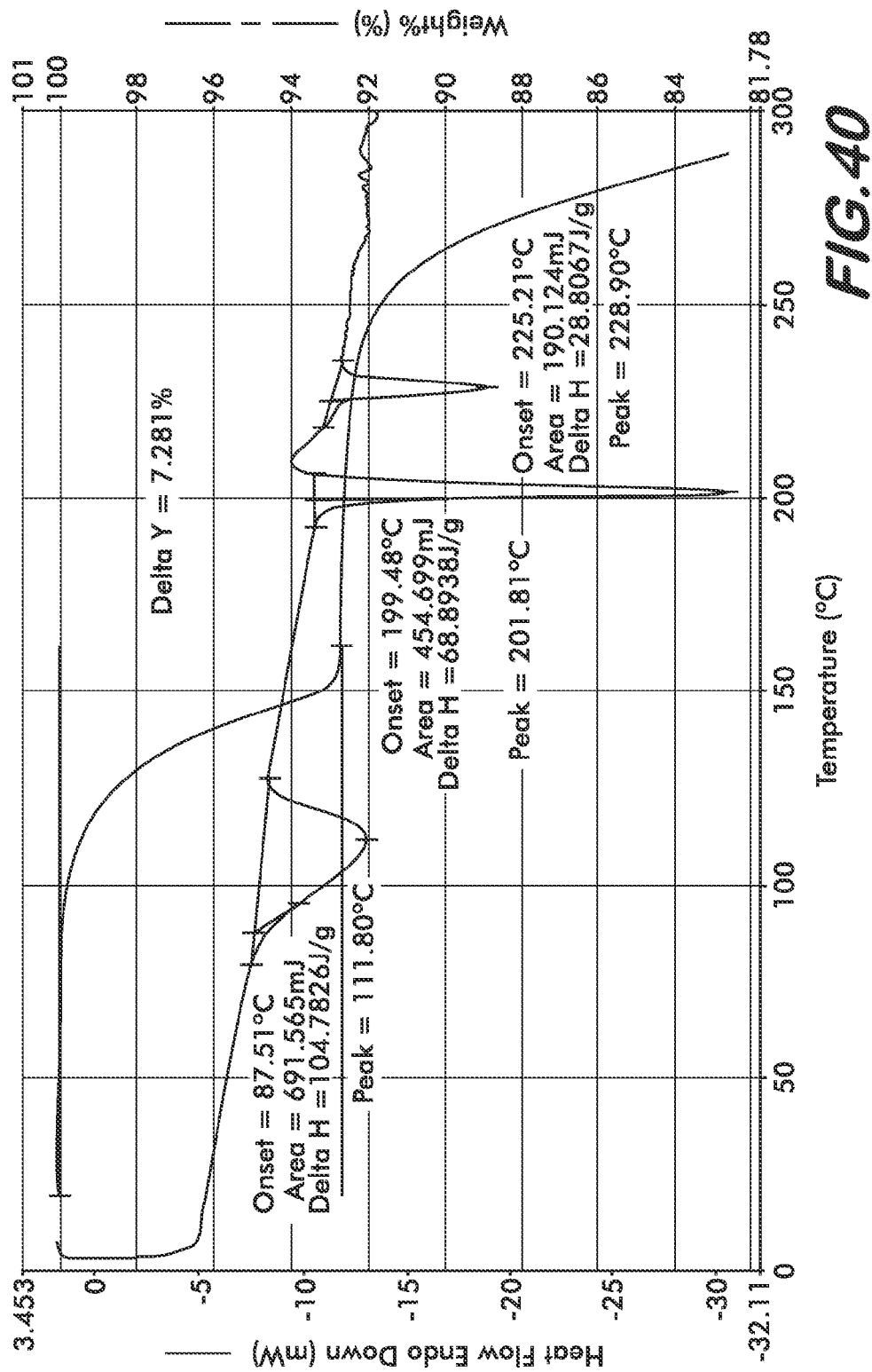
FIG. 40 is a Differential Scanning calorimetry (DSC) Thermogram and Thermo-Gravimetric Analysis (TGA) Thermogram overlay of Form $S2_0$.

The FTIR and Raman spectra of the crystalline Form HD$_0$ are shown in FIG. 38 and FIG. 39, respectively.
Solvate Forms of Compound I
Recrystallization from Methanol Form S2$_0$ was obtained as 40 mg of Lot 7 was added in 400 μL of methanol. The sample was slurried at 20° C.±0.2 for 3 days. The solid was isolated by filtration. The material was dried at 57° C. for 10 hours.
Recrystallization from 2-Propanol Form S3$_0$ was obtained as 40 mg of Lot 7 was added in 400 μL of 2-propanol. The sample was slurried at 20° C.±0.2 for 3 days. The solid was isolated by filtration. The material was dried at 57° C. for 10 hours.
Recrystallization from Ethanol Form S4$_0$ was obtained as 40 mg of Lot 7 was added in 400 μL of ethanol. The sample was slurried at 20° C.±0.2 for 3 days. The solid was isolated by filtration. The material was dried at 57° C. for 10 hours.
Preparation of Crystal Structure Single crystals were prepared by adding 200 mg of Lot 7 solid material to ethanol for the ethanolate to assure saturated conditions at the boiling point. The mixture was cooled and filtered through a 0.22 μm nylon membrane filter into a warmed glass vial. The solution was cooled to 20° C.±0.2° C. in order to increase the supersaturation value and the homogeneous solution was left standing for several days.
Recrystallization from N—N-dimethylformamide Form S5$_0$ was obtained as 40 mg of Lot 7 was added in 400 μL of N—N-dimethylformamide (DMF). The sample was slurried at 20° C.±0.2 for 3 days. The solid was isolated by filtration. The material was dried at 57° C. for 10 hours.
Recrystallization from Ethylene Glycol Form S6$_0$ was obtained as 40 mg of Lot 7 was added in 400 μL of ethylene glycol. The sample was heated to an initial temperature of 80° C. at a rate of 4.8° C./min and, after 30 minutes, cooled at 0.28° C./min to a final temperature of 5° C. and kept at that temperature for 18 hours. The solid was isolated by filtration. The material was dried at 57° C. for 10 hours.
Recrystallization from Pyridine Form S7$_0$ was obtained as 40 mg of Lot 7 was added in 400 μL of pyridine. The sample was heated to an initial temperature of 80° C. at a rate of 4.8° C./min and, after 30 minutes, cooled at 0.28° C./min to a final temperature of 5° C. and kept at that temperature for 18 hours. The solid was isolated by filtration. The material was dried at 57° C. for 10 hours.

Recrystallization from 1-propanol

Form $S9_0$ was obtained as 40 mg of Compound I in 1-propanol to assure saturated conditions at the boiling point. The mixture was cooled and filtered through a 5μ nylon membrane filter into a warmed glass vial. The solution was cooled to RT and placed in a refrigerator (ca. 4° C.) until crystal formation appeared to reach completion as determined by visual inspection. Samples difficult to decant were centrifuged at 12000 rpm for four minutes.

Recrystallization from N—N-dimethylacetamide

Form $S10_0$ was obtained as 40 mg of Lot 7 was added in 400 μL of N—N-dimethylacetamide (DMA). The sample was slurried at 20° C.±0.2 for 3 days. The solid was isolated by filtration. The material was dried at 57° C. for 10 hours.

Recrystallization from Isobutanol

Form $S12_0$ was obtained as 40 mg of Compound I in isobutanol to assure saturated conditions at the boiling point. The mixture was cooled and filtered through a 5μ nylon membrane filter into a warmed glass vial. The solution was cooled to RT and placed in a refrigerator (ca. 4° C.) until crystal formation appeared to reach completion as determined by visual inspection. Samples difficult to decant were centrifuged at 12000 rpm for four minutes.

Crystal Structure Determination by Single Crystal X-Ray Diffraction

Single crystal X-Ray data were obtained for Form $S4_0$. Cell parameters obtained from the data are presented in Table 28.

TABLE 28

Crystal X-ray data collection and refinement parameters for ethanol solvate $S4_0$

|  | From Single Crystal | After Rietveld on $S4_0$ |
|---|---|---|
| Unit cell dimensions a, Å | 8.828(3) | 8.996(7) |
| b, Å | 11.652(3) | 11.813(2) |
| c, Å | 13.234(6) | 13.191(9) |
| α, ° | 115.01(3) | 114.28(1) |
| β, ° | 108.09(3) | 108.52(8) |
| γ, ° | 93.00(2) | 92.56(0) |

Thermal Analysis of the Solvate Forms of Compound I

Figure 48:
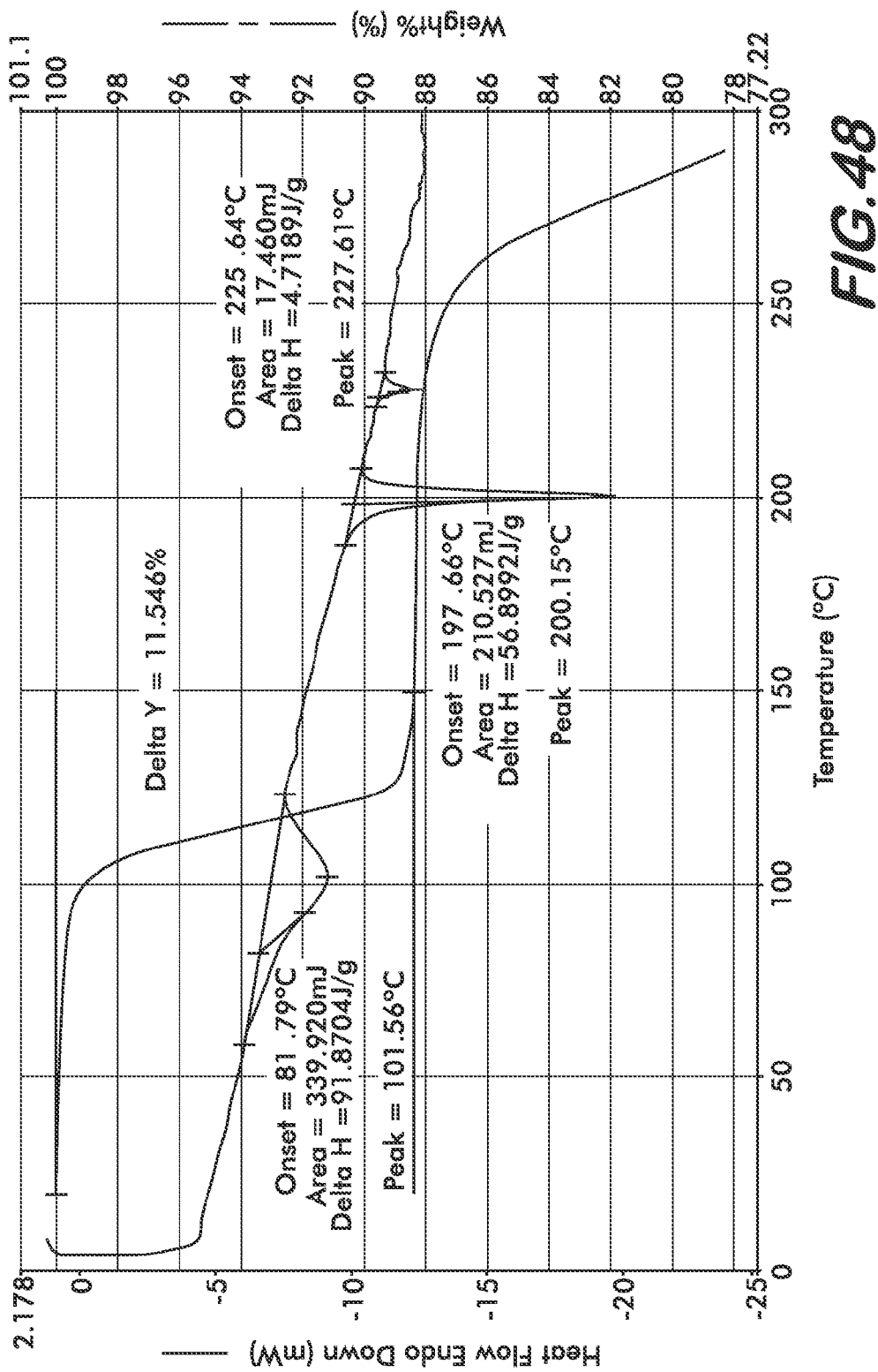
FIG. 48 is a Differential Scanning calorimetry (DSC) Thermogram and Thermo-Gravimetric Analysis (TGA) Thermogram overlay of Form $S12_0$.

DSC thermal curves showed the presence of a large and broad endotherm before the melting point of Compound I for all the solvates. TGA studies showed that these endotherms can be attributed to a desolvation process for Forms $S2_0$ (FIG. 40), $S3_0$ (FIG. 41), $S4_0$ (FIG. 42), $S5_0$ (FIG. 43), $S6_0$ (FIG. 44), $S7_0$ (FIG. 45), $S9_0$ (FIG. 46), $S10_0$ (FIG. 47), and $S12_0$ (FIG. 48). The calculation of the solvent weight loss led for these solvents is presented in Table 29.

TABLE 29

DSC onset and peak desolvation temperatures for solvate forms

| Form | Solvent | Solvate Weight loss (%) Experimental | Solvate Weight loss (%) Theory 1:1 | Principal onset Temp./ ° C. | Peak Temp./ ° C. |
|---|---|---|---|---|---|
| $S2_0$ | Methanol | 7.3 | 7.1 | 87.5 | 111.8 |
| $S3_0$ | 2-propanol | 10.41 | 12.5 | 78.0 | 104.9 |
| $S4_0$ | Ethanol | 8.7 | 9.9 | 109.9 | 122.8 |
| $S5_0$ | DMF | 13.0 | 14.9 | 127.0 | 147.0 |
| $S6_0$ | Ethylene glycol | 6.16 | 12.9 | 139.9 | 156.6 |
| $S7_0$ | Pyridine | 3.53 | 15.9 | 128.0 | 141.9 |
| $S9_0$ | 1-propanol | 12.42 | 12.5 | 118.4 | 129.6 |

TABLE 29-continued

DSC onset and peak desolvation temperatures for solvate forms

| Form | Solvent | Solvate Weight loss (%) Experimental | Solvate Weight loss (%) Theory 1:1 | Principal onset Temp./ ° C. | Peak Temp./ ° C. |
|---|---|---|---|---|---|
| $S10_0$ | DMA | 19.42 | 17.2 | 135.0 | 156.0 |
| $S12_0$ | Isobutanol | 11.54 | 15.0 | 81.8 | 132.5 |

Crystal Structure Determination of Compound I Monohydrates

The hydrate Forms $HC_0$ and $HD_0$ are isostructural, which means that the individual 'isomorphic solvates' crystallize in the same space group with only small distortions of the unit cell dimensions and the same type of molecular network of the host molecules (Reutzel-Edens S. M., Newman A W., Polymorphism in the Pharmaceutical Industry, Edited by Rolf Hilfiker, 2006, Wiley-VCH Verlag GmbH & Co. KGaA ISBN: 9783527311460). Form $HC_0$ and Form $HD_0$ differ in the conformation of the tetrahydropyrazine ring. The X-ray powder diffraction pattern of the two hydrate forms could be successfully refined using Rietveld techniques (Rietveld H. M. "A profile refinement method for nuclear and magnetic structures", *Journal of Applied Crystallography* 2: 65-71 (1969)) with the single crystal parameters as the starting point. Details of the cell data, data collection and refinement are summarized in Table 28 and Table 32.

FTIR and FT-Raman Method for Identification Assay

Comparison of the FTIR and Raman spectra in FIG. 20 and FIG. 21 for Form $A_0$ and for the hydrates (FIG. 26, FIG. 32, FIG. 38) and (FIG. 27, FIG. 33, FIG. 39) show little difference except in the carbonyl stretching region for the FTIR.

In $A_0$, a peak occurred at 1765 cm$^{-1}$ of medium intensity for the FTIR and 1770 cm$^{-1}$ for the Raman. In the hydrate forms, a peak occurred in this region at 1742 cm$^{-1}$ of medium intensity for FTIR and 1754-1695 cm$^{-1}$ for the Raman. This absorption peak is assigned to the imide carbonyl functionality contained within the five-membered ring of the Compound I structure. This difference is large enough that it could be used for identification of nearly pure solid state forms. IR spectra for hydrate forms and $A_0$ show some differences but the most significant concerns the broad band (3800-2800) present in hydrate forms due to the stretching of the —OH bond in the hydroxyl group.

TABLE 30

Frequencies (cm$^{-1}$) and attribution of fundamental vibration for Compound I for FTIR

| Form | -Hydroxyl (cm$^{-1}$) | -Carbonyl (cm$^{-1}$) |
|---|---|---|
| $A_0$ | 3349.9 | 1765.3 |
| $HA_0$ | 3498.2 | 1742.0 |
| $HC_0$ | 3498.2 | 1742.0 |
| $HD_0$ | 3498.2 | 1742.0 |

TABLE 31

Frequencies (cm$^{-1}$) and attribution of fundamental vibration for Compound I for Raman

| Form | -Carbonyl (cm$^{-1}$) | -Carbonyl (cm$^{-1}$) |
|---|---|---|
| $A_0$ | 1770 | 1638 |
| $HA_0$ | 1754 | 1699 |

TABLE 31-continued

Frequencies (cm$^{-1}$) and attribution of fundamental vibration for Compound I for Raman

| Form | -Carbonyl (cm$^{-1}$) | -Carbonyl (cm$^{-1}$) |
|---|---|---|
| HC$_0$ | 1752 | 1696 |
| HD$_0$ | 1748 | 1695 |

Relationship between Solid State Forms

Relative Stability of Slurries of Compound I in Water

When hydrate HA$_0$ and A$_0$ are crystallized from aqueous media, a mixture of Forms HC$_0$+HD$_0$ is produced (Table 32).

TABLE 32

Crystal forms obtained per well plate of Compound I

| Form of the Starting Material | Solvent | Volumes of Water | Forms Found |
|---|---|---|---|
| HA$_0$ | | 0.175 | HC$_0$, HD$_0$ |
| A$_0$ | Methyl acetate | 0 | A$_0$ |
| A$_0$ | Methyl acetate | 0.175 | HC$_0$, HD$_0$ |
| A$_0$ | Methyl acetate | 0.25 | HC$_0$, HD$_0$ |
| A$_0$ | Methyl acetate | 1 | HC$_0$, HD$_0$ |
| A$_0$ | Methyl acetate | 1.5 | HC$_0$, HD$_0$ |

Two ml of water was added to a few milligrams of Compound I forms. The samples were slurried overnight. A small sample of solid was removed and analyzed by XRPD. After slurrying, Forms HA$_0$ and A$_0$ were found to have converted to the hydrate forms (mixture of Forms HC$_0$ and HD$_0$) under all of the conditions investigated (Table 33, Table 34, Table 35, Table 36 and Table 37). The hydrate form appears to be more thermodynamically stable than Form A$_0$ between 5 and 45° C.

TABLE 33

XRPD analysis of residual solid from thermodynamic solubility experiments of Form A$_0$ in water at 5° C.

| Form A$_0$/mg | Time (days) | Forms Found |
|---|---|---|
| 15.9 | 1 | HC$_0$, HD$_0$ |
| 14.1 | 4 | HC$_0$, HD$_0$ |

TABLE 34

XRPD analysis of residual solid from thermodynamic solubility experiments of Form HA$_0$ and Form HB$_0$ (mixture of HC$_0$ and HD$_0$) in water at RT

| HB$_0$/mg | HA$_0$/mg | Time (days) | Forms Found |
|---|---|---|---|
| 5.05 | 6.08 | 1 | HA$_0$, HC$_0$, HD$_0$ |
| 4.91 | 4.98 | 9 | HC$_0$, HD$_0$ |
| 4.94 | 5.02 | 10 | HC$_0$, HD$_0$, trace of HA$_0$ |
| 5.34 | 5.57 | 14 | HC$_0$, HD$_0$, trace of HA$_0$ |

TABLE 35

XRPD analysis of residual solid from thermodynamic solubility experiments of Form HA$_0$ and Form HC$_0$ in water at RT

| HC$_0$/mg | HA$_0$/mg | Time (days) | Forms Found |
|---|---|---|---|
| 5.34 | 5.35 | 1 | HA$_0$, HC$_0$ |
| 5.23 | 6.04 | 2 | HA$_0$, HD$_0$ |
| 5.19 | 5.21 | 5 | HC$_0$, HD$_0$ |

TABLE 36

XRPD analysis of residual solid from thermodynamic solubility experiments Form HA$_0$ and Form HD$_0$ in water at RT

| HD$_0$/mg | HA$_0$/mg | Time (day s) | Forms Found |
|---|---|---|---|
| 5.48 | 5.83 | 1 | HA$_0$, HD$_0$ |
| 5.43 | 5.06 | 2 | HA$_0$, HC$_0$ |
| 5.10 | 5.18 | 5 | HD$_0$, HC$_0$ |
| 5.41 | 6.01 | 14 | HD$_0$, HC$_0$ |

TABLE 37

XRPD analysis of residual solid from thermodynamic solubility experiments Form A$_0$ at 45° C. in water

| Form A$_0$/mg | Time (days) | Forms Found |
|---|---|---|
| 14.3 | 1 | HA$_0$, HC$_0$ |

Relative Stability of Monohydrates

By measuring the thermodynamic solubility of two polymorphs (Form HC$_0$ and Form HD$_0$) at a practical range of temperatures, it is possible to determine which is the more stable and whether the relationship between them is monotropic or enantiotropic. Experiments were set up to measure the thermodynamic solubility of these monohydrate forms at room temperature and 55° C. in ethyl acetate, MTBE and 1-pentanol. These solvents were selected as Compound I did not form solvates in these solvents during the polymorph screen.

TABLE 38

XRPD analysis of residual solid from thermodynamic solubility experiments of monohydrate forms

| Solvent | Temperature | XRPD Analysis after 1 days | XRPD Analysis after 3 days | Solubility (mg/mL) |
|---|---|---|---|---|
| Ethyl acetate | RT | HD$_0$ > HC$_0$ | HD$_0$ | 1.7 |
| Ethyl acetate | 55° C. | HD$_0$ | HD$_0$ > HC$_0$ | 2.6 |
| MTBE | RT | HD$_0$, HC$_0$ | HD$_0$, HC$_0$ | 1.8 |
| MTBE | 55° C. | HD$_0$ and Form HC$_0$ | HD$_0$, HC$_0$ | 1.9 |
| 1-pentanol | RT | HD$_0$ > HC$_0$ | HD$_0$ > HC$_0$ | 6.8 |
| 1-pentanol | 55° C. | HD$_0$ > HC$_0$ | HD$_0$ > HC$_0$ | 28.7 |

Results summarized in Table 38 show that for the solvents used and the temperature ranges explored, the solubility values of the two hydrated polymorphs are very close but always higher for Form HD$_0$. It does indicate that between room temperature and 55° C. in solution Form HD$_0$ is more thermodynamically stable than Form HC$_0$ and form HA$_0$.

Solid State Stress Stability

Stress stability studies were performed to get a timely impression of the influence of temperature and humidity on form stability. A stability-indicating HPLC assay method was developed for quantitation of Compound I and its major degradation product, 7-methoxy-1,2,3,11-tetrahydro-5,11-diaza-benzo[a]trindene-4,6-dione, previously referred to as "Compound E". The developed method is specific, accurate, precise and robust. The procedure permitted an accurate and quantitative determination of Compound I and Compound E. All the degradation products formed during forced decomposition studies were well separated from the main peaks demonstrating that the developed method was specific and stability-indicating.

Form $A_0$

In the solid state, anhydrous Form $A_0$ showed a tendency to take up water from the environment and to give rise under standard ICH stressed conditions, 40° C. and 75% RH to hydrate Forms $HC_0$ and $HD_0$ after 3 months. Chemical degradation was not observed in Compound I samples under these stressed conditions. Chemical degradation was only observed when Compound I was exposed to 110° C. (Table 39, Table 40 and Table 41).

TABLE 39

Stability of Form $A_0$ at 40° C./75% RH

| SAMPLE NUMBER | Elapsed Time (Days) | XRPD | DSC | HPLC |
|---|---|---|---|---|
| 1 | 5 | $A_0$ | 239.7 | 99.2% Compound I, 0.8% Compound E |
| 2 | 16 | $A_0$ | 239.4 | 99.2% Compound I, 0.8% Compound E |
| 3 | 29 | $A_0$ | 239.5 | 99.2% Compound I, 0.8% Compound E |
| 4 | 141 | $A_0, HC_0, HD_0$ | 240.0 | 99.0% Compound I, 0.9% Compound E |

TABLE 40

Stability of Form $A_0$ at 60° C./0% RH

| SAMPLE NUMBER | Elapsed Time (Days) | XRPD | DSC | HPLC |
|---|---|---|---|---|
| 1 | 7 | $A_0$ | 236.2 | 99.3% Compound I, 0.6% Compound E |
| 2 | 14 | $A_0$ | 236.1 | 99.1% Compound I, 0.8% Compound E |
| 3 | 28 | $A_0$ | 236.4 | 99.1% Compound I, 0.5% Compound E |

TABLE 41

Stability of Form $A_0$ at 110° C.

| SAMPLE NUMBER | Elapsed Time (Days) | XRPD | DSC | HPLC |
|---|---|---|---|---|
| 1 | 7 | $A_0$ | 236.2 | 98.7% Compound I, 1.1% Compound E |
| 2 | 14 | $A_0$ | 235.6 | 95.6% Compound I, 4.4% Compound E |
| 3 | 28 | $A_0$ | 238.0 | 93.4% Compound I, 6.2% Compound E |

Monohydrate Forms

In the solid state, Table 42, Table 43 and Table 44 show that all crystalline monohydrates were stable for 28 days when stored at 40° C. and 75% relative humidity.

TABLE 42

Stability of Form $HA_0$ at 40° C./75% RH

| SAMPLE NUMBER | Elapsed Time (Days) | XRPD | HPLC |
|---|---|---|---|
| 1 | 0 | $HA_0$ | 99.6% Compound I, ND Compound E |
| 2 | 7 | $HA_0$ | 99.5% Compound I, 0.1% Compound E |
| 3 | 26 | $HA_0$ | 99.0% Compound I, 0.4% Compound E |

ND = non-detectable

TABLE 43

Stability data for Form $HC_0$ at 40° C./75% RH

| SAMPLE NUMBER | Elapsed Time (Days) | XRPD | HPLC |
|---|---|---|---|
| 1 | 0 | $HC_0$ | 92.6% Compound I, 0.3% Compound E |
| 2 | 28 | $HC_0$ | 93.3% Compound I, 0.5% Compound E, 0.2% others |

TABLE 44

Stability data for Form $HD_0$ at 40° C./75% RH

| SAMPLE NUMBER | Elapsed Time (Days) | XRPD | HPLC |
|---|---|---|---|
| 1 | 0 | $HD_0$ | 93.5% Compound I, 0.3% Compound E |
| 2 | 7 | $HD_0$ | 92.2% Compound I, 0.9% Compound E |
| 3 | 13 | $HD_0$ | 92.3% Compound I, 0.7% Compound E |
| 4 | 28 | $HD_0$ | 92.3% Compound I, 0.7% Compound E |

Form $S4_0$

Form $S4_0$, an ethanol solvate, is transformed into monohydrate Form $HC_0$ after 9 days at 40° C./75% RH and remained in this state for 62 days (Table 45).

TABLE 45

Stability data for $S4_0$ at 40° C./75% RH

| SAMPLE NUMBER | Elapsed Time (Days) | XRPD | HPLC |
|---|---|---|---|
| 1 | 9 | $HC_0$ | 99.4% Compound I, 0.35% Compound E |
| 2 | 17 | $HC_0$ | 99.4% Compound I, 0.36% Compound E |
| 3 | 31 | $HC_0$ | 99.4% Compound I, 0.47% Compound E |
| 4 | 62 | $HC_0$ | 99.2% Compound I, 0.47% Compound E |

Form Conversion Mechanical Stress

Grinding by Mortar and Pestle

Approximately 100 mg of Compound I was ground at different times ranging from 5 to 27 min in an agate mortar. Samples were removed for XRPD and thermal analysis. The grinding process was stopped every 5 minutes to scrape and remix powder cakes at the curvature end of the jars to ensure homogenous grinding.

Milling by Wig-L-Bug®

A Wig-l-Bug® (Piketech, USA) was used to grind Compound I Form $A_0$, $HA_0$ and $HB_0$ (mixture of Forms $HC_0$ and $HD_0$). Each sample (50 mg) was ground for periods of 5 and 10 minutes or until no change was observed. Each milling was carried out in a 2.82 cm$^3$ container using 0.9 g stainless steel ball (0.6 mm diameter). The vial is swung through a 6.5° arc at 3200 rpm, causing the ball to strike the end of the vial at over 100 Hz.

Form $A_0$ Stability

Figure 49:
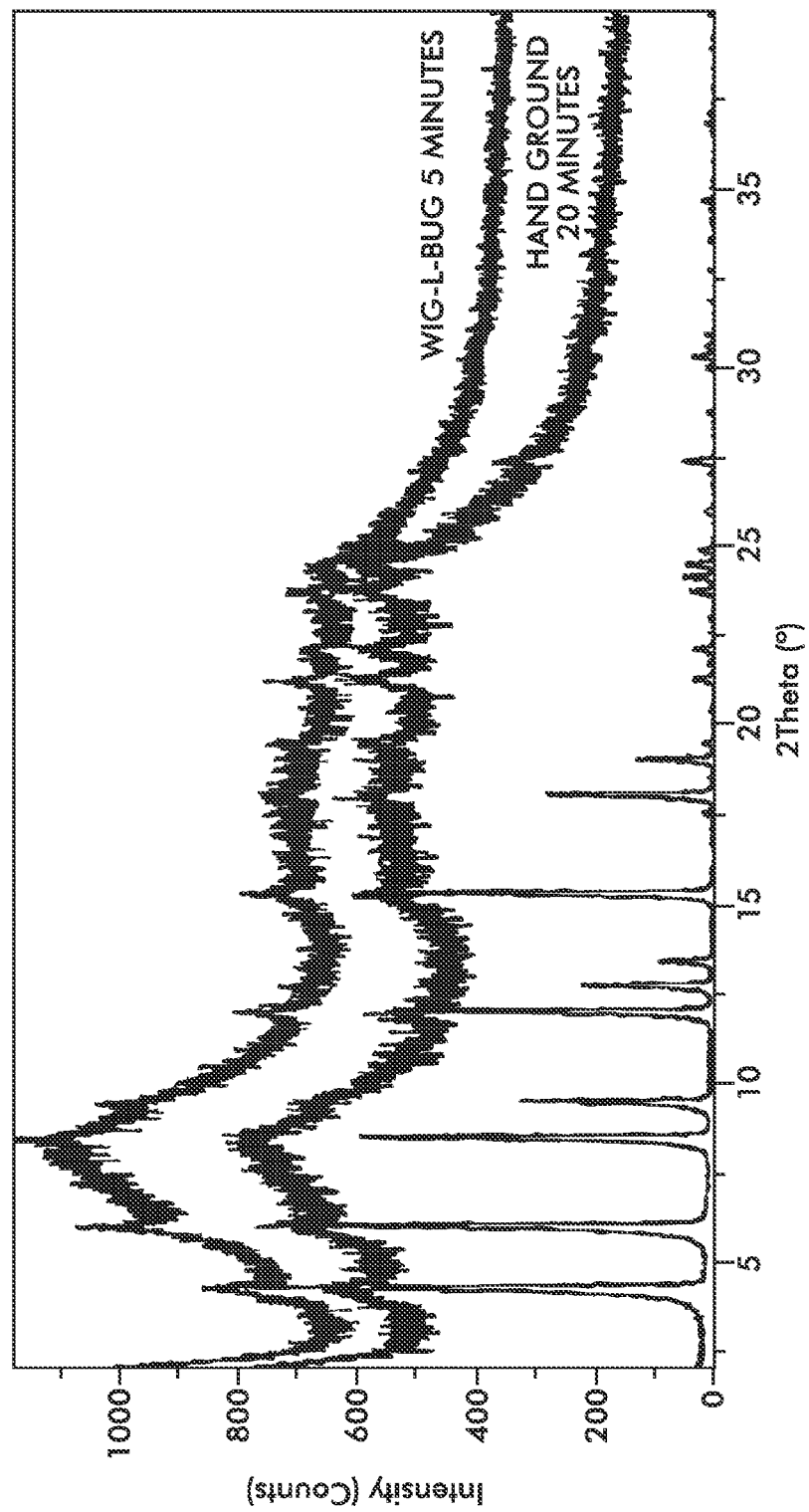
FIG. 49 depicts an overlay of X-ray Powder Diffractogram (XRPD) patterns of Form $A_0$ after grinding.
Figure 50:
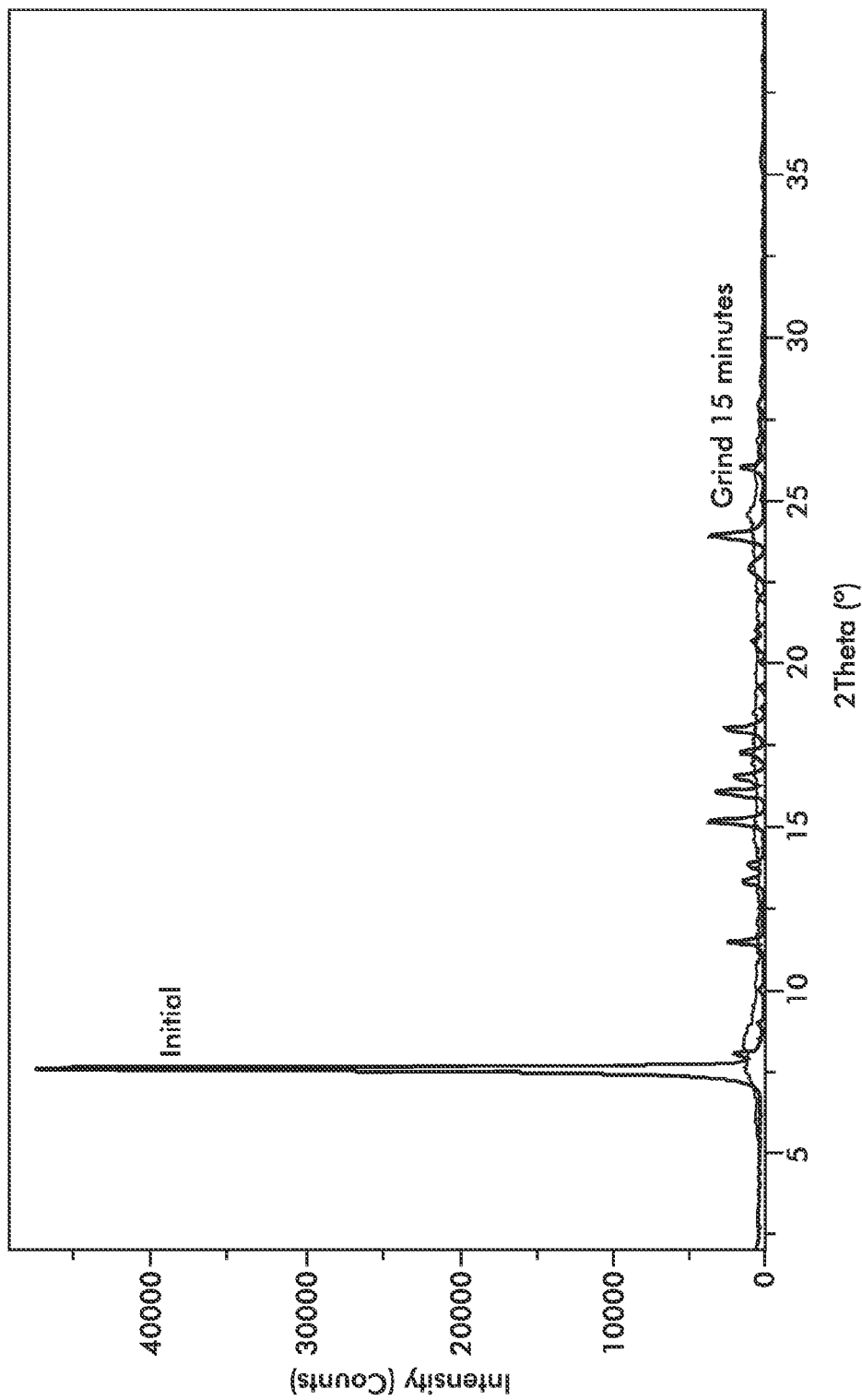
FIG. 50 depicts an overlay of X-ray Powder Diffractogram (XRPD) patterns of Form $HC_0$ and $HD_0$ after grinding for 15 minutes.

After twenty minutes (mortar and pestle) and five minutes (Wig-l-Bug®), the XRPD patterns showed that crystallinity had been significantly reduced. As the remaining peaks were in the same position as the starting material, the samples did not become completely amorphous (FIG. 49).

Forms $HA_0$, $HC_0$ and $HD_0$ Stability

After three five-minute grinding intervals, the XRPD pattern for ground Form $HB_0$ (a mixture of Forms $HC_0$ and $HD_0$) (FIG. 50) is similar to the pattern for ground $HA_0$. The XRPD peak at 7.6° (2θ) is reduced in intensity by a factor of approximately 30.

The DSC curves show a broad endotherm ranging from 50 to 100° C. that can be attributed to the release of water. The thermogram shows first a glass transition Tg located at ca. 113° C. (FIG. 51). The DSC indicates that the one observed exotherm corresponds to a one step recrystallization at 136° C. towards the metastable Form $B_0$. A broad endothermic event, that corresponds to the melting of the $B_0$ form and a final melt at 231° C. (Form $A_0$). An explanation for these events can be given if Forms $A_0$ and $B_0$ are considered to be monotropic, where Form $A_0$ is the more stable form.

It is meant to be understood that peak heights obtained as a result of the XRPD, VT-XRPD and single crystal diffraction pattern experiments may vary and will be dependent on variables such as the temperature, crystal size or morphology, sample preparation, or sample height in the analysis well of the PANalytical X Pert Pro diffractometer or Oxford diffraction CCD diffractometer.

It is also meant to be understood that peak positions may vary when measured with different radiation sources. For example, Cu—$K\alpha_1$, Mo—$K\alpha$, Co—$K\alpha$ and Fe—$K\alpha$ radiation, having wavelengths of 1.54060 Å, 0.7107 Å, 1.7902 Å and 1.9373 Å, respectively, may provide peak positions that differ from those measured with Cu—$K\alpha$ radiation.

It is further meant to be understood that the term "±0.2 degrees 2-theta" following a series of peak positions means that all of the peaks of the group which it follows are reported in terms of angular positions with a variability of ±0.2 degrees 2-theta. For example, "6.81, 8.52, 9.73, 12.04 and/or 13.25±0.2 degrees 2-theta" means "6.81±0.2 degrees 2-theta, 8.52±0.2 degrees 2-theta, 9.73±0.2 degrees 2-theta, 12.04±0.2 degrees 2-theta and/or 13.25±0.2 degrees 2-theta".

As those skilled in the art will appreciate, numerous modifications and variations of the present invention are possible in view of the above teachings. It is therefore understood that within the scope of the appended claims, the invention can be practiced otherwise than as specifically described herein, and the scope of the invention is intended to encompass all such variations.

Accordingly, a first embodiment of the invention provides a crystalline form of Compound I that is Form $A_0$ or Form $B_0$, or a mixture thereof.

A second embodiment of the invention provides the crystalline form of the first embodiment, wherein the crystalline form is Form $A_0$.

A third embodiment of the invention provides the crystalline form of the first embodiment, wherein the crystalline form is Form $B_0$.

A fourth embodiment of the invention provides the crystalline form of the second embodiment, characterized by an X-ray powder diffraction pattern comprising one or more of the following peaks: 4.32, 6.07, 8.55, 12.07 and 15.37±0.2 degrees 2-theta.

A fifth embodiment of the invention provides the crystalline form of the second embodiment, having an X-ray powder diffraction pattern substantially as depicted in FIG. 1.

A sixth embodiment of the invention provides the crystalline form of the third embodiment, characterized by an X-ray powder diffraction pattern comprising one or more of the following peaks: 7.16, 7.89, 10.77, 16.54, and 21.20±0.2 degrees 2-theta.

A seventh embodiment of the invention provides the crystalline form of the third embodiment, having an X-ray powder diffraction pattern substantially as depicted in FIG. 2.

An eighth embodiment of the invention provides a crystalline form of Compound I that is Form $HA_0$, Form $HC_0$ or Form $HD_0$ or a mixture thereof.

A ninth embodiment of the invention provides the crystalline form of the eighth embodiment, wherein the crystalline form is Form $HA_0$.

A tenth embodiment of the invention provides the crystalline form of the eighth embodiment, wherein the crystalline form is Form $HC_0$.

An eleventh embodiment of the invention provides the crystalline form of the eighth embodiment, wherein the crystalline form is Form $HD_0$.

A twelfth embodiment of the invention provides the crystalline form of the ninth embodiment, characterized by an X-ray powder diffraction pattern comprising one or more of the following peaks: 7.59, 15.12, 16.06, 17.94 and 23.89±0.2 degrees 2-theta.

A thirteenth embodiment of the invention provides the crystalline form of the ninth embodiment, having an X-ray powder diffraction pattern substantially as depicted in FIG. 3.

A fourteenth embodiment of the invention provides the crystalline form of the tenth embodiment, characterized by an X-ray powder diffraction pattern comprising one or more of the following peaks: 8.36, 8.71, 16.69, 17.39 and 24.59±0.2 degrees 2-theta.

A fifteenth embodiment of the invention provides the crystalline form of the tenth embodiment, having an X-ray powder diffraction pattern substantially as depicted in FIG. 4.

A sixteenth embodiment of the invention provides the crystalline form of the eleventh embodiment, characterized by an X-ray powder diffraction pattern comprising one or more of the following peaks: 7.60, 8.99 and 15.16±0.2 degrees 2-theta.

A seventeenth embodiment of the invention provides the crystalline form of the eleventh embodiment, having an X-ray powder diffraction pattern substantially as depicted in FIG. 5.

An eighteenth embodiment of the invention provides a crystalline form of Compound I that is Form $S2_0$, Form $S3_0$, Form $S4_0$, Form $S5_0$, Form $S6_0$, Form $S7_0$, Form $S9_0$, Form $S10_0$ or Form $S12_0$ or a mixture thereof.

A nineteenth embodiment of the invention provides the crystalline form of the eighteenth embodiment, wherein the crystalline form is Form $S2_0$.

A twentieth embodiment of the invention provides the crystalline form of the eighteenth embodiment, wherein the crystalline form is Form $S3_0$.

A twenty-first embodiment of the invention provides the crystalline form of the eighteenth embodiment, wherein the crystalline form is Form $S4_0$.

A twenty-second embodiment of the invention provides the crystalline form of the eighteenth embodiment, wherein the crystalline form is Form $S5_0$.

A twenty-third embodiment of the invention provides the crystalline form of the eighteenth embodiment, wherein the crystalline form is Form $S6_0$.

A twenty-fourth embodiment of the invention provides the crystalline form of the eighteenth embodiment, wherein the crystalline form is Form $S7_0$.

A twenty-fifth embodiment of the invention provides the crystalline form of the eighteenth embodiment, wherein the crystalline form is Form $S9_0$.

A twenty-sixth embodiment of the invention provides the crystalline form of the eighteenth embodiment, wherein the crystalline form is Form $S10_0$.

A twenty-seventh embodiment of the invention provides the crystalline form of the eighteenth embodiment, wherein the crystalline form is Form S12$_O$.

A twenty-eighth embodiment of the invention provides the crystalline form of the nineteenth embodiment, characterized by an X-ray powder diffraction pattern comprising one or more of the following peaks: 8.56, 14.64, 16.07, 22.24 and 23.02±0.2 degrees 2-theta.

A twenty-ninth embodiment of the invention provides the crystalline form of the twentieth embodiment, characterized by an X-ray powder diffraction pattern comprising one or more of the following peaks: 6.70, 8.67, 13.36, 16.80 and 16.85±0.2 degrees 2-theta.

A thirtieth embodiment of the invention provides the crystalline form of the twenty-first embodiment, characterized by an X-ray powder diffraction pattern comprising one or more of the following peaks: 8.42, 8.60, 13.92, 17.20 and 24.46±0.2 degrees 2-theta.

A thirty-first embodiment of the invention provides the crystalline form of the twenty-second embodiment, characterized by an X-ray powder diffraction pattern comprising one or more of the following peaks: 4.46, 7.67, 8.86 and 11.71±0.2 degrees 2-theta.

A thirty-second embodiment of the invention provides the crystalline form of the twenty-third embodiment, characterized by an X-ray powder diffraction pattern comprising one or more of the following peaks: 8.68, 11.10, 16.94, 17.39 and 23.31±0.2 degrees 2-theta.

A thirty-third embodiment of the invention provides the crystalline form of the twenty-fourth embodiment, characterized by an X-ray powder diffraction pattern comprising one or more of the following peaks: 4.50, 7.70, 8.90 and 11.76±0.2 degrees 2-theta.

A thirty-fourth embodiment of the invention provides the crystalline form of the twenty-fifth embodiment, characterized by an X-ray powder diffraction pattern comprising one or more of the following peaks: 8.34, 8.67, 16.68, 17.33 and 24.57±0.2 degrees 2-theta.

A thirty-fifth embodiment of the invention provides the crystalline form of the twenty-sixth embodiment, characterized by an X-ray powder diffraction pattern comprising one or more of the following peaks: 4.45, 7.62, 8.79, 11.62 and/or 17.67±0.2 degrees 2-theta.

A thirty-sixth embodiment of the invention provides the crystalline form of the twenty-seventh embodiment, characterized by an X-ray powder diffraction pattern comprising one or more of the following peaks: 7.63, 7.67, 9.00, 17.99 and 24.46±0.2 degrees 2-theta.

A thirty-seventh embodiment of the invention provides a process for preparing a crystalline form of Compound I that is Form A$_O$, comprising the steps of:
  a. Slurrying Compound I in a hydrocarbon(s) (such as heptane or toluene);
  b. Cooling the resulting slurry;
  c. Filtering the resulting slurry; and
  d. Drying the filter-cake.

A thirty-eighth embodiment of the invention provides the process of the thirty-seventh embodiment, wherein Compound I is slurried in 26 to 45 volumes of heptane.

A thirty-ninth embodiment of the invention provides the process of the thirty-eighth embodiment, wherein Compound I is slurried in 45 volumes of heptane.

A fortieth embodiment of the invention provides the process of the thirty-seventh embodiment, wherein step (a) is performed at 79 to 83° C.

A forty-first embodiment of the invention provides the process of the fortieth embodiment, wherein step (a) is performed at 85° C.

A forty-second embodiment of the invention provides the process of the thirty-seventh embodiment, wherein step (a) is performed for 24 to 48 hours.

A forty-third embodiment of the invention provides the process of the forty-second embodiment, wherein step (a) is performed for 45 hours.

A forty-fourth embodiment of the invention provides the process of the thirty-seventh embodiment, wherein step (b) occurs at a temperature of 30-65° C.

A forty-fifth embodiment of the invention provides the process of the forty-fourth embodiment, wherein step (b) occurs at a temperature of 65° C.

A forty-sixth embodiment of the invention provides the process of the thirty-seventh embodiment, wherein step (c) is performed at room temperature for 0.33 to 3 hours.

A forty-seventh embodiment of the invention provides the process of the forty-sixth embodiment, wherein step (c) is performed at room temperature for three hours.

A forty-eighth embodiment of the invention provides a process for preparing a crystalline form of Compound I that is Form A$_O$, comprising the steps of:
  a. dissolving Compound I in a solvent;
  b. filtering the resulting solution;
  c. partially distilling the solvent while adding an anti-solvent to precipitate Compound I;
  d. further distilling the resulting slurry while adding additional anti-solvent to reduce the volume of the solvent used in step (a);
  e. heating the slurry to achieve complete conversion to Form A$_O$;
  f. cooling;
  g. collecting the product via filtration; and
  h. drying.

A forty-ninth embodiment of the invention provides the process of the forty-eighth, wherein step (a) is performed using 27 to 35 volumes of THF.

A fiftieth embodiment of the invention provides the process of the forty-ninth embodiment, wherein step (a) is performed using 30 volumes of THF.

A fifty-first embodiment of the invention provides the process of the forty-eighth embodiment, wherein the solution produced via step (a) may optionally be treated with a metal scavenger or carbon.

A fifty-second embodiment of the invention provides the process of the forty-eighth embodiment, wherein the filtering step (b) comprises one or both of the following steps:
  (i) filtering to remove the metal scavenger; and
  (ii) polish filtering through a 1-micron inline cartridge filter.

A fifty-third embodiment of the invention provides the process of the forty-eighth, wherein the solvent present in step (c) is distilled to 60 to 90% of its original volume.

A fifty-fourth embodiment of the invention provides the process of the forty-eighth embodiment, wherein step (c) is performed using heptane as the anti-solvent.

A fifty-fifth embodiment of the invention provides the process of the forty-eighth, wherein step (d) is performed until less than 5% THF by volume remains.

A fifty-sixth embodiment of the invention provides the process of the forty-eighth embodiment, wherein step (e) is performed at a temperature of about 90 to 96° C.

A fifty-seventh embodiment of the invention provides the process of the forty-eighth embodiment, wherein step (e) may be optionally omitted.

A fifty-eighth embodiment of the invention provides the process of the fifty-sixth embodiment, wherein the slurry is agitated for about 3 to 5 hours.

A fifty-ninth embodiment of the invention provides the process of the forty-eighth embodiment, wherein step (f) is performed at ambient temperature (25±5° C.).

A sixtieth embodiment of the invention provides the process of the forty-eighth embodiment, wherein the filtration of step (g) is performed using a dry, inert gas.

A sixty-first embodiment of the invention provides the process of the forty-eighth embodiment, wherein step (h) is performed at a temperature up to 80° C.

A sixty-second embodiment of the invention provides the process of the forty-eighth embodiment, wherein the residual water and/or solvate(s) are azeotropically removed.

A sixty-third embodiment of the invention provides a pharmaceutical composition comprising Form $A_0$, Form $B_0$, Form $HA_0$, Form $HC_0$, Form $HD_0$, or a mixture thereof.

A sixty-fourth embodiment of the invention provides a process for the preparation of Compound I, Compound I

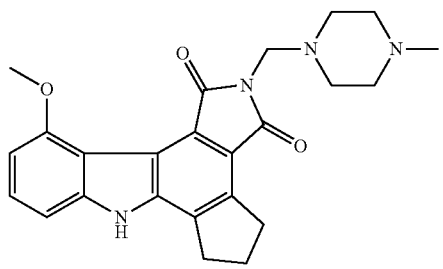

comprising the step of reacting Compound A,

Compound A

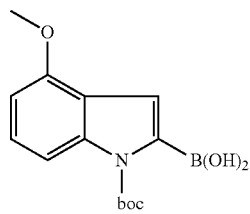

with 1,1,1-trifluoromethanesulfonic acid 1-cyclopenten-1-yl ester to produce Compound B, Compound B

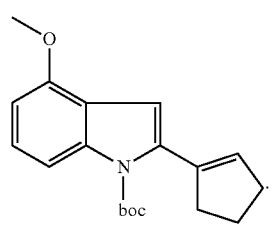

A sixty-fifth embodiment of the invention provides a process for the preparation of Compound I Compound I

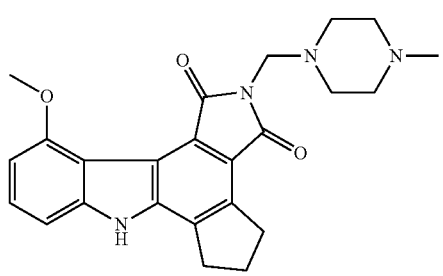

comprising the step of reacting Compound C,

Compound C

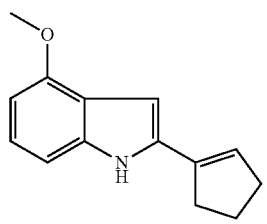

with maleimide to produce compound D,

Compound D

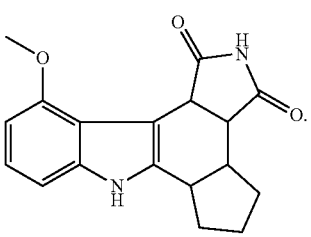

We claim:

1. A crystalline form of Compound I that is Form $A_0$ or Form $B_0$, or a mixture thereof.

2. The crystalline form of claim 1, wherein the crystalline form is Form $A_0$.

3. The crystalline form of claim 1, wherein the crystalline form is Form $B_0$.

4. The crystalline form of claim 2, characterized by an X-ray powder diffraction pattern comprising one or more of the following peaks: 4.32, 6.07, 8.55, 12.07 and 15.37±0.2 degrees 2-theta.

5. The crystalline form of claim 2, having an X-ray powder diffraction pattern substantially as depicted in FIG. 1.

6. The crystalline form of claim 3, characterized by an X-ray powder diffraction pattern comprising one or more of the following peaks: 7.16, 7.89, 10.77, 16.54, and 21.20±0.2 degrees 2-theta.

7. The crystalline form of claim 3, having an X-ray powder diffraction pattern substantially as depicted in FIG. 2.

8. A crystalline form of Compound I that is Form $HA_0$, Form $HC_0$ or Form $HD_0$ or a mixture thereof.

9. The crystalline form of claim 8, wherein the crystalline form is Form $HA_0$.

10. The crystalline form of claim 8, wherein the crystalline form is Form $HC_0$.

11. The crystalline form of claim 8, wherein the crystalline form is Form $HD_0$.

12. The crystalline form of claim 9, characterized by an X-ray powder diffraction pattern comprising one or more of the following peaks: 7.59, 15.12, 16.06, 17.94 and 23.89±0.2 degrees 2-theta.

13. The crystalline form of claim 9, having an X-ray powder diffraction pattern substantially as depicted in FIG. 3.

14. The crystalline form of claim 10, characterized by an X-ray powder diffraction pattern comprising one or more of the following peaks: 8.36, 8.71, 16.69, 17.39 and 24.59±0.2 degrees 2-theta.

15. The crystalline form of claim 10, having an X-ray powder diffraction pattern substantially as depicted in FIG. 4.

16. The crystalline form of claim 11, characterized by an X-ray powder diffraction pattern comprising one or more of the following peaks: 7.60, 8.99 and 15.16±0.2 degrees 2-theta.

17. The crystalline form of claim 11, having an X-ray powder diffraction pattern substantially as depicted in FIG. 5.

18. A crystalline form of Compound I that is Form $S2_0$, Form $S3_0$, Form $S4_0$, Form $S5_0$, Form $S6_0$, Form $S7_0$, Form $S9_0$, Form $S10_0$ or Form $S12_0$ or a mixture thereof.

19. A process for preparing a crystalline form of Compound I that is Form $A_0$ according to claim 2, comprising the steps of:
   a. Slurrying Compound I in a hydrocarbon(s) (such as heptane or toluene);
   b. Cooling the resulting slurry;
   c. Filtering the resulting slurry; and
   d. Drying the filter-cake.

20. A process for preparing a crystalline form of Compound I that is Form $A_0$ according to claim 2, comprising the steps of:
   a. dissolving Compound I in a solvent;
   b. filtering the resulting solution;
   c. partially distilling the solvent while adding an anti-solvent to precipitate Compound I;
   d. further distilling the resulting slurry while adding additional anti-solvent to reduce the volume of the solvent used in step (a);
   e. heating the slurry to achieve complete conversion to Form $A_0$;
   f. cooling;
   g. collecting the product via filtration; and
   h. drying.

21. A pharmaceutical composition comprising Form $A_0$, Form $B_0$, Form $HA_0$, Form $HC_0$, Form $HD_0$, or a mixture thereof.

22. A pharmaceutical composition comprising Form $A_0$, Form $B_0$ or a mixture thereof.

* * * * *